(12) United States Patent
Davis et al.

(10) Patent No.: US 6,749,567 B2
(45) Date of Patent: Jun. 15, 2004

(54) NONINVASIVE METHOD OF MEASURING PHYSIOLOGIC PARAMETERS

(75) Inventors: Charles L. Davis, Beaverton, OR (US); Patrick D. Harrison, Wilsonville, OR (US)

(73) Assignee: Hemonix, Inc., Beaverton, OR (US)

( * ) Notice: Subject to any disclaimer, the term of this patent is extended or adjusted under 35 U.S.C. 154(b) by 0 days.

(21) Appl. No.: 10/142,225

(22) Filed: May 9, 2002

(65) Prior Publication Data

US 2002/0188206 A1 Dec. 12, 2002

Related U.S. Application Data

(60) Provisional application No. 60/289,910, filed on May 9, 2001.

(51) Int. Cl.$^7$ ................................................ A61B 5/00
(52) U.S. Cl. ...................... 600/300; 600/485; 600/504; 600/507; 600/508
(58) Field of Search ................................ 600/300–301, 600/485–508, 561, 547

(56) References Cited

U.S. PATENT DOCUMENTS

| | | | | |
|---|---|---|---|---|
| 5,423,322 A | * | 6/1995 | Clark et al. | .................. 600/485 |
| 6,554,774 B1 | | 4/2003 | Miele | |
| 6,561,986 B2 | | 5/2003 | Baura et al. | |
| 2003/0135124 A1 | | 7/2003 | Russell | |

OTHER PUBLICATIONS

Jaap H. J. Muntinga and Klaas R. Visser, *Estimation of blood pressure-related parameters by electrical impedance measurement*, Journal of Applied Physiology, Nov. 1992; 73(5), pp 1946–1957.

P. Gizdulich and K. H. Wesseling, *Forearm arterial pressure–volume relationships in man*, Clin. Phys. Physiol. Meas., 1988, vol. 9, No. 2, pp 123–132.

* cited by examiner

Primary Examiner—Robert L. Nasser
Assistant Examiner—Patricia C. Mallari
(74) Attorney, Agent, or Firm—Pauley Petersen & Erickson

(57) ABSTRACT

The present invention provides means and methods for noninvasively identifying the blood pressure characteristics in each of the seven types of vessels in the circulatory system, including the central venous pressure (CVP) through a single monitoring system using fluid depletion plethysmography. Known pressure is applied to a body region in increasing amounts to force blood volume from the body region in step-wise fashion through each vessel type. Blood volume depletion for each vessel type is measured by the increasing electrical impedance of the body part during depletion and is plotted against the increasing pressure data. The resulting series of slope changes within the plotted curve reveals the blood pressure for each vessel type. The data obtained may further be used to determine vessel wall compliance/tension as well as standard measurements such as pulse and large artery systolic and diastolic pressure. Release of the applied pressure may then yield similar data by measuring blood volume replenishment against the decreasingly applied pressure during the same diagnostic operation. The method is not dependent on oscillometric or pulsatile measurement methods. The electrical leads of the impedance/volume sensor and the means for applying pressure to the body part are coextensive to ensure accurate indication of blood volume depletion and replenishment in the body region under pressure and may be incorporated into a single integrated structure.

67 Claims, 35 Drawing Sheets

Vascular Circuit with State Transition Boundaries and Fluid Compartments

Blood Pressure versus Anatomic Vascular Location

Oscillometric Pressure versus Cuff Pressure

Nyboer Parallel Conductor Model

General Parallel Conductor Model

Parallel Volume Model versus Pressure

The Body Region of the Subject at Volume/Pressure State 0

First Embodiment Monitor with Inflatable Cuff Pressure Generator and Bioimpedance Fluid Volume Sensor Methods of Pressure Generation and Application Uniform Pressure Generation Non-Uniform Pressure Generation Examples of Body Region Surface Coextensivity Impedance Volume Sensor Inflatable Cuff Pressure Generator with Impedance Volume Sensor Pressure Generator – PG Pressure State Monitor - PSM Pressure Control Unit - PCU Volume Sensor - VS Volume State Monitor - VSM Volume / Pressure Analyzer - VPA Impedance versus Time with Increasing Pressure showing Fluid Volume Depletion Impedance versus Time with Decreasing Pressure showing Fluid Volume Replenishment Volume Depletion Impedance Data with Increasing Pressure and Volume Replenishment Impedance Data with Decreasing Pressure The Body Region of the Subject at Volume/Pressure State 1

The Body Region of the Subject at Volume/Pressure State 7

The Body Region of the Subject at Volume/Pressure State 8

Vascular Pressure Profile

Vascular Volume Profile

Vessel Wall Compliance Profile

Impedance Data Converted to Admittance Data

Enlarged Region of Combined Vascular and Nonvascular Fluid Compartments

Determination of Nonvascular Fluid Compartment Function by Regression Analysis

Derivation of Start Point of Changes in Nonvascular Fluid Function

Blood Admittance Changes from Increasing Pressure with Nonvascular Fluid Function Removed Vascular Volume from Increasing Pressure with Nonvascular Fluid Function Removed Vascular Volume from Decreasing Pressure with Nonvascular Fluid Function Removed Vessel Compression Forces The Change in Cuff Pressure with Increasing Cuff Pressure State Transitions Shown in Filtered Impedance Data versus Increasing Pressure State Transitions shown in Blood Admittance Data versus Increasing Pressure State Transitions shown in Blood Volume Data versus Increasing Pressure State Transitions shown in Filtered Impedance Data versus Decreasing Pressure

NONINVASIVE METHOD OF MEASURING PHYSIOLOGIC PARAMETERS

CROSS-REFERENCE TO RELATED APPLICATION

This application claims priority from Provisional Application Serial No. 60/289,910 filed on May 9, 2001.

BACKGROUND OF THE INVENTION

1. Field of the Invention

The present invention relates to a method of noninvasive measurement of physiologic parameters in a subject. In particular the present invention relates to a method of noninvasive and non-pulsatile measurement of physiologic fluid parameters as well as a combination of nonpulsatile and pulsatile physiologic parameters for a subject, or patient, which may include any animal with body fluid compartments.

2. Discussion of the Related Art

Known art noninvasive methods have been disclosed for determining physiologic parameters such as arterial blood pressure (U.S. Pat. No. 4,178,918), pulse oximetry (U.S. Pat. No. 3,998,550), and vascular compliance (Shankar, U.S. Pat. Nos. 5,241,963 and 5,724,981) using pulsatile signals acquired from the subject. However, these methods are dependent upon and limited by naturally occurring pulsations in the arteries of the subject.

Other known art noninvasive methods have been disclosed for determination of vascular behaviors by rheoplethysmography (Piquard, U.S. Pat. No. 4,169,463) and determination of blood pressure in the veins and arteries (Blazek et al., U.S. Pat. No. 5,447,161) by observing non-pulsating signals acquired from the subject by a technique known as "venous occlusion plethysmography." This method relies upon a time-based accumulation of blood in the veins of the subject in order to make the physiologic measurements. However, these methods require that the occlusive device be proximal or downstream from the measuring device along the body region of the subject. Also, these methods further lack the ability to calibrate directly to the subject and rely upon coefficients of standardization, which are characteristic of the healthy vascular operation of a normal limb of the same type as the limb under study. In some instances, these methods are limited to application on fingers and toes.

Cardiovascular System Background

Referencing Table 1 and FIGS. 1–2, the functional parts of the cardiovascular system include the heart, the lungs, the arteries, the capillary beds, the veins, and the blood. The cardiovascular system is comprised of two independent vascular circuits, the pulmonary circuit and the systemic circuit. Each vascular circuit has a system of arteries and a system of veins separated by a capillary bed. Blood is primarily a composite of plasma and red blood cells. The human heart is a four-chamber pump organized as a right half and a left half with two sequential pumping chambers in each half. The upper pumping chamber of the heart is called the atria and the lower pumping chamber of the heart is called the ventricle. The atria serve as filling chambers for the ventricles and contract prior to the time of contraction of the ventricle. This difference in time of contraction allows the atria to pre-load the ventricles prior to the ventricular contraction. The ventricles are the primary pumping chamber for each circuit. The right ventricle pumps blood into the pulmonary circuit and the left ventricle pumps blood into the systemic circuit.

Thus, the right half of the heart supplies blood flow to the pulmonary circuit and the left half of the heart supplies blood flow to the systemic circuit. Each circuit returns blood to the other side of the heart through its associated venous system. The pulmonary circuit is composed of the pulmonary arteries, the lungs, and the pulmonary veins. The pulmonary circuit oxygenates the blood in the lungs and returns the oxygenated blood to the left heart to be pumped into the systemic circuit. The systemic circuit, composed of the systemic arteries, the systemic capillary beds, and the systemic veins, supplies oxygenated blood to all areas of the body. The systemic blood flow is then returned to the right heart by the systemic veins.

The Origin of Arterial Pulsations

The heart produces pulsatile blood flow in the arteries by forcing a volume of blood into the aorta during each contraction of the heart. This volume of blood, known as the "stroke volume", causes an arterial pressure wave to propagate throughout the systemic arteries up to the arterioles (FIG. 1). The arterioles, which are the smallest arteries in the systemic circuit, have the ability to dynamically vary the resistance to blood flow (Table 1) in response to demands from the end cells of the body. This resistance to blood flow is known as the "peripheral vascular resistance". The peripheral vascular resistance causes a reduction in arterial blood pressure as the blood flows through the arterioles into the capillary bed as shown in FIG. 2.

In particular, the arterial blood pressure before the arterioles is highly pulsatile and time variant, while after the arterioles, the arterial blood pressure is primarily steady state, lacking any significant pulsation. Generally, known noninvasive methods of measuring arterial blood pressure, pulse oximetry, and vascular compliance, rely upon the pulsation of arterial blood pressure. As shown in FIG. 2, the blood pressures that exist in the capillary beds and veins after the arterioles, is substantially non-pulsatile and therefore does not lend itself for measurement by known noninvasive pulsatile plethysmographic methods. Furthermore, other physiologic attributes such as oxygen saturation of the blood and compliance of the vessel wall in the non-pulsatile vessels cannot be determined by methods that are reliant on arterial pulsations.

Vascular Compliance and Vessel Wall Tension

Blood vessels have elastic walls that stretch in response to the volume of blood contained within them. The degree of elasticity or tension of the vessel wall determines how much pressure is produced within a vessel for a specific amount of blood volume or change in blood volume. The blood vessel wall is an active organ with the ability to vary its compliance, or its inverse, wall tension, as discussed below, dependent on sympathetic nervous stimulation to the vessel.

In arteries of the subject, there is both a steady state and a pulsatile time variant volume of blood in the vessel. This is due to the stroke volume of blood forced into the arteries by each contraction of the heart. The increased stroke volume of blood in the arteries caused by the heartbeat creates pulsatile pressure waves that propagate to a point of extinction within the arterial bed. The actual point of extinction of the pulsatile pressure wave can be dependent upon the physiologic state of the arteries of the subject but is generally thought to be in the small arteries and before the arterioles. The amount of arterial pulse pressure change that occurs during each cardiac cycle is dependent on: the elasticity of the arterial wall, the stroke volume produced by the heartbeat, and the peripheral vascular resistance of the systemic circuit.

The elasticity of the vessel is commonly referred to as the "vascular compliance". Vascular compliance is defined as the rate of change of volume in the vessel versus the rate of change of pressure within the vessel. The inverse of compliance is called the vessel wall tension. Compliance and tension are in effect a measure of the level of elasticity or stiffness of the vessel wall. The loss of elasticity of the blood vessel wall contributes to the disease state known as hypertension or elevated blood pressure. It has been extensively reported in medical literature that both a thickening of the blood vessel wall (Atherosclerosis) as well as a plaquing of the interior lining of the blood vessel (Arteriosclerosis) contributes to a reduction in blood vessel elasticity and a general increase in arterial blood pressure. Furthermore, pathologies of the sympathetic nervous system and the adrenal medullae have been shown to dramatically affect the tension or compliance of the blood vessel wall.

The compliance of a vein is generally six to eight times greater than the compliance of an artery. Therefore, veins can accept and hold much larger volumes of blood at lower pressures than arteries. The tension of the vein wall and the volume of blood that it is containing regulate the venous blood pressure. The tension or compliance of the vein is regulated by the sympathetic nervous system. Body fluid volumes are primarily controlled by the function of the kidneys. A device that noninvasively determines the compliance or tension of the compartments throughout the circulatory system would be beneficial in the diagnosis and management of cardiovascular diseases.

Venous Blood Pressure

Venous blood pressure is of particular interest to healthcare providers because it is a critical parameter in the diagnosis and treatment of a variety of diseases such as heart failure, acute myocardial infarction, pulmonary hypertension, renal failure, and deep vein thrombosis. Furthermore, it would be a valuable physiologic parameter in the triage of emergency care patients for detection of cardiovascular and hemodynamic distress.

Central venous pressure (CVP), also known as the right atrial filling pressure, is of particular interest in diagnosing and managing subjects afflicted with these disease states. Since Venous pressure is a low, substantially non-pulsatile, time invariant physiologic parameter, there has been no prior method demonstrated which directly measures its value noninvasively. Heretofore, CVP has been measured by the expensive and invasive surgical insertion of a transducing catheter into the subject. Therefore, the ability to measure noninvasive central venous pressure with an easy to use noninvasive device would have a substantial impact on the quality and cost of healthcare delivery.

Arterial Blood Pressure Measurement

Arterial blood pressure has been measured by both invasive and noninvasive methods in the known art. Invasive blood pressure monitoring requires the insertion of a catheter into an artery for direct transduction of arterial pressure data. Due to the invasive nature of this method, it is considered a separate art and will not be further reviewed here. Two primary known methods of noninvasive arterial blood pressure monitoring, the auscultatory method and the oscillometric method, are discussed below.

Auscultatory Blood Pressure Measurement

The conventional auscultatory method of non-invasive blood pressure (NIBP) monitoring relies upon the sounds made by the blood coursing through a partially restricted artery. A clinician, e.g. a physician, a nurse, a medical technician or a paramedic, wraps a blood pressure cuff around the limb of the subject and inflates the bladder that is built into the cuff to exert on the arm a counter-pressure that exceeds the subject's systolic blood pressure and consequently occludes the flow of blood through the arteries in the limb. The clinician then slowly releases the cuff pressure while simultaneously observing the pressure indicated by a cuff pressure indicator and listening through a stethoscope for the so-called Korotkoff sound generated within the lower brachial artery. The Korotkoff sound is absent when the bladder counter-pressure is above systolic or below diastolic pressure. The onset of the Korotkoff sound is taken as indicating systolic pressure and the subsequent disappearance of the Korotkoff sound is taken as indicating the diastolic pressure.

The auscultatory method is subject to disadvantage because it requires that a clinician listen for the Korotkoff sound. Further, the precise point of the onset and disappearance of the Korotkoff sound are somewhat subjective and accordingly two clinicians can provide significantly different blood pressure values for the same subject. In addition, unless the clinician releases the cuff pressure slowly in the region of the systolic and diastolic pressures, it is difficult to relate the onset and disappearance of the Korotkoff sound precisely to pressure values. Moreover, the mean pressure cannot be reliably measured directly by the auscultatory method since there is not a definitive sound to identify the mean pressure value. The clinician may estimate the mean pressure from the systolic and diastolic pressures based on knowledge of the typical blood pressure waveform.

Oscillometric Blood Pressure Measurement

The wall of a blood vessel of a subject is elastic and therefore is distended cyclically when pressure waves induced by cardiac activity propagate through the vessel. When an external counter-pressure is applied to a limb of a subject by a cuff bladder circumscribing the limb, the pressure within the bladder is communicated through the tissue bed and fluids of the limb to the wall of the arteries within the limb.

Conversely, the pressure wave within the artery generated by the heart contraction is communicated through the arterial wall, tissue bed and fluids of the limb into the bladder and the fluid in the bladder. Consequently, the pressure of the fluid in the bladder is modulated by the subject's vascular pressure changes in the limb. These modulations of pressure within the bladder are commonly referred to as oscillations.

The variation in amplitude of the pressure changes induced in the bladder can be measured and is used in the oscillometric method of noninvasive blood pressure monitoring. The amplitude of each oscillation is recorded versus the value of cuff counter-pressure at which it occurred. In the oscillometric method, the cuff bladder is inflated to a pressure above systolic and the cuff pressure is gradually released, as in the case of the auscultatory method, and during the release of cuff pressure the amplitude of pressure variations in the bladder are measured.

The bladder pressure value is filtered, mathematically or electronically or the like, to separate the oscillating and steady-state components of the bladder pressure. The oscillating and steady-state pressure components are amplified and recorded separately. The magnitude of the steady-state component is a measure of the counter-pressure applied to the limb by the bladder while the oscillating component is used to develop the oscillometric complex from which can be determined the mean, systolic, and diastolic pressure values of the subject.

The oscillating component waveform has a characteristic shape, being composed of oscillations at pulse rate within an envelope that initially increases in amplitude then declines to a minimal value, as shown in FIG. 3. The characteristic sequence of oscillations of increasing and decreasing peak-to-peak amplitude versus counter-pressure is known as the oscillometric complex. Since the maximum change in bladder pressure occurs when the counter-pressure is equal to the mean blood pressure, the mean blood pressure is equal to the counter-pressure at which the pressure wave oscillations reach their maximum amplitude.

The maximum peak-to-peak amplitude is multiplied by a derived factor X to define a systolic detection amplitude and by a derived factor Y to define a diastolic detection amplitude. A search algorithm examines the oscillations of the oscillometric complex, starting from the mean detection point and moving towards higher counter-pressure, to identify the first pulse of peak-to-peak amplitude less than the systolic detection amplitude and defines the occurrence of this pulse as the systolic detection point. Similarly, the search algorithm examines the pulses of the oscillometric complex, starting from the mean detection point and moving towards lower counter-pressure, to identify the first pulse of peak-to-peak amplitude less than the diastolic detection amplitude and defines the occurrence of this pulse as the diastolic detection point. The counter-pressure associated with systolic detection point is reported as the systolic pressure and the counter-pressure associated with the diastolic detection point is reported as the diastolic pressure. The oscillometric method thusly determines the mean blood pressure and estimates the systolic pressure and the diastolic pressure.

The advantage of oscillometry, i.e. the oscillometric method, is that it is easily automated and can serve to take repeated intermittent blood pressure measurements over relatively short periods of time, such as once per minute.

Body Fluid Compartments—Volume and Status Monitoring

Fluids within the body of a subject are referred to herein as compartmentalized in vascular and nonvascular, and in some instances extracellular fluid and intracellular fluid, compartments. The extracellular fluid compartment contains all fluids that exist outside of cells and include interstitial fluid, blood, plasma, lymph, cerebrospinal fluid, intraocular fluid, gastrointestinal fluid, and fluids of the potential spaces. Intracellular fluids are all fluids contained within cells of the body including the red blood cells. In general, 60% to 70% of the total body fluid in a subject is contained within the cells of the subject with the remaining fluid being contained in extracellular fluid compartments such as the various vascular vessel types, each of which is deemed a different compartment for purposes of explanation herein. Understanding the distribution of body fluids in each vascular, nonvascular, intracellular or extracellular fluid compartment can be indicative of disease states of the subject and means and method for doing so would be a desirable addition to the art.

Plethysmography

A plethysmograph measures a change in volume and records the changing value. Plethysmography has been utilized in physiologic monitoring to measure the respiration rate, the oxygen saturation of blood, and the pulse volume in arteries. Various methods of plethysmography have been provided in known art including volume plethysmography, impedance plethysmography (e.g., Shankar, U.S. Pat. Nos. 5,241,963 and 5,724,981), which are forms of pulse plethysmography and venous occlusion plethysmography (e.g., Piquard, U.S. Pat. No. 5,169,463, supra.). As evidenced in the art, the plethysmograph, independent of sensing modality, measures a time rate of increase or decrease in volume within the subject.

Volume Plethysmography

Volume plethysmography is a method of noninvasive physiologic measurement described by Shankar for measuring the volume of arterial pulsations in the limbs of a subject. Shankar provides a method of measuring pulse volumes from the arteries of subjects and relating that information to the state of atherosclerosis of the arteries. This plethysmographic method is reliant upon arterial pulsations generated within the body of the subject and therefore is incapable of measuring the physiologic characteristics of vessels of the body which do not contain pulsatile flow.

Venous Occlusion Plethysmography

Venous occlusion plethysmography is a method of non-invasive physiologic measurement reliant upon the accumulation of fluids in the veins of a body region that is distal or upstream from a venous occlusion device. Reference for Venous Occlusion Plethysmography is made to "Principles of Applied Biomedical Instrumentation", $3^{rd}$ Ed, L. A. Geddes, L. E. Baker, John Wiley and Sons, 1989. The venous occlusion device must be capable of applying a pressure that is greater than the venous pressure and less than the arterial pressure to the body region in order to cause a time variant accumulation of venous blood in the upstream-monitored body region of the subject. It will be noted that "upstream" is determined according to the area of higher fluid pressure, and in this instance as relative to the occlusion, although upstream may be the physically distal position of the body limb.

Because venous occlusion plethysmography relies upon the accumulation of fluid in the upstream body region of the subject (again relative to the occlusion), the method is limited to closed body regions such as limbs, legs, arms, fingers, and toes. Physiologic parameters are measured by plethysmographic methods from the accumulating fluids during the period of venous occlusion. A problem with this method is that the physiologic measurements are made on a body region that is being altered from its natural state prior to determination of the desired physiologic parameters. As abnormal fluid volumes accumulate in the fluid compartments of the upstream body region, fluid pressure increases above normal and venous compliance decreases below normal. These abnormal conditions can introduce errors and uncertainty in the physiologic measurements.

Impedance Plethysmography

Impedance plethysmography is the measurement of impedance changes in a subject by measuring the time variant electrical impedance of the subject and determining volume characteristics based upon measured impedance values. Known impedance plethysmographic methods have largely been limited to the measurement of impedance changes caused by pulsatile, or time varying, volume changes in the arteries of the subject and to venous occlusion plethysmography which depends upon a separation between the pressure applying device and the impedance sensing device.

The ability to non-invasively measure volumetric changes in the vascular bed by impedance plethysmography has been extensively discussed in the literature including Nyboer, J., "*Electrical Impedance Plethysmography: A Physical And Physiologic Approach To Peripheral Vascular Study.*" Circulation, 2:811–821, 1950; Geddes, and Sadler, "*The Specific Resistance Of Blood At Body Temperature.*" —Med. Biol. Eng. 11(3):336–339, 1973; Shankar, Webster, and Shao, "*The Contribution of Vessel Volume Change and Blood Resistivity Change to the Electrical Impedance Pulse*", IEEE Transactions on Biomedical Engineering, Vol. BME-32, No. 3, Mar. 1985; Chumlea, Guo, Baumgartner, and Siervogel, "*Determination Of Body Fluid Compartments With Multiple Frequency Bioelectric Impedance.*" —Human Body Composition—In Vivo Methods, Models, and Assessment, Plenum Press, Basic Life Sciences Vol. 60; Shimazu, Yamakoshi, Togawa, and Fukuoka, "*Evaluation Of Parallel Conductor Theory For Measuring Human Limb Blood Flow By Electrical Admittance Plethysmography*", January 1981, IEEE Transactions on Biomedical Engineering; "*Encyclopedia of Medical Devices and Instrumentation*", Volume 3, pg. 1633, 1988, John Wiley & Sons, New York; Nyboer, "*Electrical Impedance Plethysmography,*" $2^{nd}$ Edition, Thomas Books, Springfield, Ill., 1970; and Lifshitz, "*Electrical Impedance Cephalography, Electrode Guarding And Analog Study,*" Ann. N.Y. Acad. Sci. 170:532–549, 1970.

Impedance monitoring is based upon the relationship E=I*R, known as Ohm's Law, which states that the voltage drop (E) across a length of conductor is equal to the current flowing through the conductor (I) times the resistance of the conductor (R). When the current is an alternating current (AC), the resistance element becomes a vectorial sum of a real component (R) as well as an imaginary component (jX) and is referred to as impedance. The complex nature of impedance arises from the presence of capacitance or inductance in the conductive material. The impedance (Z) of a conductor is represented as a complex number (Z=R+jX) composed of the resistance (R) and reactance (jX) of the conductor. Furthermore, the admittance (Y) of a substance is equal to the inverse of the impedance or 1/Z of that substance. The phase angle ( ) of impedance (Z) is the $TAN^-$ (jX/R).

Nyboer was the first to apply the formula for the resistance of a homogeneous volume conductor to predict the relationship between impedance changes and blood volume changes. The electrical impedance (Z) of a body region ($_b$), can be expressed in terms of its cross sectional area ($a_{cs}$), length (L), and resistivity ( ) of the material.

$$Z_b = {}_b L / a_{cs} \tag{1}$$

$$a_{cs} = {}_b L / Z_b \tag{2}$$

$$a_{cs} = {}_b L Y_b \tag{3}$$

Since the volume of a vessel segment is $V_b = L \cdot a_{cs}$, then the electrical impedance can be expressed in terms of the segmental or regional volume which can be expressed in terms of the electrical impedance as shown in equations 4 and 4a respectively.

$$Z_b = {}_b L^2 / V_b \tag{4}$$

$$V_b = {}_b L^2 / Z_b \tag{4a}$$

Nyboer further assumed that the segmental blood volume change (V) could be modeled as the impedance change (Z) due to the change in blood volume electrically in parallel with the basal tissue impedance $Z_t$ (see FIG. 4). This led to the well-known "Nyboer Formula,"

$$V_b = -{}_b L^2 Z_b / Z_t^2 \tag{5}$$

This relationship between the change in volume of blood and its associated change in impedance is the basis of impedance plethysmography. The Nyboer formula has been widely practiced in the known art with mixed results.

The Nyboer formula is dependent upon a changing impedance value ($Z_b$) in order to determine a changing volume ($V_b$) within the body of the subject. Further, the knowledge of the specific value of $_b$ for the particular subject is critical to the accuracy and reliability of the volume data determined by the Nyboer formula. It is further known that the resistivity of blood is dependent on the hematocrit of the particular subject and therefore will vary from subject to subject.

In the Nyboer formula (5), it is assumed that all elements are constant except $Z_b$ indicating the pulsatile volume changes in the arteries. This assumption is only true if there are no other concurrent material volume changes occurring in the monitored body region of the subject. However, in practical applications of impedance plethysmography, this assumption is often not true and therefore the Nyboer formula can often generate unreliable and inaccurate results due to respiration and motion artifacts in the impedance data.

Further, the Nyboer formula assumes a composite resistivity for the diverse elements that comprise $Z_t$. This composite resistivity may vary from subject to subject and contribute uncertainty to the volume values derived using the Nyboer formula. It is important to note that even though the Nyboer formula has been widely used in the measurement of physiologic parameters, the Nyboer methodology has been criticized by some practitioners as being unreliable and inaccurate.

Parallel Conductor Theory

It is generally known that a body region of the subject is composed of a variety of conductive materials including fluids, tissue, fat, and bone. It is further known that cell membranes and vessel walls surrounding fluids may affect the conductivity of the cells and vessels. Therefore, a body region of the subject is considered a composite conductive medium with multiple current pathways through the body region. Each conductive pathway is considered to have unique electrical conductivity characteristics. The "Parallel Conductor Theory" describes the subject as a parallel conductor model composed of various conductive elements that represent different materials of the subject's body composition. The parallel conductor hypothesis models a body region as a set of parallel conductors in which the volume of arterial blood in the body region is the only time variant conductor in a compliant subject.

The parallel conductor model shown in FIG. 5 is composed of a constant admittance value ($Y_t$) that represents the composite parallel conductance characteristics of all the non-changing conductive pathways in the body region, and a pulsed changing value ($Y_{bv}$) that represents the pulsatile or time changing volume of arterial blood in the body region. $Y_t$ represents the total admittance value of all non-changing elements in the body region including fat, bone, lean tissue, extracellular fluid, intracellular fluid, and nonpulsatile blood volumes in the body region. $Y_{bv}$ represents the admittance of the variable arterial blood volume. This model is consistent with the simplified Nyboer formula (FIG. 4).

However, the parallel conductor model may also be expressed to show the total admittance of a body region by modeling each conductive element in the body region as parallel conductors:

$$Y_T = Y_{bv} + Y_{bc} + Y_{vc} + Y_{of} + Y_{tis} + Y_{bone} + Y_{fat} \text{ (admittance form)} \quad (6a)$$

Or the total impedance of the body region by parallel impedances:

$$1/Z_T = 1/Z_{bv} + 1/Z_{bc} + 1/Z_{vc} + 1/Z_{of} + 1/Z_{tis} + 1/Z_{bone} + 1/Z_{fat} \quad (6)$$

In a parallel impedance network in which the blood is a single element of a complex system of conductive elements, it would be valuable to be able to isolate the affects of the various impedance elements on the measured composite impedance value. Applicants do not believe that the known art has taught this valuable principle.

Photo-Plethysmography

Photo-Plethysmography is a known method of measuring the characteristics of blood and tissues by the amount of absorption of particular wavelengths of light. See for example U.S. Pat. No. 5,447,161 to Blazek et al, which combines venous occlusion and photo plethysmography techniques.

To applicants' knowledge, none of the aforementioned known art has recognized that information on the entire vascular system may be gained by combining plethysmography with the depletion or replenishment of body fluids under controlled conditions.

Upon gaining an understanding of the foregoing discussion, the person having ordinary skill in the art will appreciate that the circulatory system, in all its components, is connected, interactive, interdependent and largely unexplored or monitored outside of its large or pulsatile, or both, components, such as the heart and large veins and arteries. Therefore what is needed are means and methods for gathering physiologic data on each part of the circulatory system for gaining further knowledge of the operation of the circulatory system, including each vascular compartment or chamber or vessel type, including the large arteries, small arteries, arterioles, capillaries, venules, small veins and large veins. It is further desirable that such means be non-invasive, easily utilized and inexpensive when compared to the high cost of invasive techniques.

SUMMARY OF THE INVENTION

The present invention provides means and methods for gathering physiological parameters, or data, on each part of the circulatory system, thus affording opportunity for gaining further knowledge of the operation of the circulatory system, including each vascular compartment or body fluid chamber, or vessel type, including the large arteries, small arteries, arterioles, capillaries, venules, small veins, large veins and nonvascular fluids. It is the inventors' belief that as such means provide for increased knowledge of the parts and behavior of the circulatory system, other fluid compartments or physiologic data of significance may be identified. The present invention provides such means in a non-invasive manner which is easily utilized and is inexpensive when compared to the high cost of invasive techniques.

The present invention provides means and methods for noninvasively identifying the blood pressure characteristics in each of the seven types of vessels in the circulatory system, including the Central Venous Pressure (CVP), through a single monitoring system. According to certain aspects of the invention, a known pressure is applied to a body region in increasing amounts to force blood volume depletion from the body portion in step-wise fashion through each vessel type. Nonvascular fluid compartment parameters may also be identified. Fluid volume depletion, or replenishment, or both, for each compartment type is then tracked, or measured, in the pressurized area, e.g. by the increasing electrical impedance of the body part during depletion, or by other plethysmography techniques; and is plotted against the increasing pressure data. Pressure and volume data are then referenced against one another, such as by graphing or otherwise recording the data. Such a graph may be done virtually, e.g., mathematically, without the plotting of an actual curve. Release of the applied pressure may then yield similar data by measuring fluid volume replenishment, as indicated by decreasing impedance, against the decreasingly applied pressure during the same diagnostic session.

In the case of an actual graphing, the resulting series of slope changes witnessed within the plotted curve can be seen to reveal the characteristic blood pressure state in the range between each slope change, for each vessel type placed under depletion pressure. In the case of the virtual graphing, the apparatus may mathematically identify the points at which a coordinate linear, or curvilinear, relationship changes for the body fluid volume indications as referenced to the series of pressure values. That is, by detecting the change in the slope of the virtual graph, the state transitions, i.e. transitions from one pressure state to the next, are indicated in the vascular fluid profile between two adjacent vessel types (i.e. the transition points between vascular types).

The method is not dependent on oscillometric or pulsatile measurement methods. The measurement area for the volume sensor and the area of uniform pressure application to the body part are coextensive to ensure accurate indication of fluid volume depletion and replenishment and may be incorporated into a single integrated structure.

The present invention is not limited to the measurement of physiologic parameters in the large, and (to some minor extent) the small arteries. The present invention's lack of dependency on sensing the natural pulsations of the subject eliminates the time dependency on the occurrence of the naturally occurring pulsation for the measurement of physiologic parameters and allows for determination of physiologic parameters in fluid compartments that are non-pulsatile or oscillometric in nature. The present invention further reduces or eliminates the confounding signals of motion artifact and respiration in the acquisition and processing of the acquired physiologic data.

The present invention overcomes limitations of venous occlusion plethysmography to identify various physiologic properties of the subject in non-venous vessels of the body such as capillary vessels, arteriolar vessels, and nonvascular fluids. The present invention improves the capability of noninvasive pressure and volume measurement instruments to observe the characteristic physiologic behaviors of the fluid compartments of the subject during the depletion of fluid, during static fluid, and during replenishment of fluid, in each of the fluid compartments of the body region of the subject. Furthermore, the present invention is not limited to use on an appendage of the body of the subject but may be applied to any body region of the subject containing body fluid compartments.

Terminology

"Transition Points", "state transitions", and "state changes", are used synonymously to indicate a change from one pressure state (indicative of a particular fluid pressure and hence a particular vessel type according to aspects of the present invention) to a different pressure state.

"Known pressure value" as used herein includes known or measured values at the time of force application.

"Linear relationship" as used herein includes curvilinear relationships for ease and simplicity of explanation, unless otherwise noted.

"Graphing" as used herein includes any physical or virtual representation or construct referencing one type of value against another type of value, unless otherwise noted.

"Upstream" is used herein in the sense of an area of higher fluid pressure, while "downstream" indicates an area of lower fluid pressure.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION

Figure 1:
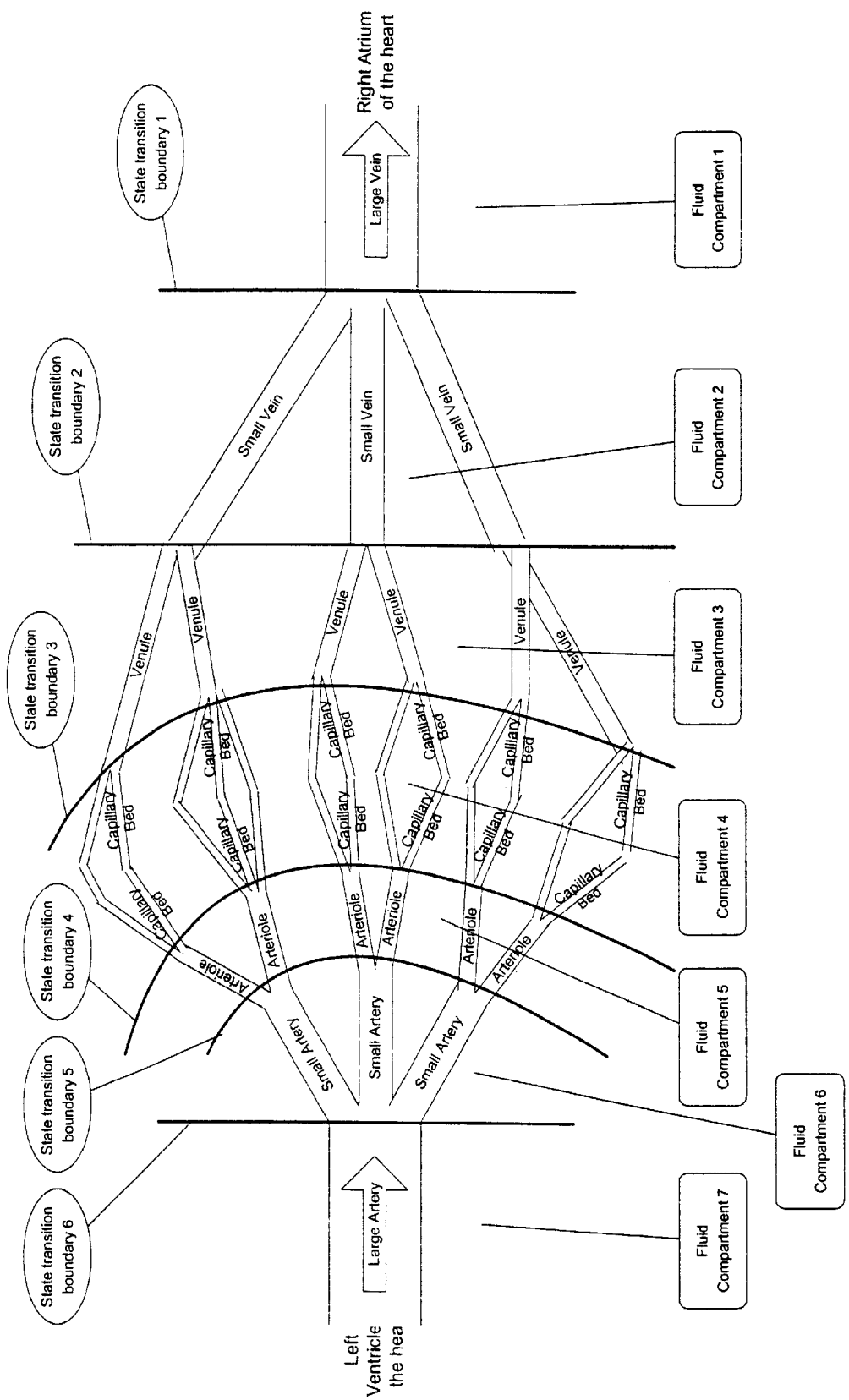
FIG. 1 is a schematic illustration of the vascular circuit and indicates the various fluid compartments and state transition boundaries.

It is commonly known that transport of fluids within the body of a subject is accomplished by the cardiovascular system, as illustrated in FIG. 1. The propulsion of fluids through the cardiovascular system is accomplished by pulsatile pressurization of a network of blood vessels by the periodic contraction of the heart. Table 1 summarizes the functional characteristics of various vessel types comprising the vascular bed of the cardiovascular system.

TABLE 1

| | Summary | | | |
| --- | --- | --- | --- | --- |
| | Pressure | Resistance | Nature | Function |
| Aorta & Large arteries | High | Low | Elastic | Energy storage |
| Arterioles | Major drop | High | Muscular | Distribution/control |
| Capillary | Further drop | Low | Permeable | Exchange with tissues |
| Venules and small veins | Low | Low | Contractile | Variable reservoir |
| Large Veins | Low | Low | Capacious | Return blood to heart |

Vessel Functions

As shown in FIG. 1, blood vessels progressively branch, or diverge, into smaller and smaller vessels along the flow of blood from the heart to the capillary beds and progressively branch, or converge, into larger and larger vessels as the blood flows back to the heart through the veins.

Figure 2:
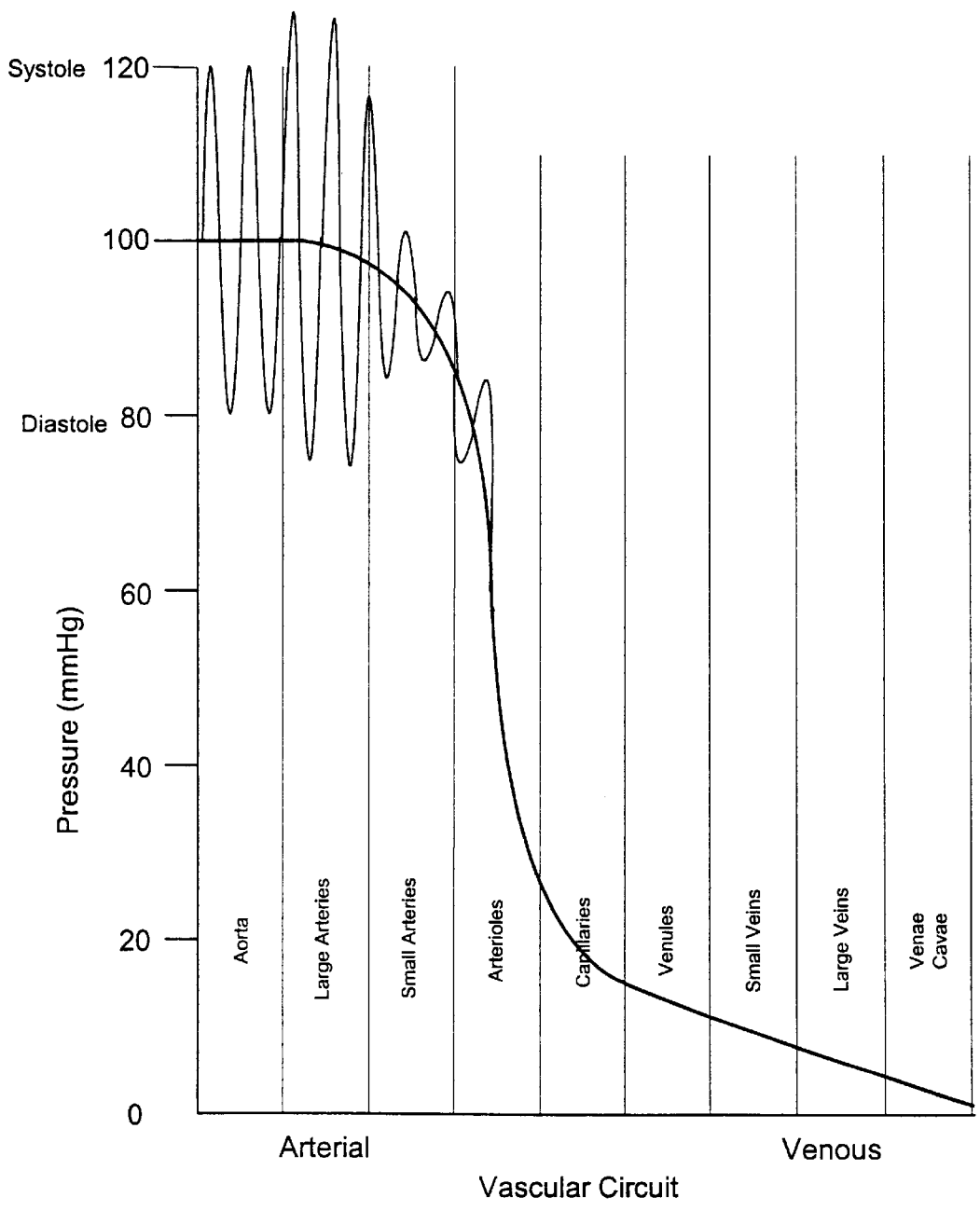
FIG. 2 is a schematic graph illustrating pressure variation as a function of anatomic location in the vascular circuit.
Figure 3:
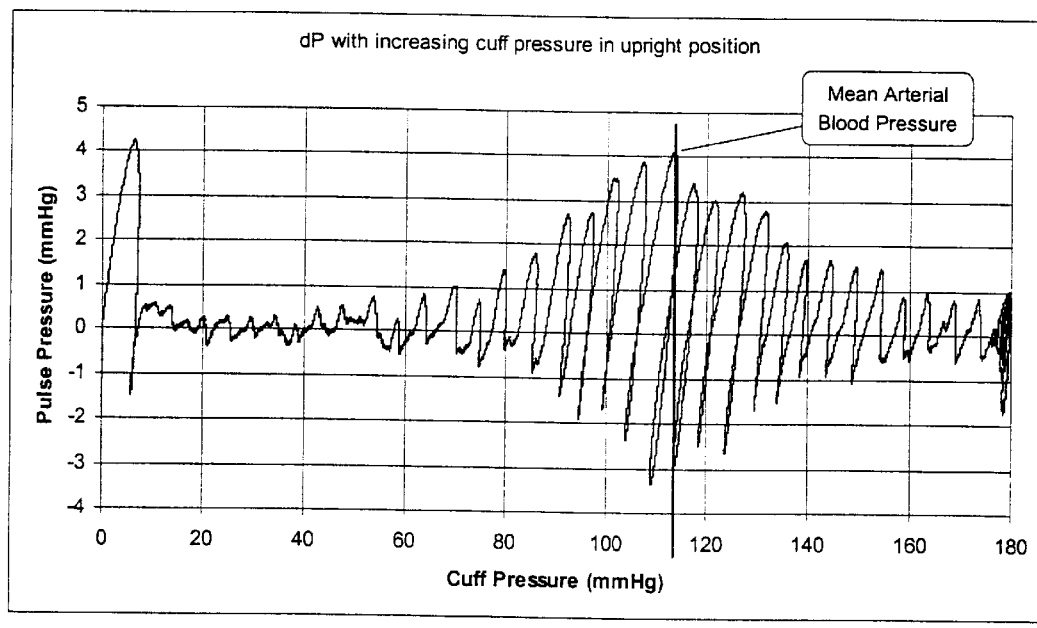
FIG. 3 illustrates a known curve of "oscillometric" pressure versus pressure and time.

FIG. 2 illustrates schematically the anatomic network of vessels organized by the progression of vessel types, sometimes inclusively referred to herein under the more generic term "anatomic fluid compartments", along the horizontal axis versus the typical pressure characteristics that exist within each vessel type in the body of a subject. As blood flows through the systemic circuit from the heart through the arteries, the capillaries, and the veins, the pressure of the blood declines a characteristic amount in each of the vessel types.

It is also shown in FIG. 2 that the pressure pulsations which are prominent in the large arteries are substantially reduced as the blood flows through the small arteries into the arterioles. Note that the blood pressure typically drops precipitously in the arterioles and there are no appreciable pulsations present in the blood flowing through the capillary beds and veins. It is evident from FIGS. 1 and 2 that the pressure characteristic of each vessel type is unique in relation to other vessel types and therefore a unique pressure state or identity exists for each vessel type in the vascular network. Furthermore, this characteristic of "pressure identity" in the various vessel types in the vascular network may also apply to nonvascular fluid compartments within the subject.

It can also be observed in FIG. 1 that a physical change occurs between each vessel type due to the divergence or convergence of vessels as they transition from one vessel type to another. The physical size or volume capacity of the individual vessel types (volume), the compliance attributes of the vessel wall of the individual vessel types, and the characteristic divergence or convergence at the interface between different vessel types all contribute to establishing a unique state identity of individual vessel types versus pressure. The inventors have observed that each vessel type also has a unique bulk, or steady-state, fluid volume identity.

One important element of certain aspects of the present invention is the identification of the characteristic pressure states, or identities, for each vessel type, and the state transition boundaries that exist between fluid compartments of the subject. The present invention makes use of the volume and pressure state transitions to identify the characteristic pressures P(i) (see e.g., FIG. 7) for fluid compartments in the subject from pressure and volume data acquired noninvasively from the body region of a subject. It will further be appreciated upon a thorough understanding of the present invention that many physical attributes that change as a function of pressure may be observed for the purpose of identifying their pressure state identities and pressure state transition boundaries in the body of the subject. It is the identification of the unique state transition boundaries for each fluid compartment which allows for determination of physiologic parameters associated with each fluid compartment from further analysis of the acquired data. Thus, it will be appreciated that the invention is not necessarily limited to gathering of physiologic blood data as set forth in the detailed discussion for the present purposes of explanation and example.

Figure 6:
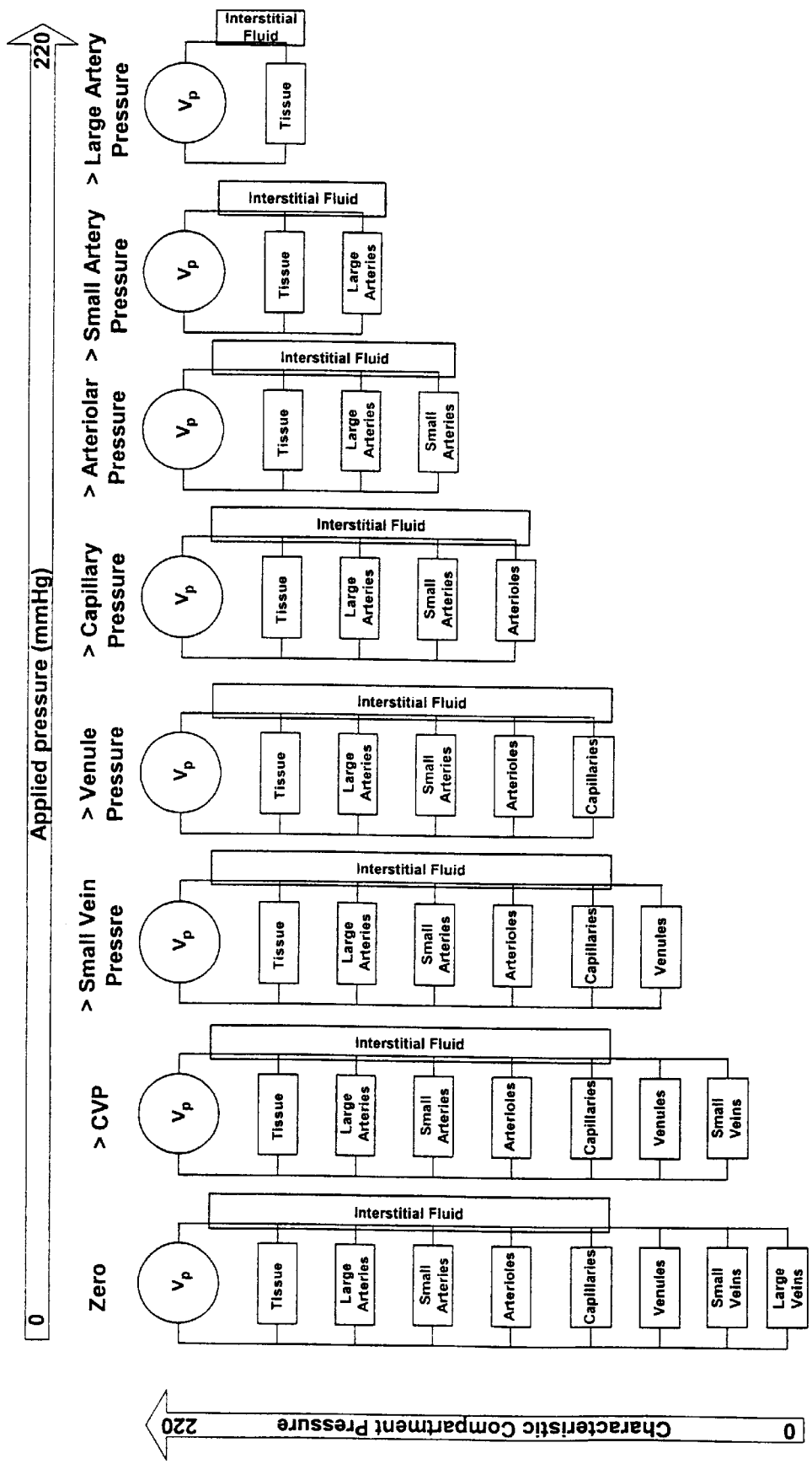
FIG. 6 is a schematic diagram of the equivalent parallel volumes of a segment of a body region of a subject and how they change with increasing applied pressure.

Certain aspects of the present invention introduce a new method of measuring physiologic parameters from a subject based upon fluid volume depletion and fluid volume replenishment in a body region of the subject. FIG. 6 illustrates the relationship of fluid volume versus pressure in the body region of a subject as a system of parallel volumes organized as progressive fluid compartments with individual characteristic compartment pressures. As the applied pressure is increased against a body region of the subject, the pressurized fluid compartments are depleted of fluid volume in a sequential manner based upon the characteristic pressures of each fluid compartment.

The inventors call the relationship between applied pressure and volume depletion or volume replenishment of fluid compartments in the subject the "weakest link principle of pressure and volume in fluid compartments of the subject". As pressure is increased against the body region of the subject, the first fluid compartment to begin depleting fluid will be the one with the lowest characteristic pressure. Since anatomic fluid compartments have progressively different pressure characteristics as shown in FIG. 2, increasing the applied pressure will progressively deplete different fluid compartments at different pressure or pressure ranges.

FIG. 6 relates the volume characteristics of anatomic fluid compartments to the pressure characteristics of anatomic fluid compartments illustrated in FIG. 2. The depletion process is reversed as the applied pressure is reduced, with the fluid in each chamber being replenished according to the characteristic pressures of each fluid compartment. FIG. 6 shows how each fluid compartment in the body region represents a different fluid volume versus pressure characteristic and how the volume/pressure state transition from one fluid compartment to the next is indicative of the physiologic attributes associated with each fluid compartment.

Among the advantages of this method is the fact that it allows for measurement of both non-pulsatile (time invariant) and pulsatile (time variant) physiologic data either separately or jointly from the subject. Noninvasive measurement of non-pulsatile physiologic data allows for determination of "residual" or "static" fluid volumes within the fluid compartments of the subject and removes the dependency on naturally occurring pulsatile or time variant physiologic events in order to noninvasively measure physiologic parameters. Therefore, the present invention does not depend on naturally occurring pulsations or oscillations within the arteries of the subject for the measurement of physiologic parameters and is not limited to the determination of physiologic parameters for such vessels.

Figure 7:
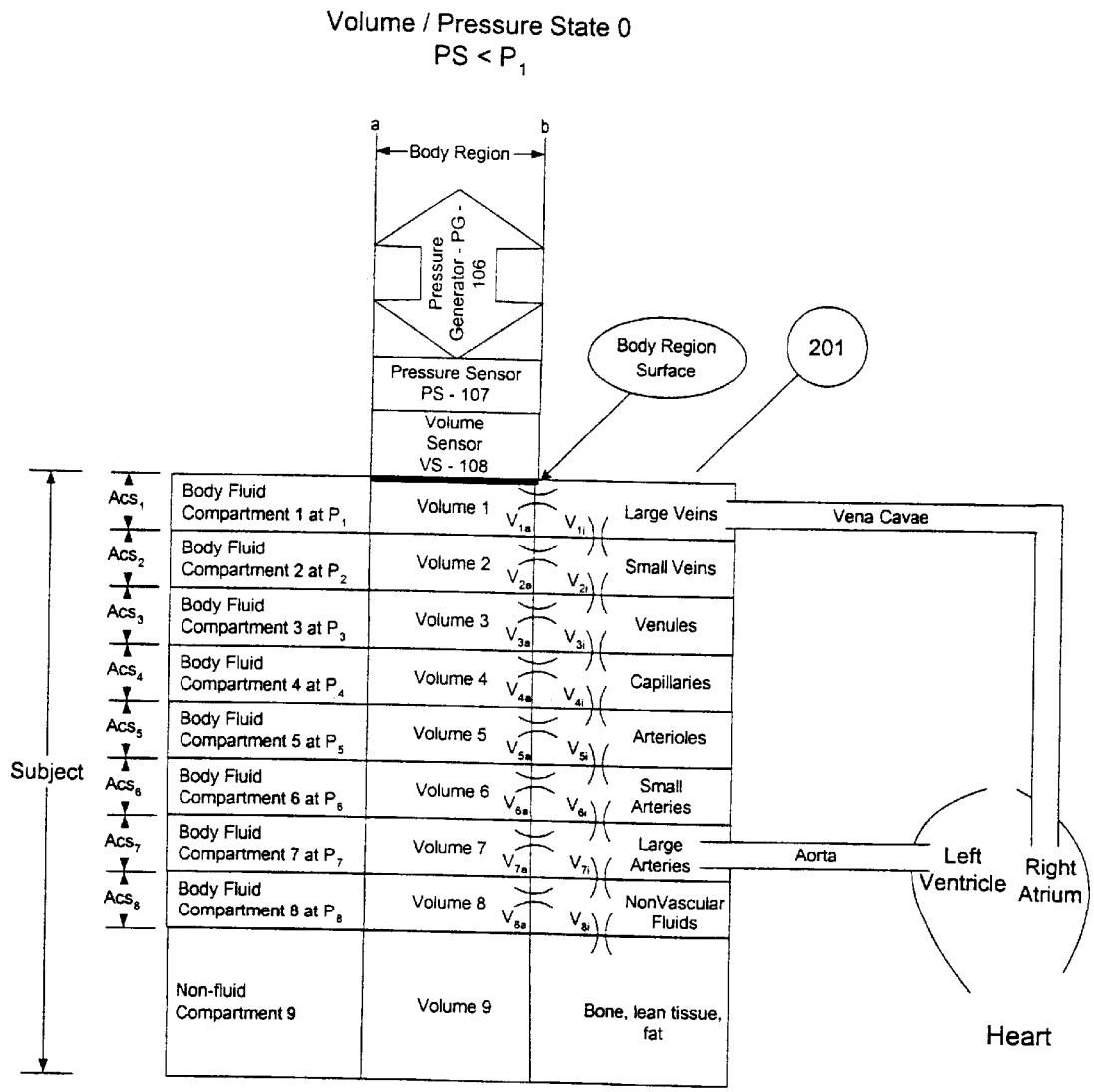
FIG. 7 is a schematic representation of the subject's various fluid compartments and illustrating the Pressure Generator, the Pressure Sensor and the Volume Sensor.

FIG. 7 illustrates a body region 201 of a subject. Generally, in any blood perfused body region, the body may be said to have eight independent but interrelated and interconnected body fluid compartments and one non-fluid compartment, holding Volumes 1–9. Eight body fluid compartments are shown for the purpose of illustration of the invention, however, it is anticipated by the inventors that there may be more or less than eight body fluid compartments in a body region of a subject. FIG. 7 illustrates fluid compartments 1 through 7 as vascular fluid compartments, compartment 8 as a non-vascular fluid compartment, and compartment 9 as a non-fluid compartment.

Body fluid compartments can be defined by a set of physiologic attributes, giving the compartment a unique physiologic identity, such as pressure, volume, fluid flow velocity, cross sectional area ($A_{cs}$), fluid composition, cell wall attributes, and vessel wall attributes. Since physiologic functions are often dependent on pressure to effect transport of substances within the body of the subject, each fluid compartment is identifiable by its internal characteristic pressure or pressure range ($P_i$), the volume of the compartment, and its inter-compartmental valve ($V_{1i-8i}$) or intra-compartmental valve ($V_{1a-8a}$) characteristics as shown in FIG. 7. It will be appreciated that valve characteristics, as used herein, are not dependant upon an actual separately identifiable valve structure. Inter-compartmental valves allow fluid to flow from one fluid compartment to another fluid compartment. A body fluid compartment may also be connected to itself by an intra-compartmental valve as illustrated by $V_{1a}$ through $V_{8a}$ of FIG. 7. The intra-compartmental valve allows the fluid within the compartment and within the body region to flow within the same fluid compartment in an adjacent body region.

"Valves" as used herein may be elements of the fluid compartments offering control of fluid flow into or out of the fluid compartment within the body region either as a continuous or discontinuous function of pressure. Furthermore, valves may vary significantly in functional characteristics between different fluid compartments within the body region of a subject and between similar fluid compartments from one subject to another subject. An example of an inter-compartmental valve might be the divergence or convergence of different vessel types in the vascular network of FIG. 1. An example of an intra-compartmental valve is a lower pressure fluid compartment that has been compressed by an applied pressure greater than the natural pressure of the compartment within the body region of the subject.

The pressure parameter ($P_i$) associated with a body fluid compartment in its natural state may be a single pressure value or a range of pressure values that can define the identity of the fluid compartment. It is further anticipated by the inventors that body fluid compartments may have pressure characteristics which overlap, are sequential, or are separated by a pressure difference.

FIGS. 8 and 14–21 schematically illustrate an exemplary device for noninvasive measurement of physiologic parameters from a body region of a subject using detection of fluid volume depletion and fluid volume replenishment according to the present invention.

Figure 8:
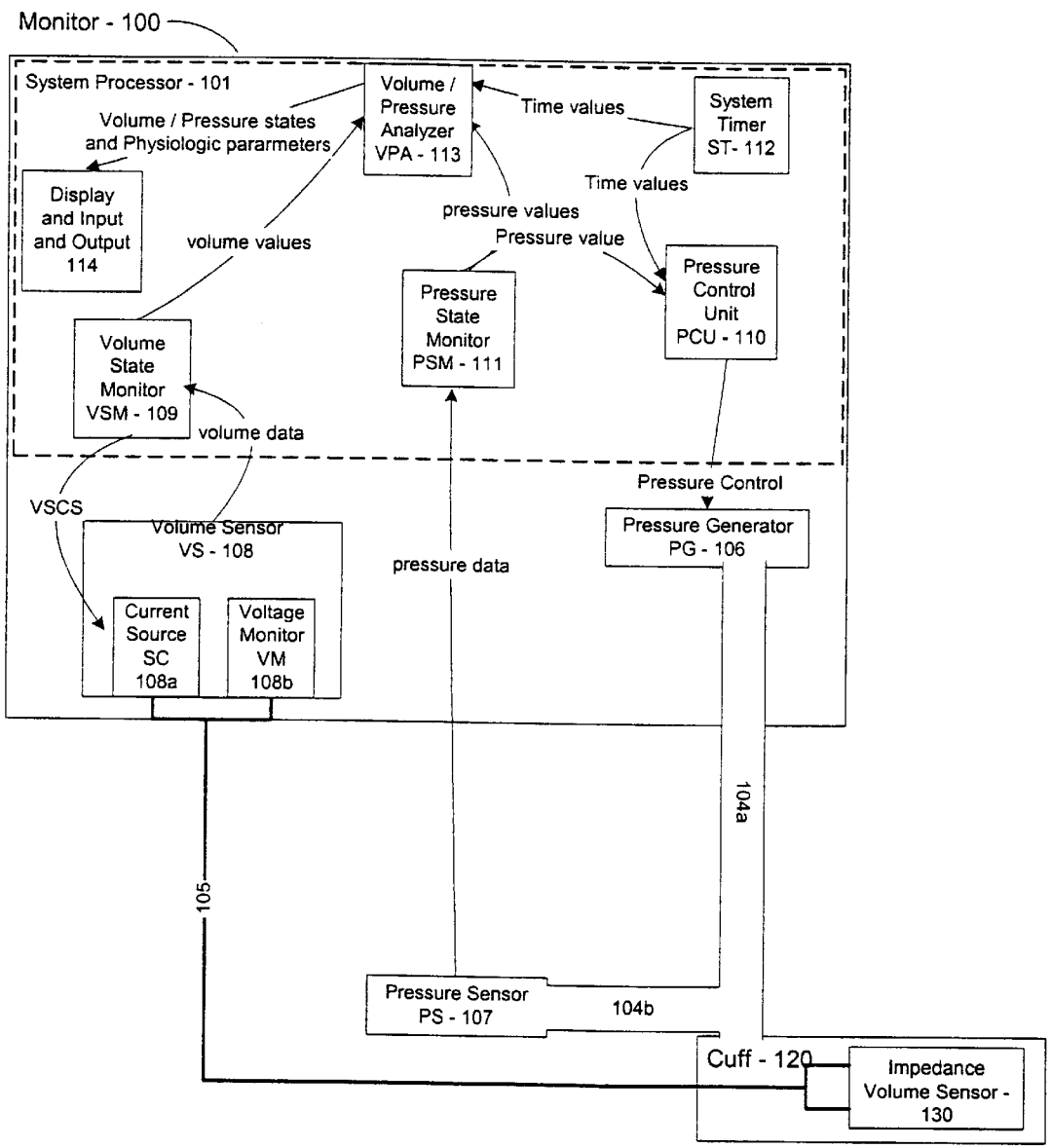
FIG. 8 is a block diagram of one aspect of the present invention with a pressure sensor, an inflatable cuff pressure generator and a bioimpedance fluid volume sensor.

As illustrated in FIG. 8, the invention can be comprised of a pressure generator (PG)(106), a pressure sensor (PS)(107), a volume sensor (VS)(108) a pressure control unit (PCU) (110), a pressure state monitor (PSM)(111), a system timer (ST)(112), a volume state monitor (VSM)(109), a volume/pressure analyzer (VPA)(113), a display or input/output system (114) for operator interface, and data lines, represented by arrows, between them.

Figure 9:
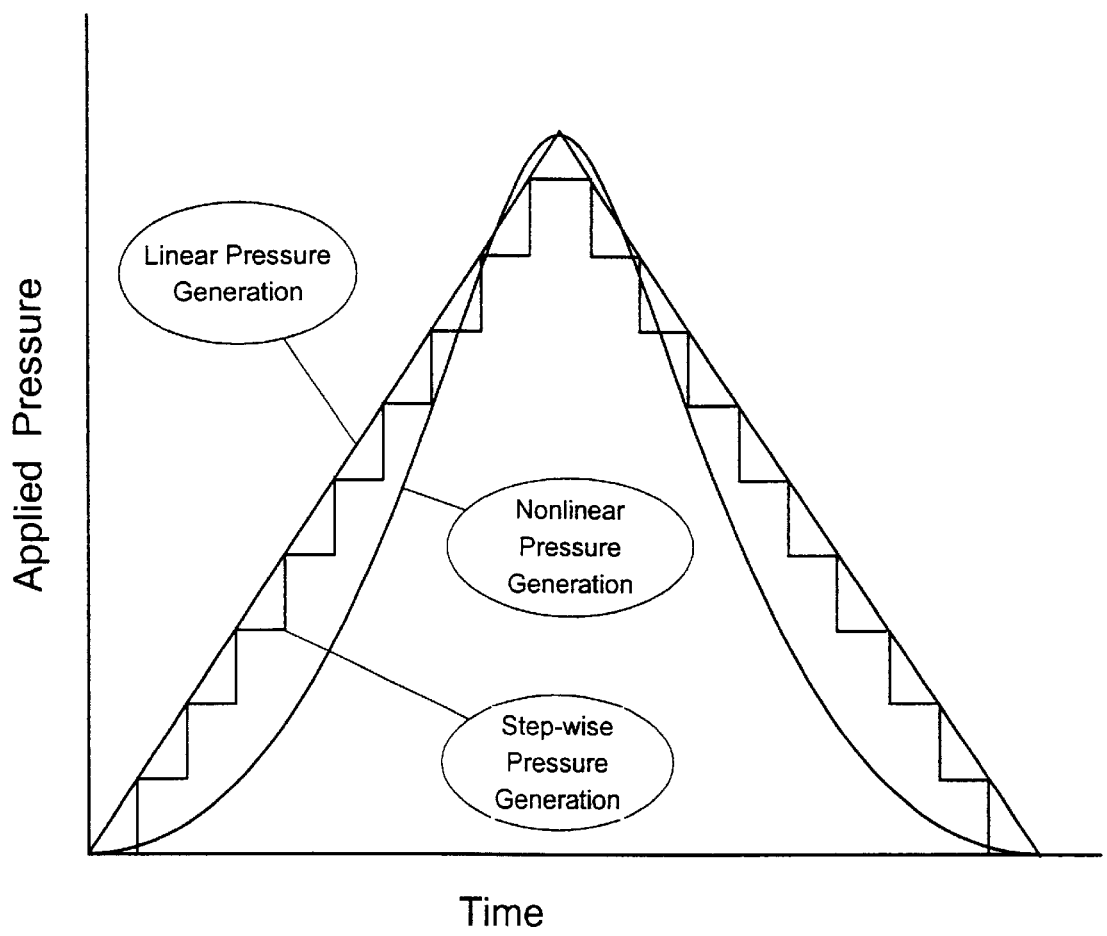
FIG. 9 is a schematic presentation of profiles of pressure generation and application.

In FIG. 8 the pressure signal from the pressure sensor 107 is applied to the pressure state monitor 111. The pressure state monitor 111 (see also FIG. 17) calibrates the pressure signal from the pressure sensor 107 for use by the pressure control unit 110 (see also FIG. 18) and the volume/pressure analyzer 113, (see also FIG. 21). The pressure control unit 110 produces pressure control signals for the pressure generator 106 for controlling the rate and direction of pressure change against the body region 201. The pressure control unit 110 also controls the limits of pressure that is applied to the body region of the subject. The pressure generator 106 may apply or relieve pressure against the body region 201 in a linear, nonlinear, or step-wise manner over time as shown in FIG. 9.

It is advantageous to measure some physiologic parameters by a method of pressure generation comprised of a steadily increasing pressure starting from an applied pressure that is less than the lowest pressure in a fluid compartment and elevating to a pressure greater than the highest pressure in a fluid compartment of the subject. This method permits detection of Volume/Pressure state transitions in the body region while the body region fluid compartments are in their natural unmodified state. It is advantageous to measure other physiologic parameters by methods of pressure generation comprised of a steadily decreasing pressure versus time or a step change in pressure starting from a higher applied pressure and decreasing to a lower applied pressure. These methods may permit detection of time dependent volume/pressure state transitions in the body region after the body region fluid compartment has been depleted and while the fluid compartment is replenishing to its natural state. It is advantageous to observe volume and pressure state changes in response to step changes in applied pressure for both increasing pressure steps and decreasing pressure steps when determining volume replenishment time intervals as well as steady state volume of a fluid compartment at a particular body region pressure.

The volume sensor 108 produces volume data including any data indicative of volume or volume changes in the body region of the subject. Therefore, the volume sensor 108 may measure absolute, calibrated, relative, or proportional volume data from the body region. The volume state monitor 109 receives volume data from the volume sensor 108 and processes the volume data into volume values. The volume state monitor 109 also produces volume sensor control signals VSCS for stimulating and controlling the volume sensor 108. Volume values may also be absolute, calibrated, relative, or proportional to actual volumes of the subject for determination of volume/pressure state transitions by the Volume/Pressure Analyzer 113. The volume sensor 108 and volume state monitor 109 may, in combination, perform volume value determinations using any method of noninvasive detection of volume or volume changes in a body region. This includes but is not limited to methods of bioimpedance (as illustrated), ultrasound, optical absorption, optical diffusion, optical reflection, all forms of electromagnetic energy absorption, magnetic resonance, piezoelectric, tonometric, and mechanical displacement.

As further seen in FIGS. 17–21, the volume pressure analyzer 113 may acquire volume values from the volume state monitor 109 while the pressure generator is increasing pressure against the body region in a linear, non-linear, or step wise manner, or while the pressure generator is holding pressure constant against the body region, or while the pressure generator is decreasing pressure against the body region in a linear, nonlinear, or step-wise manner. The volume pressure analyzer 113 receives concurrent volume values and pressure values for analysis and presentation, as illustrated by the data flow arrows. The volume pressure analyzer 113 analyzes the volume values versus pressure values or time values and determines the occurrence of volume/pressure or volume/time state transitions and the specific pressure value or time value at which the volume state transition occurs. Furthermore, the volume pressure analyzer 113 determines the range of pressures over which a particular volume/pressure state exists. It is important to note that volume changes over time are only indicative of volume state transitions if there is a pressure generator which is changing the applied pressure against the body region over time. Therefore, the fundamental relationship that is indicative of volume/pressure state transitions is the volume changes during pressure changes. It is anticipated by the inventors that any combination of parameters for determination of volume/pressure state transitions to characterize adjacent compartments in or around the vascular system is within the spirit of the present invention.

It is noted that a volume state may be defined by any state variable or group of state variables including, but not limited to, the rate of change in volume versus time, the rate of change in volume versus pressure, the rate of change of pressure versus volume, the rate of change of pressure versus time, the rate of change of a volume-indicating parameter versus pressure, the rate of change of a volume-indicating parameter versus time, the rate of change of a pressure-indicating parameter versus time, and the rate of change of a pressure-indicating parameter versus volume.

The Pressure Generator (PG) 106 (see also FIG. 16) may include any means and method for applying and relieving pressure to a body region of a subject in a controlled manner. The pressure generator 106 may be capable of applying increasing or decreasing pressure at a linear, nonlinear, or step-wise rate of change of pressure versus time as shown in FIG. 9. Furthermore, the pressure generator 106 can be capable of holding pressure at a pressure level for a period of time, or dithering above and below a pressure level over a period of time. The present invention concurrently measures the pressure applied to the body region with the pressure sensor (PS)(107), and the volume state of the body region with the volume sensor 108.

Figure 10:
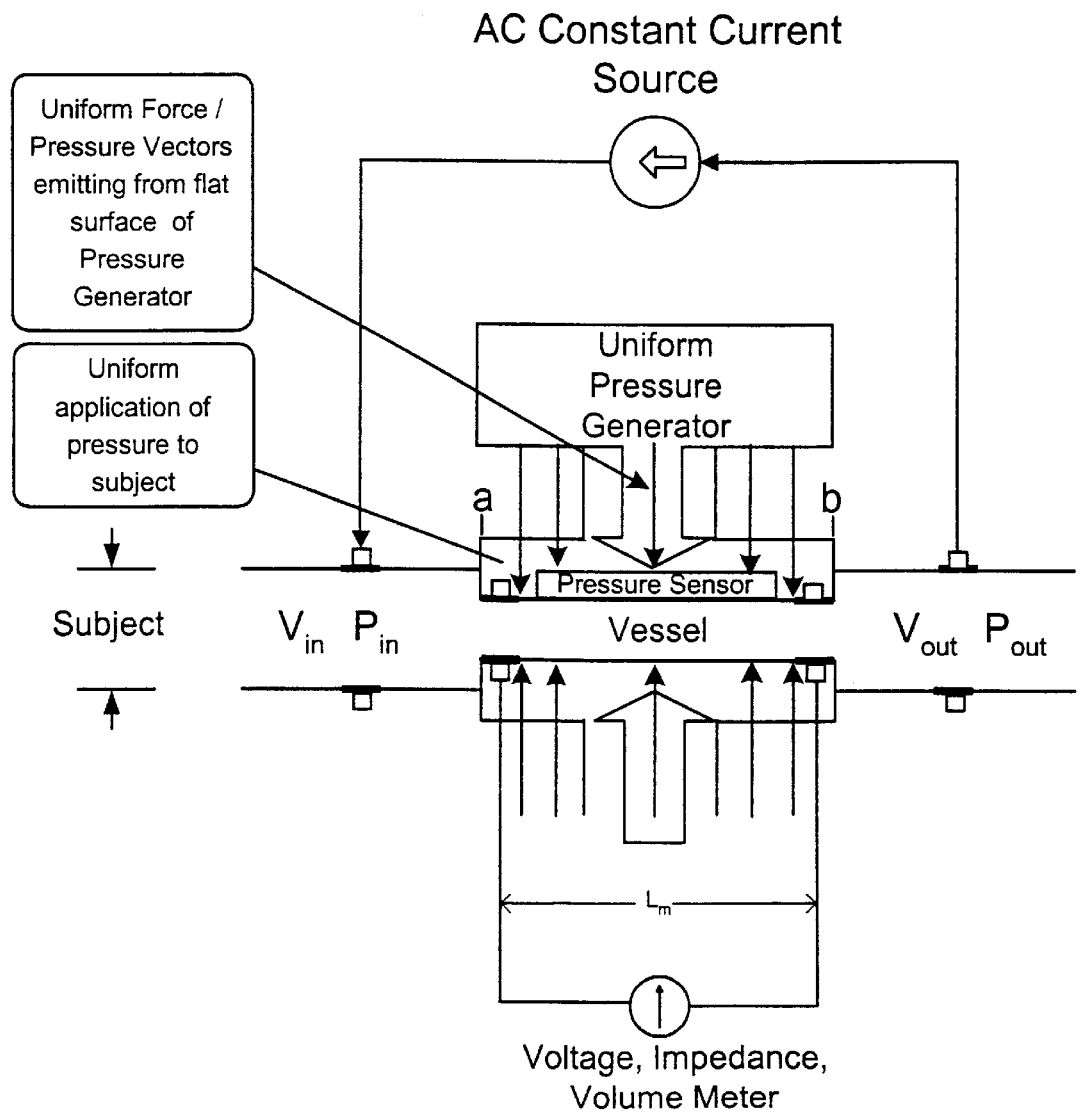
FIGS. 10 and 11 depict the effects of uniform and non-uniform pressure application respectively.
Figure 11:
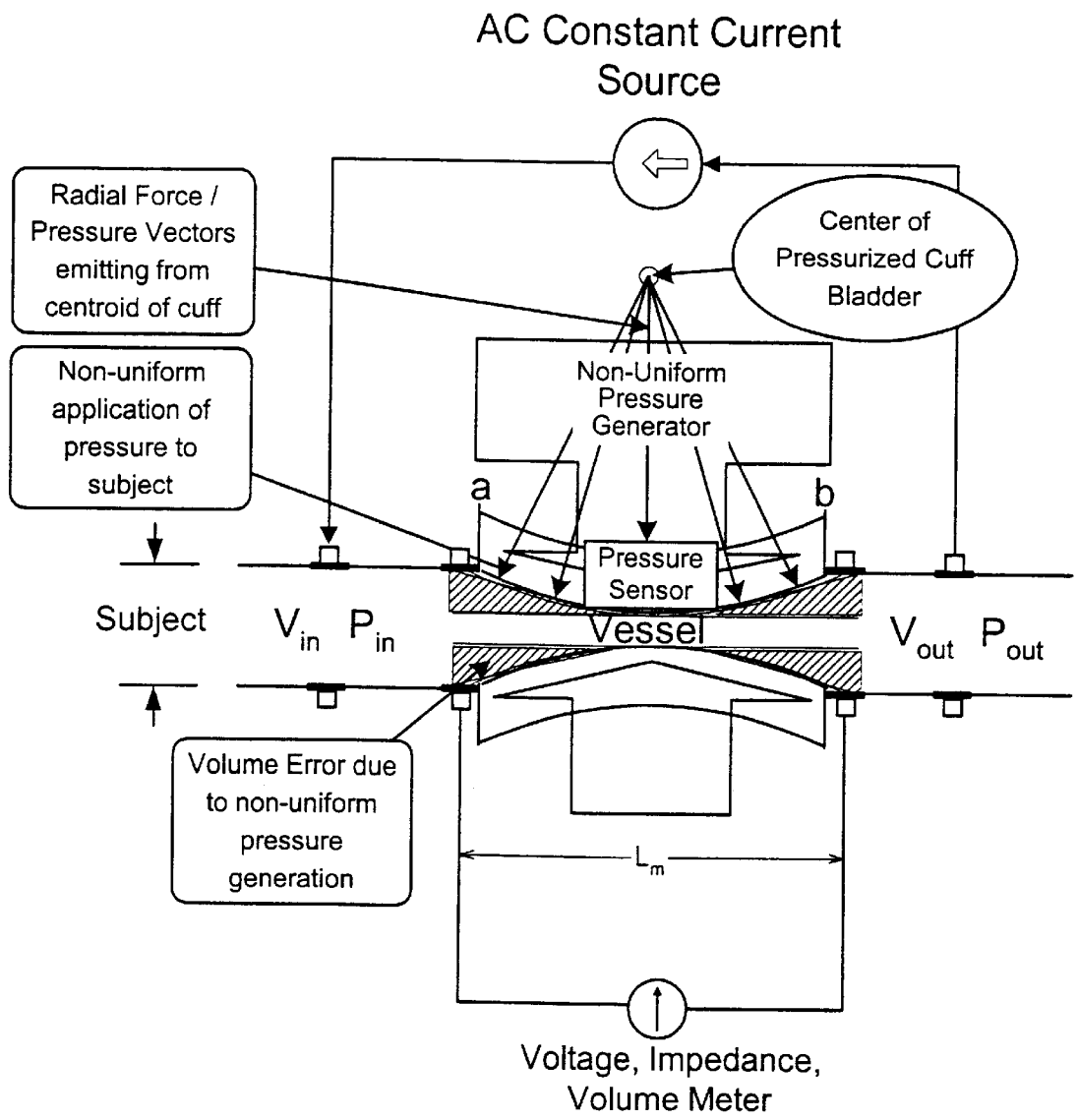

It is important to note that state transition boundaries between fluid compartment types can be identified from the volume depletion and replenishment data acquired from the body region of the subject when there is either uniform or non-uniform pressure generation against the body region of the subject. FIG. 10 shows a uniform pressure generation and FIG. 11 shows a non-uniform pressure generation. A common inflatable blood pressure cuff produces the type of pressure generation shown in FIG. 11. It can be seen in FIG. 10 that uniform pressure generation within the body region a–b will generate precise and accurate state transitions between compartments at the pressures defined by one fluid compartment in the region a–b because the volume of that fluid compartment goes to zero when the applied pressure exceeds the pressure of the fluid compartment.

It can be seen from FIG. 11 that non-uniform pressure generation within the boundaries of the volume measurement region a–b will generate less precise and accurate state transitions at the applied pressure because the fluid volume in the body region will not be fully depleted from the body region when the applied pressure equals the pressure of the fluid compartment. The affect of non-uniform pressure application in the region of volume measurement will be to move volume/pressure state transitions from the pressure value associated with the fluid compartment to a higher pressure value. However in either case, the relationship of pressure generation to volume measurement is an important new contribution to the art of noninvasive physiologic monitoring. Furthermore, volume depletion and volume replenishment data for fluid compartments is an important contribution to the art of noninvasive physiologic monitoring that allows for the determination of physiologic parameters beyond fluid pulsatile and occluded compartment volumes, such as venuole, CVP, capillary, and arteriolar pressures, which have not been previously measurable by noninvasive methods.

Inflatable cuffs have been extensively used in various forms of physiologic monitoring such as noninvasive blood pressure, pulse volume recording, and peripheral vascular analysis. Inflatable cuffs have been used in combination with other physiologic sensing means such as bioimpedance sensors as disclosed by Shankar (U.S. Pat. No. 5,241,963). However, the relationship between the co-extensive inflatable cuff and the bioimpedance sensor for accurate and reliable sensing of physiologic parameters as disclosed herein, has never been disclosed. The inflatable cuff is intended to provide a controlled pressure to a limb of the subject. Conventional blood pressure cuffs have a single inflatable bladder.

It has been shown in multiple studies from 1970 to present time that there exists an adverse relationship between the width of the inflatable cuff and the accuracy and reliability of the blood pressures determined by its use on a varied population of subjects. In a January–March, 1976 publication of the Cardiovascular Research Center Bulletin titled: "The Importance of Cuff Width in Measurement of Blood Pressure Indirectly," Geddes and Tivey state "It is thus well documented that use of an excessively narrow cuff overestimates blood pressure and the use of an excessively wide cuff underestimates blood pressure." Although this adverse relationship has been understood from observation of experimental data, an explanation of the mechanism responsible for this error has never been disclosed.

FIGS. 10 and 11 help illustrate the difference between uniform pressure generation and non-uniform pressure generation. In FIG. 10, the uniform pressure generator applies uniform pressure to the subject and causes a uniform deformation of the fluid compartments in the body region a–b. In FIG. 11, the non-uniform pressure generator causes a non-uniform deformation of the fluid compartments in the body region a–b of the subject. A conventional blood pressure cuff generates pressure against the body region of the subject non-uniformly. The inflatable cuff expands when it is inflated changing shape from a flat geometry to a round geometry. The outer layer of the inflatable cuff is relatively non-compliant and therefore, the majority of the volume displacement of the cuff, as it is inflated, displaces volume in the body region of the subject. The physical displacement of volume functions according to gas laws when a gas such as air is used for inflation of the cuff and liquid density laws when a liquid is used to inflate the cuff. In either case, the cuff geometry changes with inflation from a flat somewhat rectangular geometry to a round somewhat oval geometry due to the volume displacement of the cuff. The pressure produced within the cuff and measured by the pressure sensor is physically relative to the center of the cuff and produces force vectors outward from the centroid of the cuff bladder in every direction as shown in FIG. 11. Since the cuff changes geometric shape with inflation, the pressure gradient experienced by the body region of the subject is a geometry reflective of the force vectors produced by the cuff as shown in FIG. 11. It can be seen in FIG. 11 that this non-uniform pressure generation produces a non-uniform deformation of the fluid compartments in the body region a–b of the subject. This non-uniform deformation of the fluid compartments can be the direct cause of errors in current noninvasive blood pressure monitoring practices.

Figure 12:
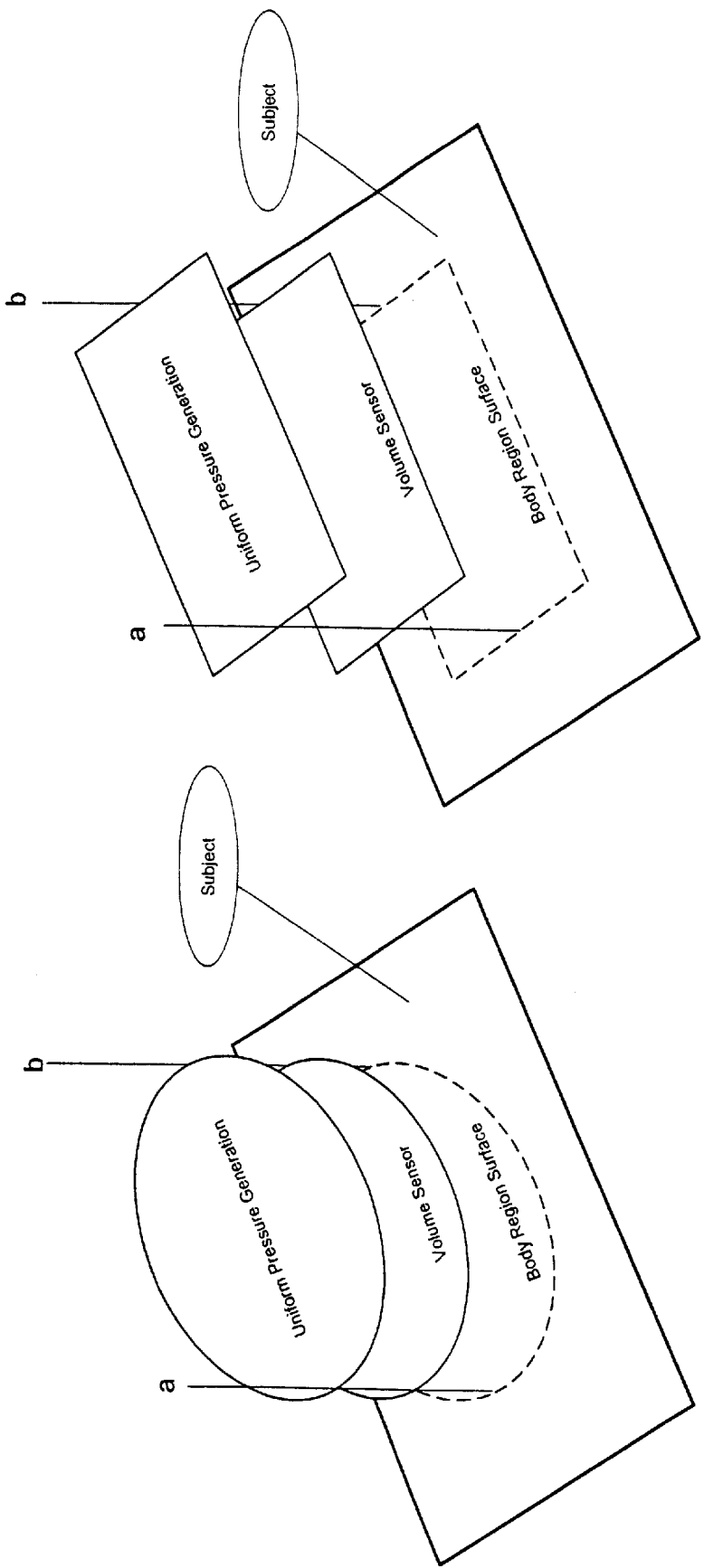
FIG. 12 depicts examples of body region surface coextensivity for the volume sensor together with uniform pressure generation.

Conventional noninvasive blood pressure monitors measure the cuff pressure and the change in cuff pressure caused by the propagating pressure wave in the artery of the subject, as previously explained. Such monitors then seek to relate the observation of specific states of pulsatile pressure to the applied pressure. Non-uniform pressure generation will thus cause the indicative pulse pressure state to present at a different applied pressure than what is anticipated by the pulse pressure state analysis algorithm. Therefore, any method of pressure generation producing uniform pressure to the body region of the subject may be an improvement over current methods of pressure generation. For more accurate measurement of volume depletion, volume replenishment, and volume/pressure state transitions it is desirable to have a co-extensive uniform pressure generation and volume sensing of the body region subject to the uniform pressure, as shown in FIG. 12.

Figure 13:
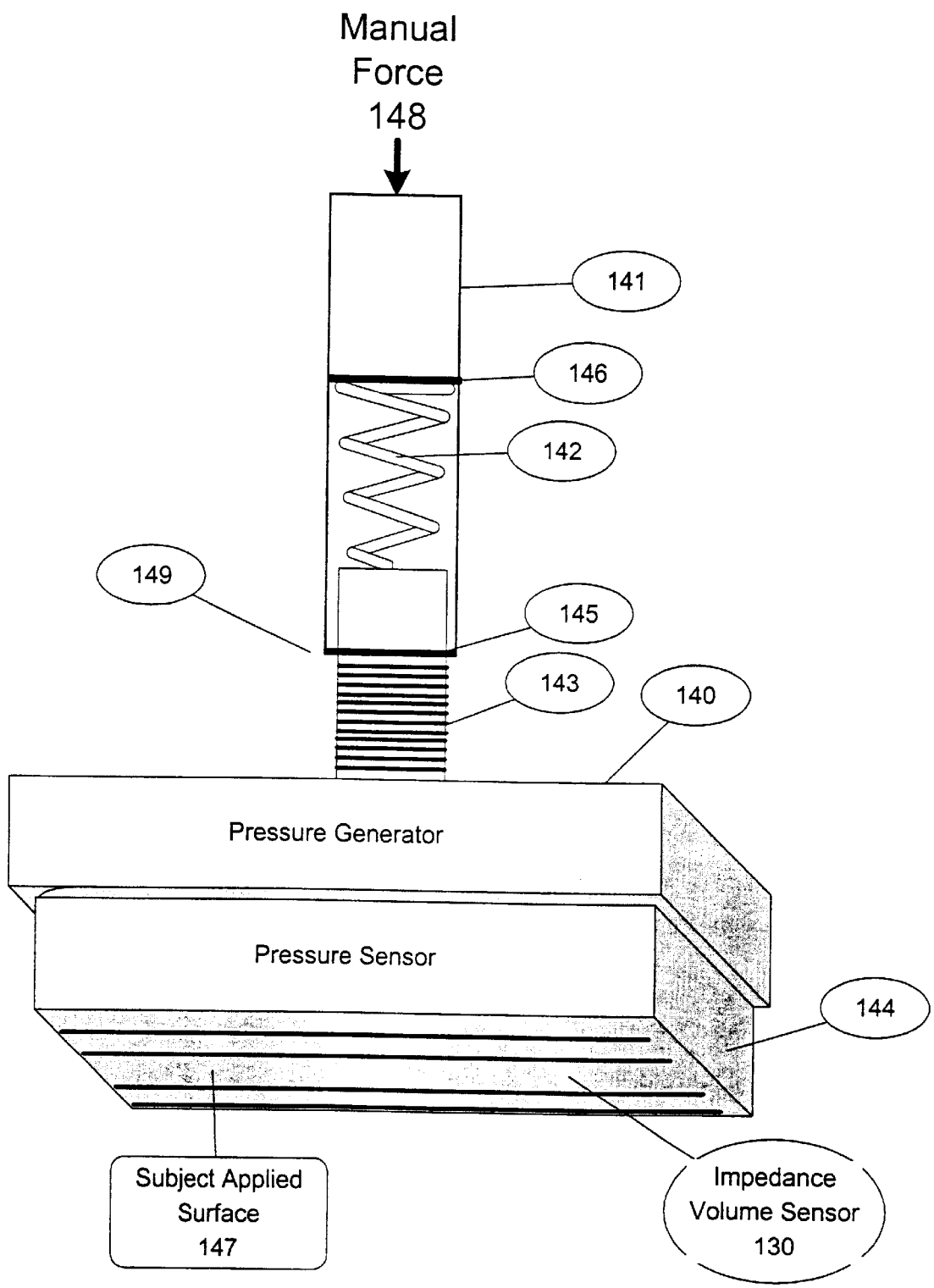
FIG. 13 is an illustration of an embodiment of a pressure applicator and volume sensor apparatus that is not limited to surrounding a limb of the subject.

Uniform pressure generation can be produced in multiple ways. One exemplary way is demonstrated in FIG. 13 and may be utilized without the need to surround an appendage of the body. The embodiment of FIG. 13 employs a flat rigid surface 147 to be forced against the body region of the subject by manual assertion 148, although it will be appreciated that the illustrated aspect may be automated. A calibrated spring 142 is included to partially oppose the manual force 148 applied to the operator handle 141 to even out the application of force. The calibrated spring 142 is held in place between the handle 141 and a shaft 149 by an upper stop 146 and a lower stop 145. The handle 141 is movable in the axis of the shaft 149. The calibrated spring 142 opposes the movement of the handle in relation to the shaft 149. The shaft 149 is affixed to the back of a pressure generator body 140. The pressure sensor 144 is fixed to the pressure generator body 140 and centered on the shaft 149. The impedance volume sensor 130, is applied to the subject applied surface 147 of the pressure sensor 144 and may be removably affixed thereto.

Figure 14:
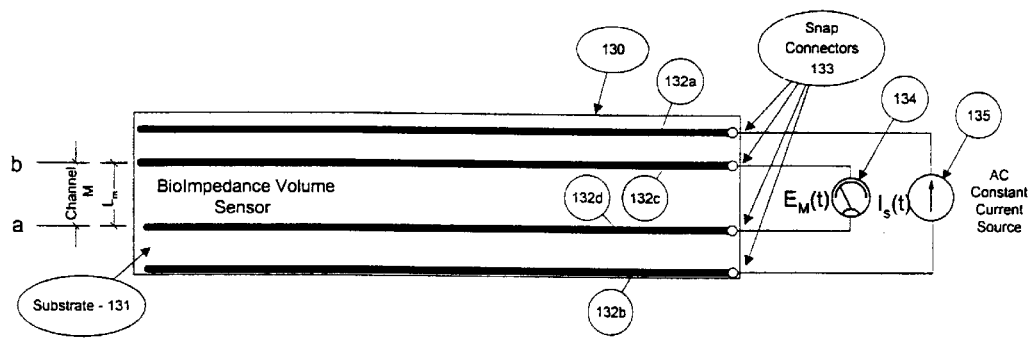
FIGS. 14 and 15 illustrate apparatus for the Cuff and Impedance Volume Sensor blocks shown in the block diagram of FIG. 8.

For normal use, a force 148 is applied to the handle 141 pressing the combination of pressure generator 140, pressure sensor 144 and impedance volume sensor 130 against the body region of the subject until a desired pressure level 143 has been achieved. The force 148 is then relieved and the measurement cycle is complete. The monitor interface to the FIG. 13 embodiment can be the same as the first exemplary embodiment as shown in FIG. 8 except the pressure generator 106, cuff 120, and hoses 104a and 104b will not exist. Volume Sensor 130 may be a bioimpedance volume sensor comprised of a matrix of four or more parallel conductive lines fixed to a flexible substrate material, e.g. Mylar, with snap connectors on one end of each line as shown in FIG. 14, i.e., similar to the cuff arrangement previously discussed. All of the considerations of positioning and electrode spacing described in that embodiment apply equally. Therefore other than the excluded parts of the pressure generator, the Monitor 100 as shown in FIG. 8 will meet interface and data processing requirements of the FIG. 13 exemplary embodiment of the invention.

An alternative form of uniform pressure generator is a device composed of relatively low extensibility material to be drawn around a limb or appendage of the subject. A device demonstrating uniform pressure generation capability has been disclosed in U.S. Pat. No. 5,351,694. However, the relationship between pressure generation and blood pressure accuracy within the context of the present invention was not disclosed. Nor was there any disclosure in this patent relating fluid volumes and pressures for physiologic parameter measurement.

Figure 15:
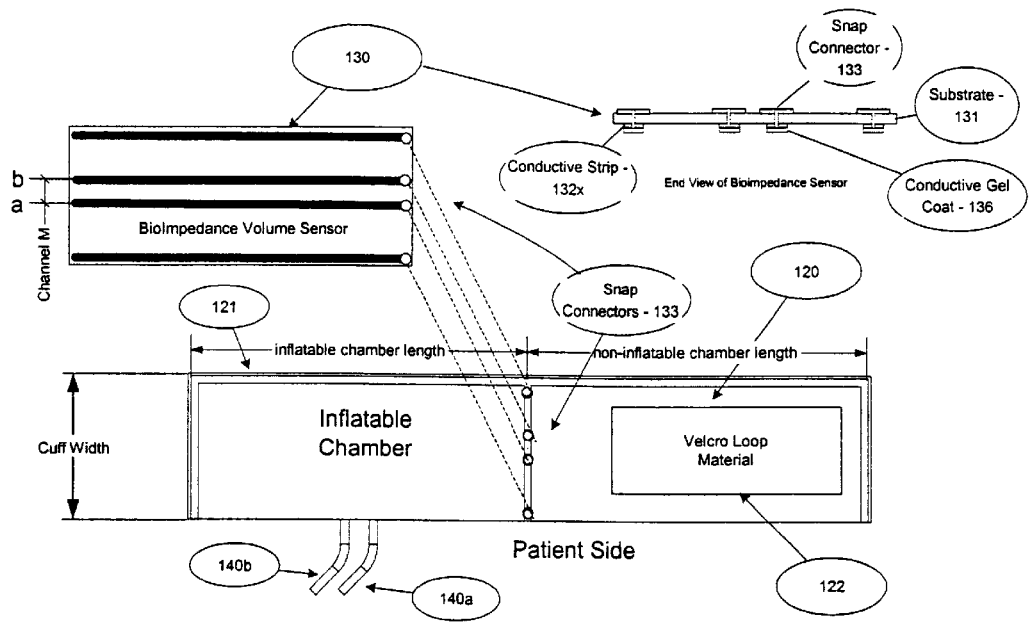
Figure 16:
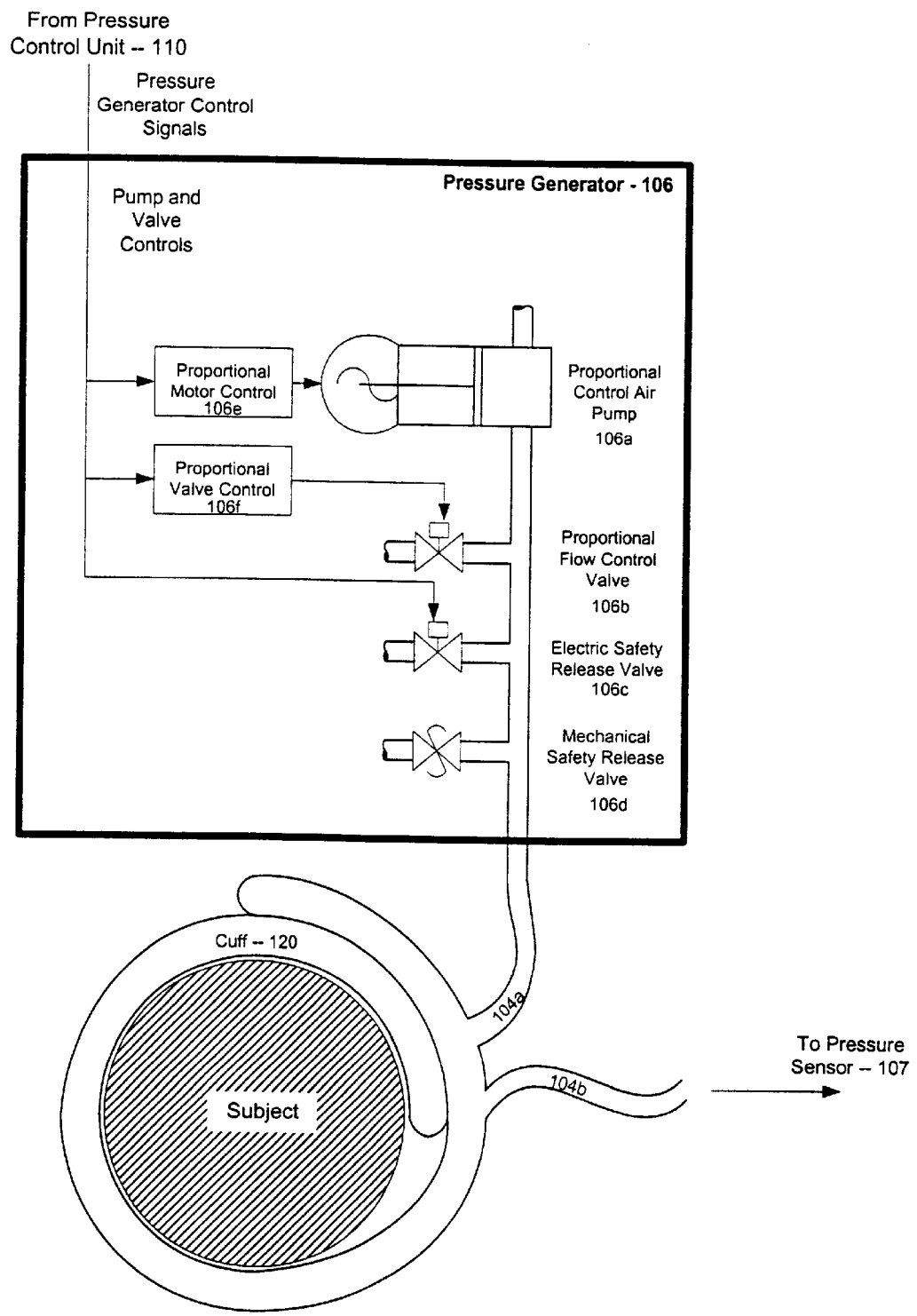
FIGS. 16 through 21 are enlargements of the various other functional blocks shown in the block diagram of FIG. 8 and depict the internal functions of these blocks.

A common blood pressure cuff, as shown in FIG. 15, is the prevalent method available for producing pressure against a body region for physiologic parameter measurement. Since it may be commercially advantageous to use commonly available blood pressure cuffs for pressure generation in certain aspects of the present invention, the inventors have observed that a reasonably accurate determination of state transitions of volume versus pressure data can be accomplished if the volume measuring region defined by the width between sensor leads 132c, 132d of the bioimpedance sensor 130 (FIG. 14), also defining body region a–b (FIGS. 7, and 10 through 15), is kept narrow relative to the width of the inflatable bladder 121 and that the volume measuring region defined by a–b is located at the center of the inflatable bladder as shown in FIG. 15. Desirably, the width of region a–b should not exceed one fifth of certain cuff widths for reasonably accurate determinations of volume/pressure state transitions.

Apparatus

A first exemplary embodiment of the present invention, as shown in FIGS. 8 and 14 through 21, is comprised of an inflatable cuff pressure generator (120) which may be circumferentially fitted around an appendage of the subject including, but not limited to, an arm, leg, finger, or toe in such a manner as to be capable of generating pressure against the body region of the subject; a pressure sensor (107), a Monitor (100), and an impedance volume sensor (130).

Pressure generator 120 is an inflatable cuff for pressure generation using air or other fluid for inflation of the cuff bladder (121). Pressure generator 120 is secured to the subject in this exemplary embodiment by hook and loop material which is commonly used for blood pressure cuff application.

The impedance volume sensor 130 may be a bioimpedance sensor comprised of a matrix of four or more parallel conductive lines fixed to a flexible substrate material, e.g., similar to Mylar with snap connectors on one end of each conductive line as shown in FIGS. 14 and 15. It is desirable in some aspects of the invention that the substrate rigidly maintain the separation between conductive lines, as further discussed below. Impedance volume sensor 130 is fitted to the patient side of 120, i.e., the side intended to be applied to the surface of the body of the subject. The alignment of pressure generator 120 and impedance volume sensor 130 is such that the volume sensor is centered over the inflatable bladder portion of the inflatable cuff representing the pressure generator 120.

The distance between the center conductive lines 132c and 132d of impedance volume sensor 130 in FIG. 14 defines the width of a measurement channel, Channel M, and therefore defines the body region a–b which will be measured by the invention. A desirable separation of the conductive lines which define Channel M of impedance volume sensor 130 is less than the cuff width divided by five. Furthermore, Channel M should be located in the middle of the inflatable cuff width which represents the area of substantially uniform pressure application. Impedance volume sensor 130 is preferably not wider than the cuff 120. Sensing leads 132c and 132d must be positioned between excitation leads 132a and 132b. Excitation leads 132a and 132b are the input and output connections for the constant current source The outer conductive lines 132a and 132b are connected to an AC constant current source which delivers, e.g., a nominal 50 kHz 4 mA RMS constant alternating current to the body region of the subject. It is anticipated by the inventors that the constant current be an alternating current of a frequency capable of producing a uniform current density within the body region for normal operation of the invention. The impedance volume sensor 130 is attached to the inflatable cuff by a connector system which could be individual snap connectors or a connector bank with some latching mechanism for locking the impedance volume sensor into place and creating the electrical circuits for the impedance volume sensing.

The impedance volume sensor is shown as comprised of conductive lines which may be produced with conductive paint or other material suitable for bioimpedance monitoring. Furthermore, the conductive lines may be coated with a gel material suitable for reducing the high resistance layer of the skin of the subject without causing adverse chemical reaction with the subject. Alternatively, point electrodes might be used in the impedance sensor although signal to noise issues may result.

Once the impedance volume sensor is mated with the inflatable cuff, the combination unit (120 and 130) may be applied circumferentially to a limb of the subject. The inflatable cuff is preferably wrapped around the upper arm of the subject, so as to be substantially at the heart level of the subject, with the impedance volume sensor applied directly to the skin of the subject. The inflatable cuff is wrapped snugly around the limb of the subject with the conductive lines preferably running at substantially a right angle to the length of the limb. Adhesive may be used to secure the conductive lines to the subject.

Figure 19:
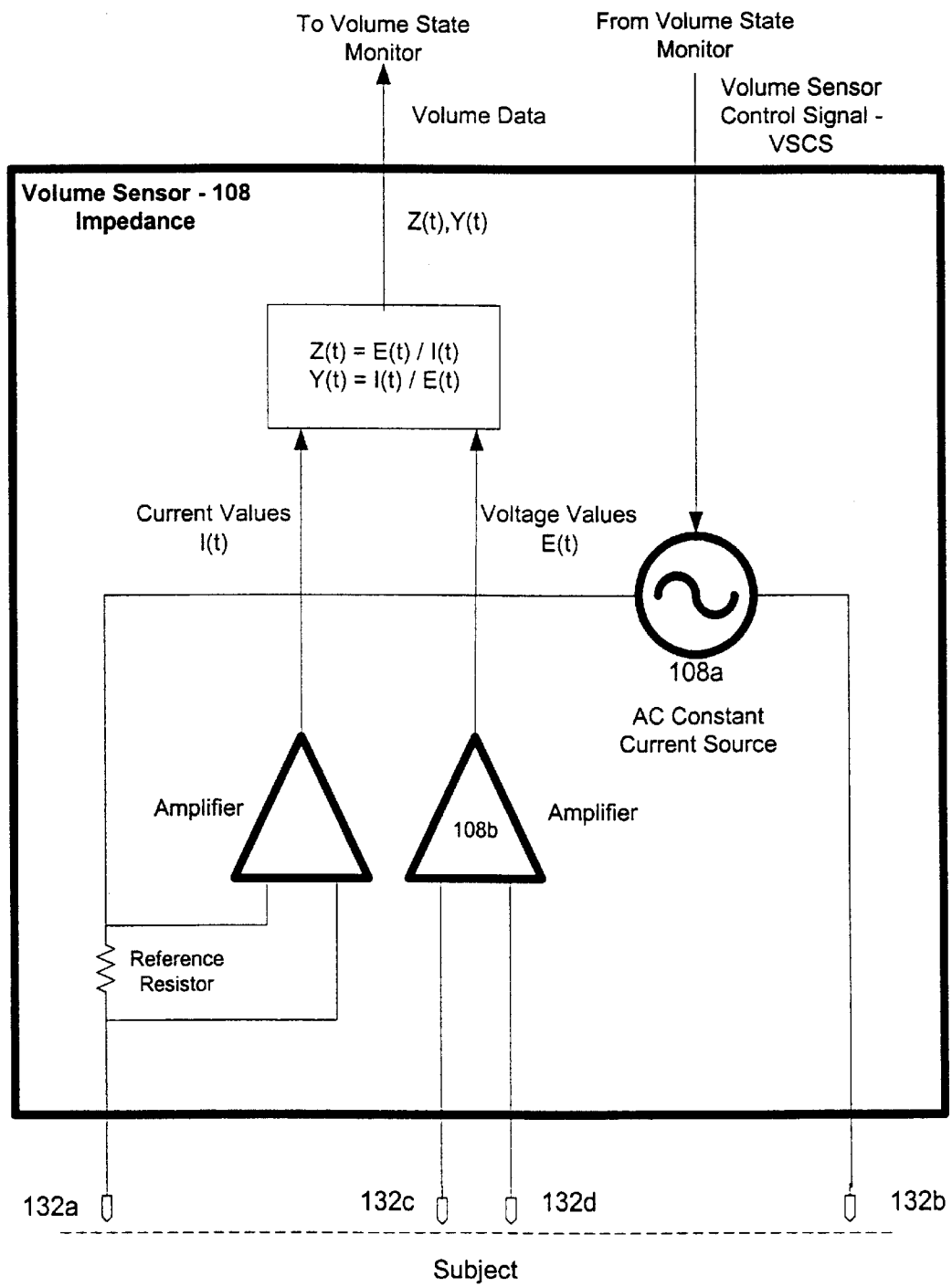

Monitor 100 begins a measurement cycle when the system processor 101 generates a "start" signal. The pressure control unit 110 generates pump and valve signals for the pressure generator 106 (FIG. 16), activating the air pump 106*a* and closing control valve 106*b*. Electrical and Mechanical Safety valves 106*c* and 106*d* are normally closed except in the case of a mechanical or electrical fault exceeding allowed limits for safe operation. Pressure generator 106 inflates the cuff 120 according to a pressure application profile in pressure control unit 110. The pressure application profile is a prescribed inflation/deflation rate and manner suitable for measuring pressure changes in the cuff by the pressure sensor 107 and volume changes by the impedance volume sensor 130. In response to the "start" signal from 101, the volume state monitor 109 produces volume sensor control signals for the volume sensor 108. The volume sensor control signal starts the current source 108*a* to concurrently apply a constant current to the subject through leads 132*a* and 132*b*. A voltage is concurrently measured between 132*c* and 132*d* by the voltage monitor 108*b*. The volume sensor 108 converts the current and voltage signals into impedance (Z(t)) and admittance (Y(t)) signals representing volume data as shown in FIG. 19.

Figure 17:
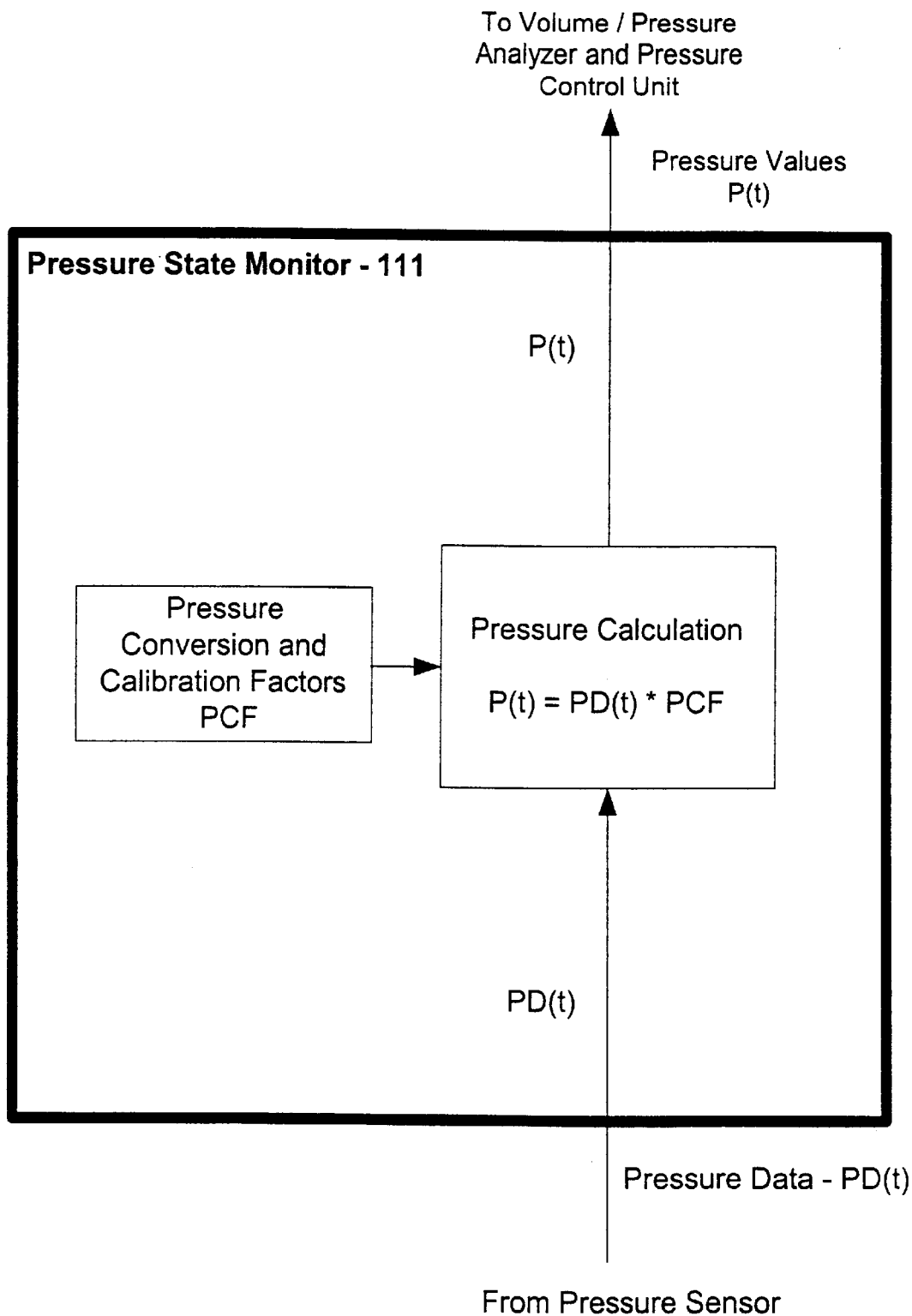
Figure 18:
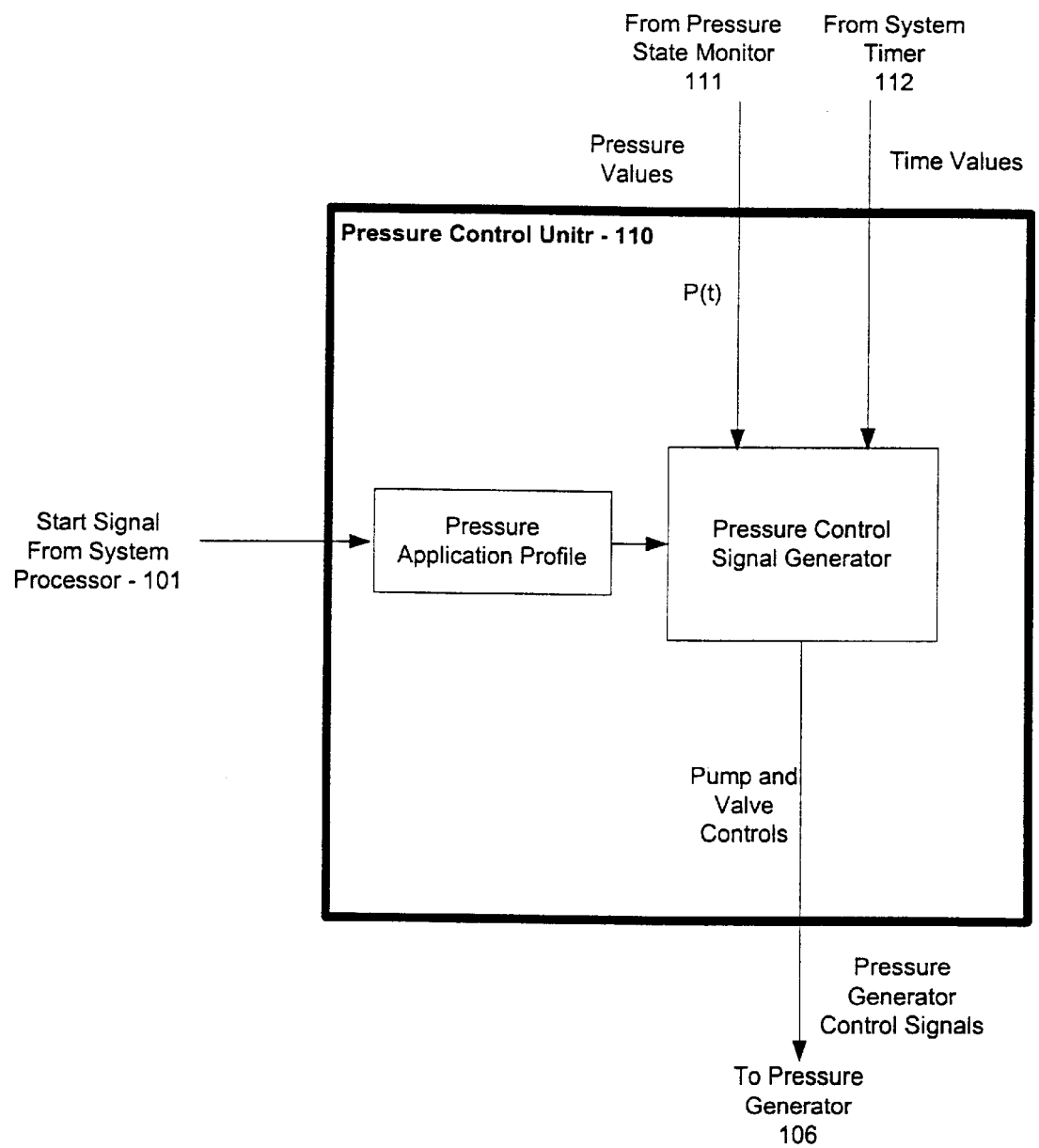

The pressure sensor 107 preferably measures the pressure produced at the cuff 120 rather than at the pump for greater accuracy. The pressure sensor 107 produces a signal representing pressure data. The pressure data signal is received by pressure state monitor 111 and processed into pressure values as shown in FIG. 17. The pressure values are sent to the pressure control unit 110 for feedback control and to the volume pressure analyzer 113 for analysis.

Data

Figure 20:
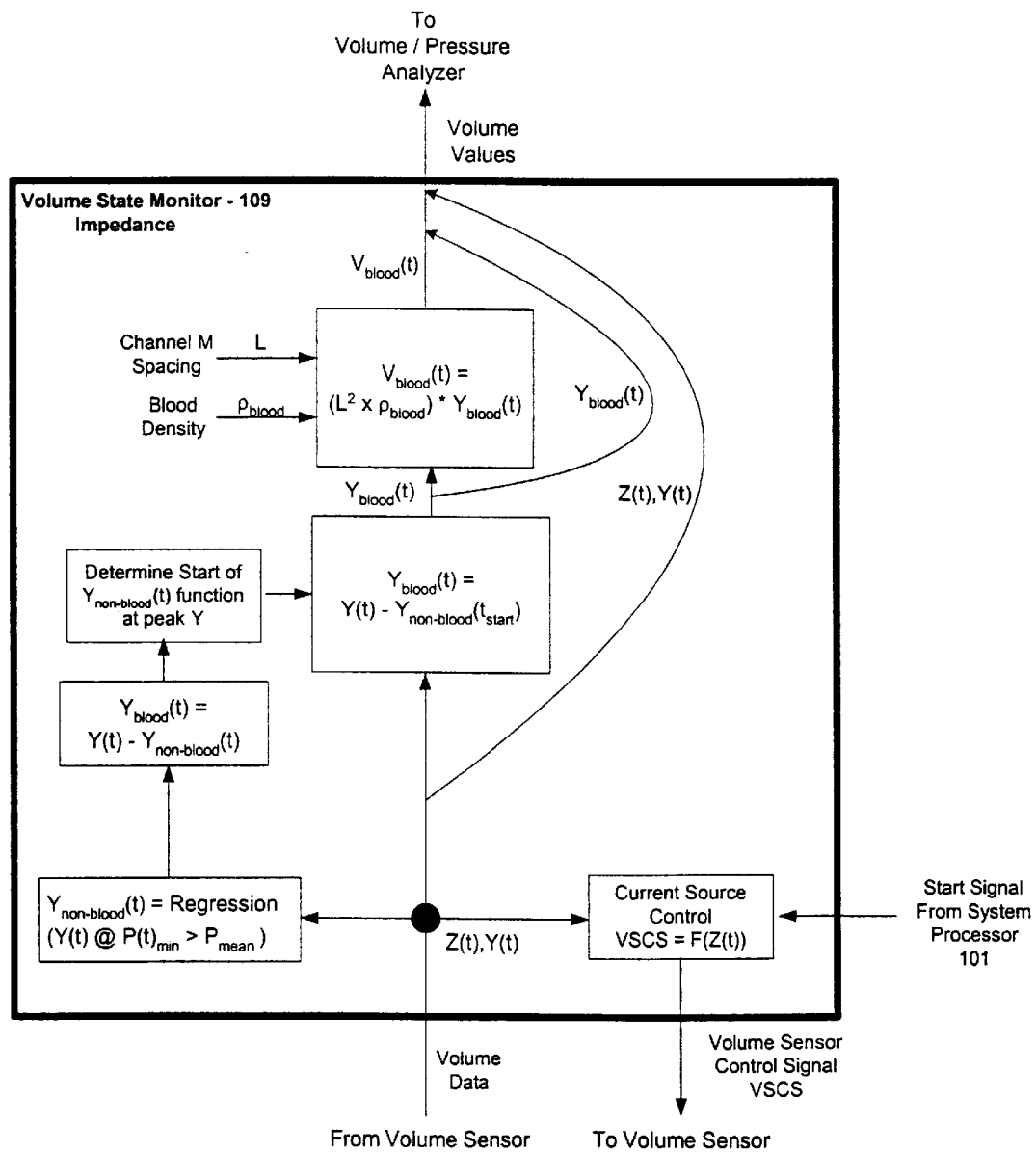
Figure 21:
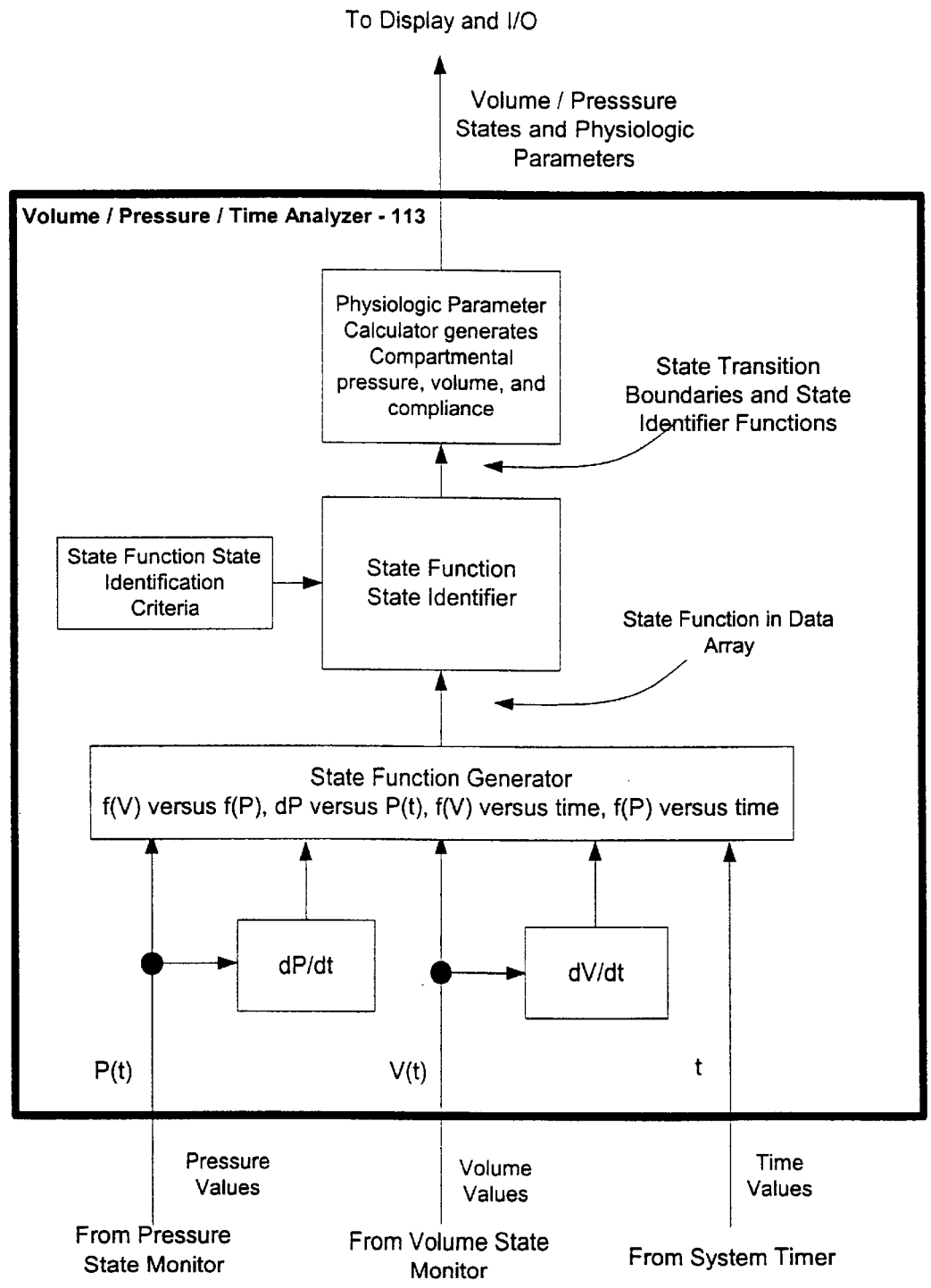
Figure 22:
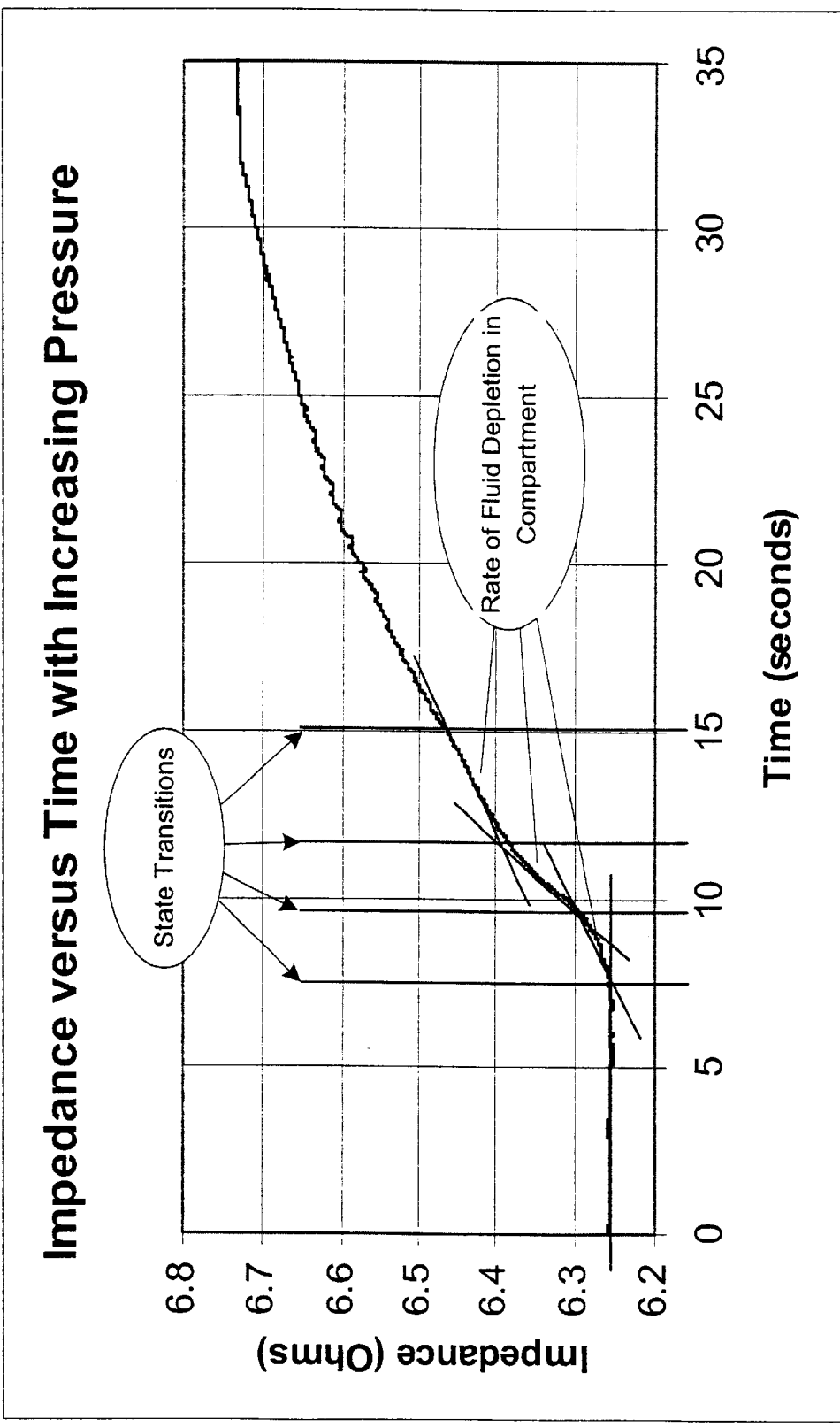
FIGS. 22 and 23 are graphs of impedance values acquired with increasing and decreasing pressure using the apparatus shown in FIG. 8 and illustrating the state changes in volume data versus time.
Figure 23:
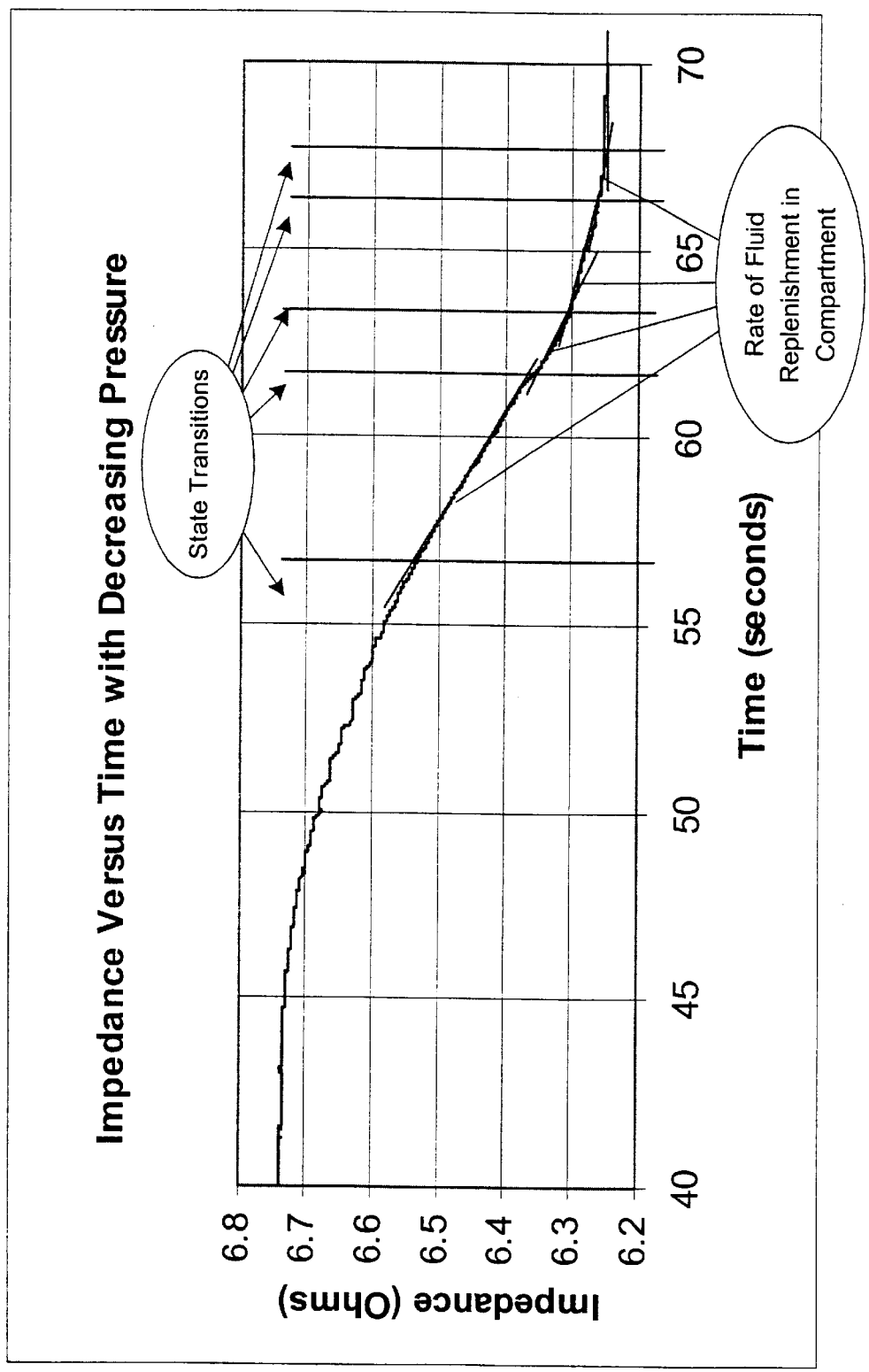
Figure 24:
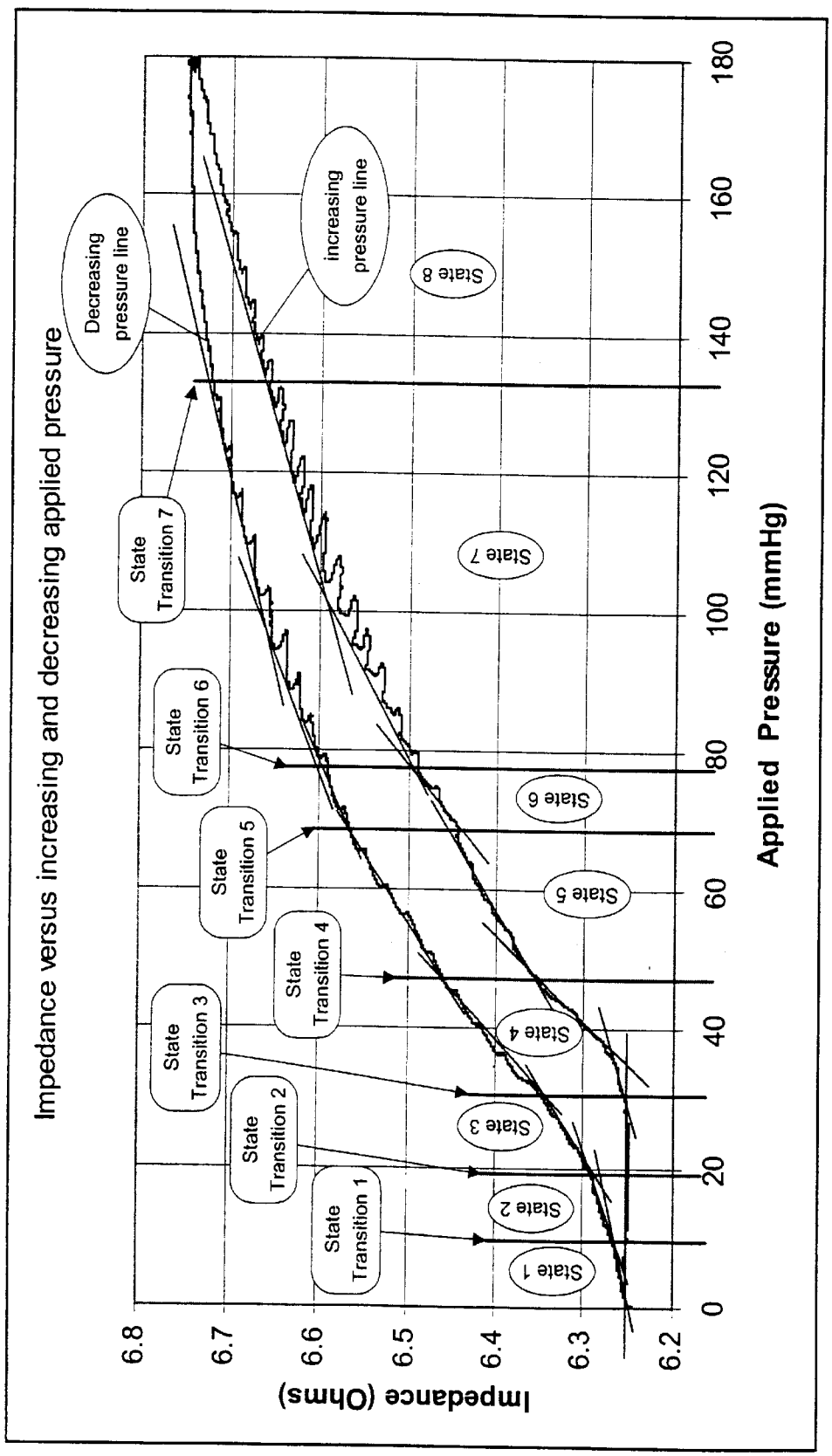
FIG. 24 is a graph of impedance values acquired with increasing and decreasing pressure using the apparatus shown in FIG. 8 and illustrating the state changes in volume data versus pressure data.

The volume state monitor 109 receives the volume data from volume sensor 108 and processes the volume data as shown in FIG. 20. FIGS. 22–24 show data collected with a prototype according to the invention. These figures are presented for illustration of the methods used to process the impedance, pressure and time data to determine the volume and pressure values as well as the state transitions. FIGS. 22 and 23 represent impedance data that is produced by the volume sensor 108 and is related to time. It is shown in FIGS. 22 and 23 that state transitions of impedance/time data can be determined. The impedance/time state transitions identify the rate of fluid depletion and fluid replenishment in various fluid compartments of the subject.

Figure 4:
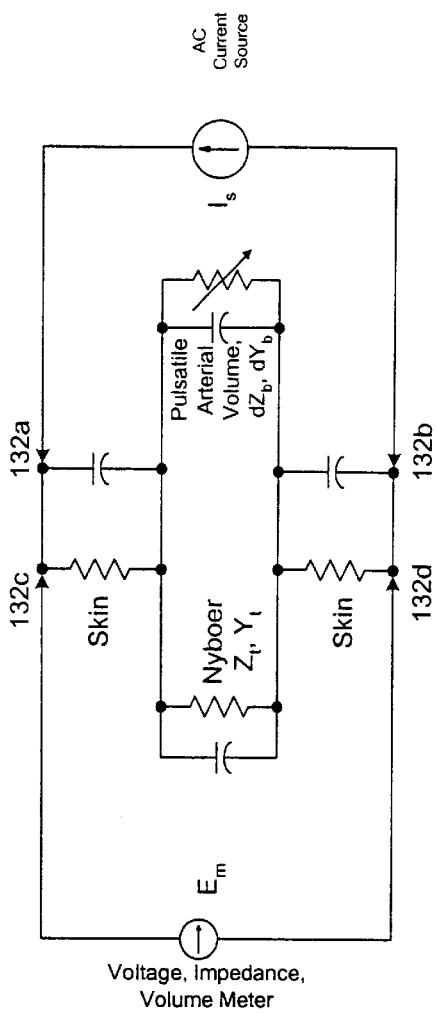
FIGS. 4 and 5, together with FIG. 6 depict equivalent circuit models of the parallel impedance theory by various modeling techniques including the simplified model known from Nyboer in FIG. 4.
Figure 5:
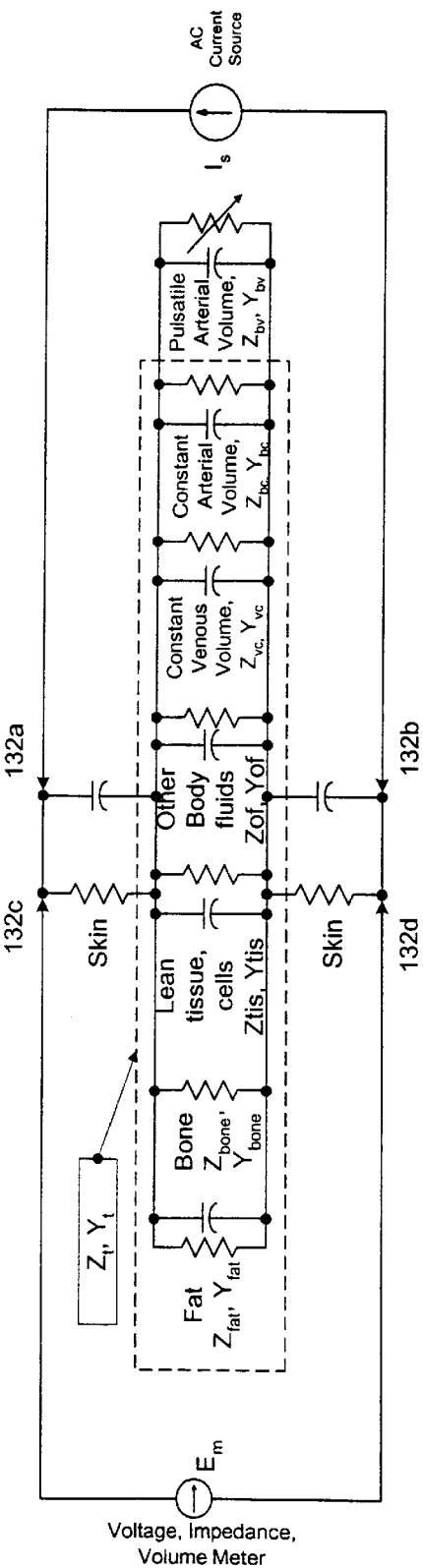

Bioimpedance signals are measured from the body region of the subject as static and changing voltage values between the electrode elements 132*c* through 132*d*. The voltage values acquired by bioimpedance sensing of the subject are indicative of fluid volumes within the sensed body region of the subject. As discussed above, the currently accepted practice for impedance plethysmography uses the Nyboer impedance model as shown in FIG. 4. However, this simplified electrical model of the body combines all of the static or unchanging conductors into a lumped parallel conductor $Y_t$ or impedance $Z_t$. As seen in FIG. 5, the body region of the subject is comprised of numerous conductive pathways made of various materials and having various electrical properties. Further, the pulsatile arterial volume is the only component that is independently accounted for in the Nyboer model of FIG. 4. Therefore, it is clear that prior methods of impedance plethysmography utilizing the Nyboer relationship are greatly limited in comparison to the technique of the present invention utilizing volume depletion and volume replenishment plethysmography.

Figure 25:
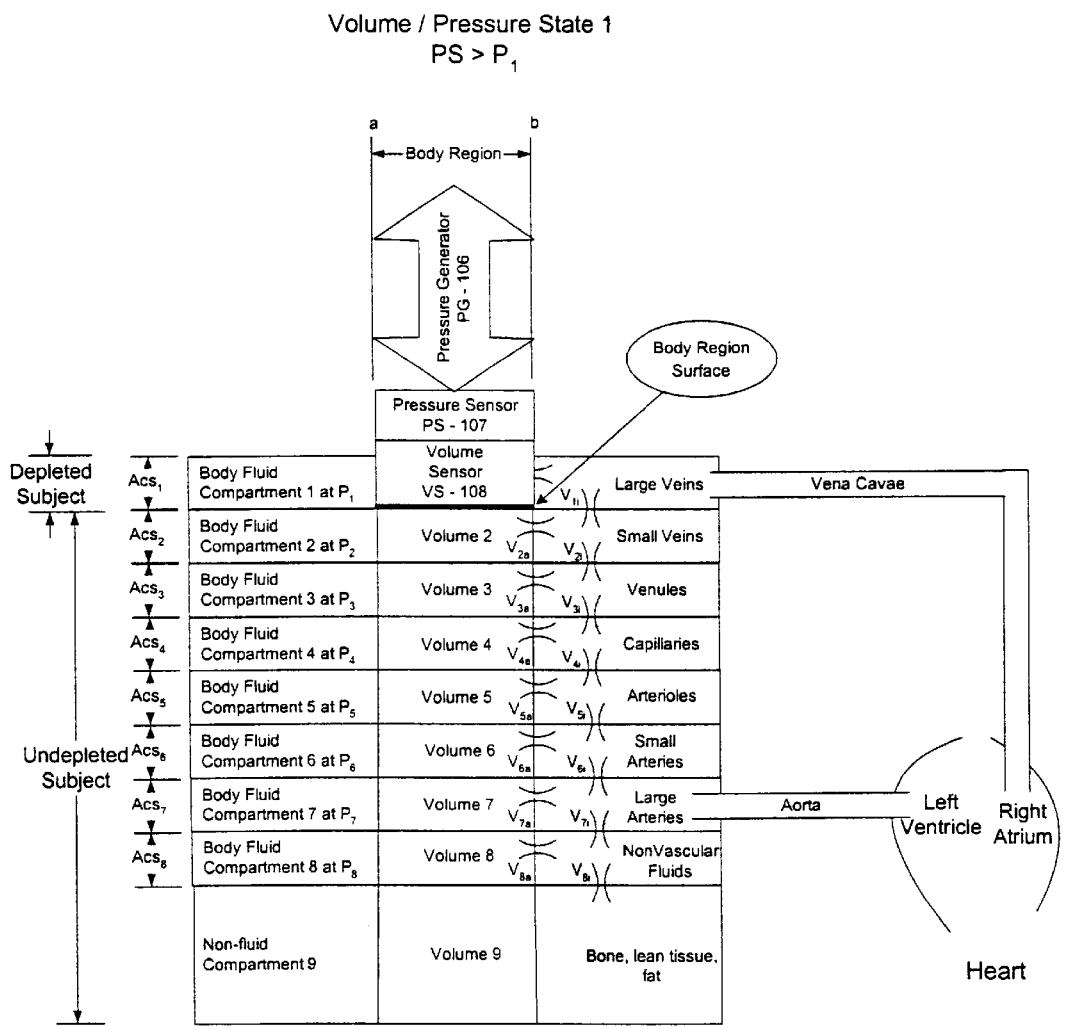
FIGS. 25 through 27 are additional schematic illustrations of an apparatus for carrying out a method in accordance with the present invention as shown in FIG. 8. and illustrating the progression through various fluid chambers as pressure is applied to the subject.
Figure 26:
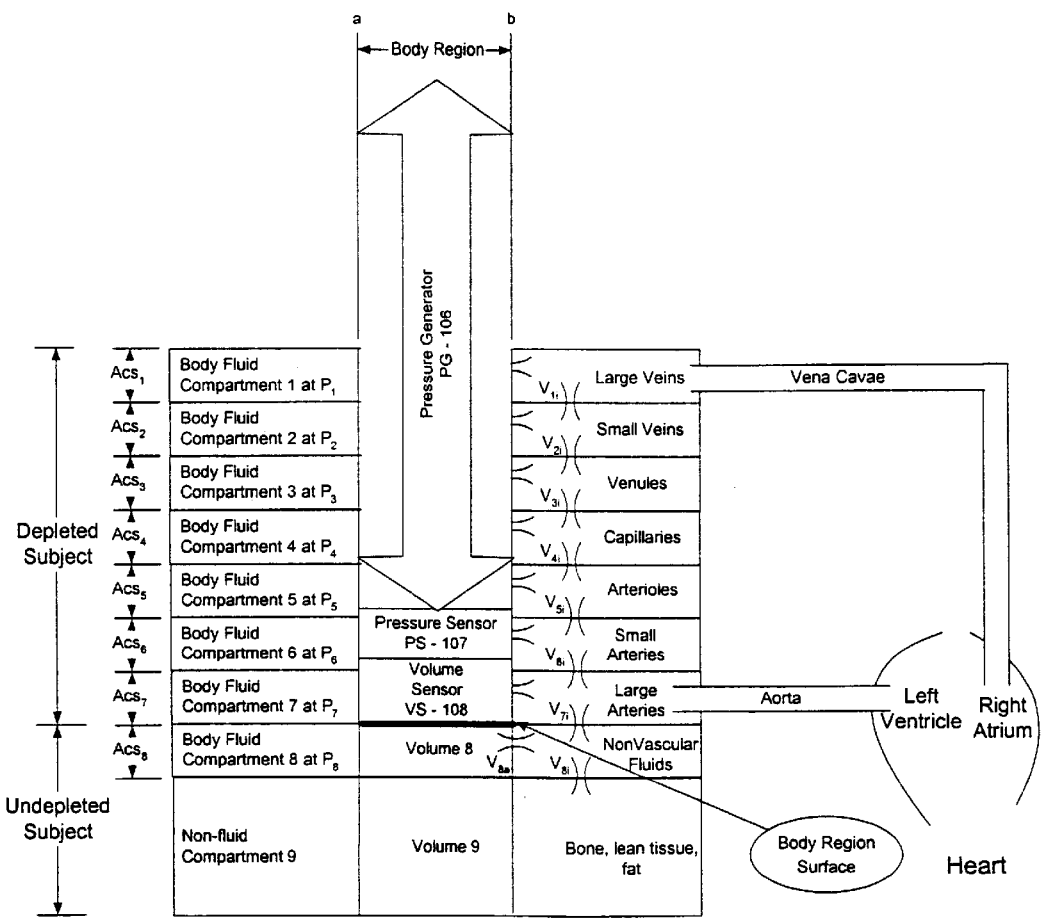
Figure 27:
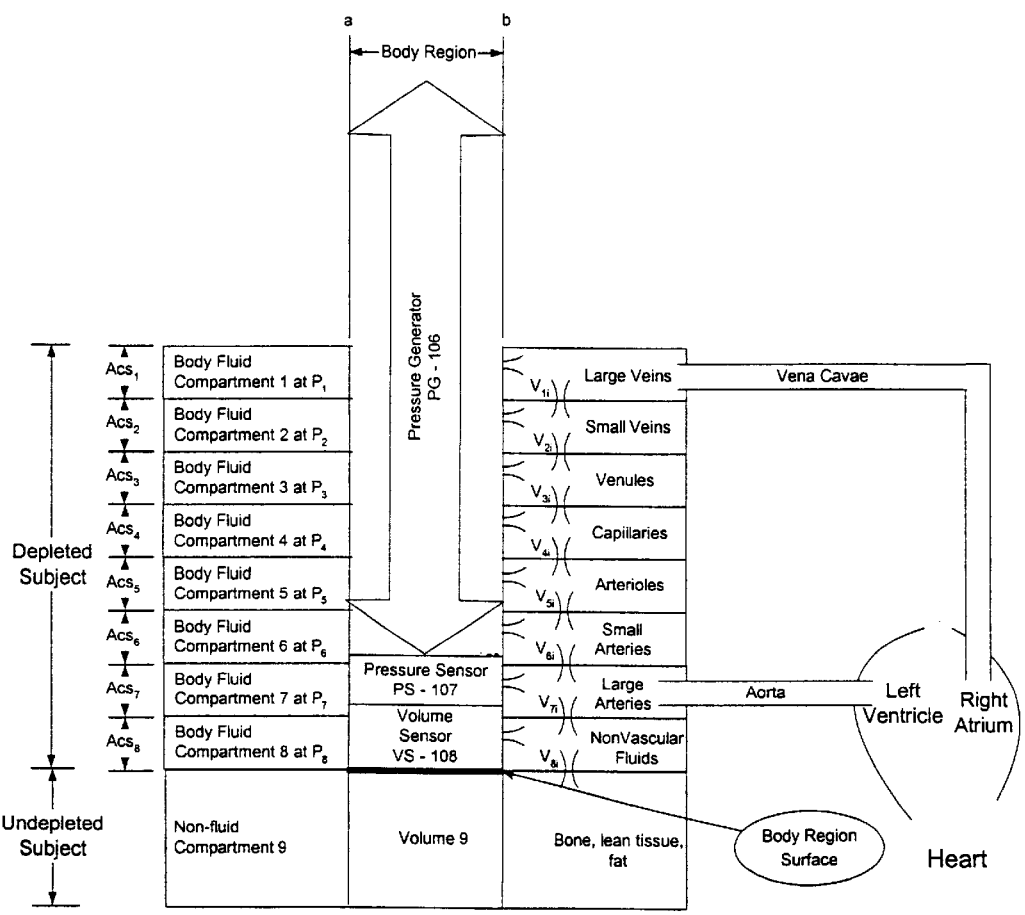

FIGS. 25 through 27 demonstrate how the various fluid compartments are depleted as pressure is applied to the body region surface of the subject. The fluid compartment of Volume 1 depletes first by losing fluid through valve $V_{1i}$ due to its lower pressure. As the applied pressure increases the fluid compartments with higher pressures each depletes in turn as seen in FIGS. 26 and 27. The reverse of this sequence would occur during replenishment.

Figure 29:
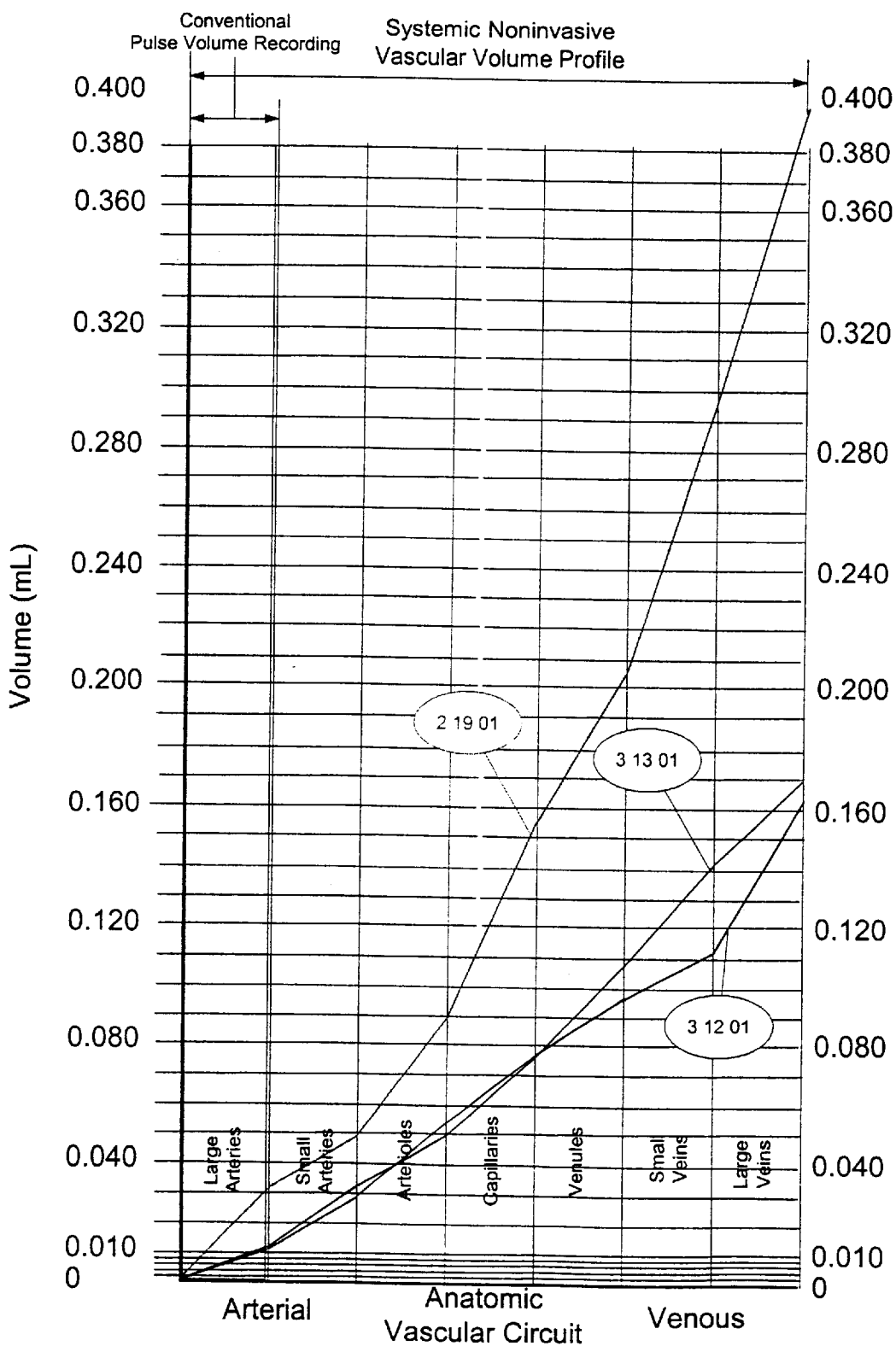
Figure 30:
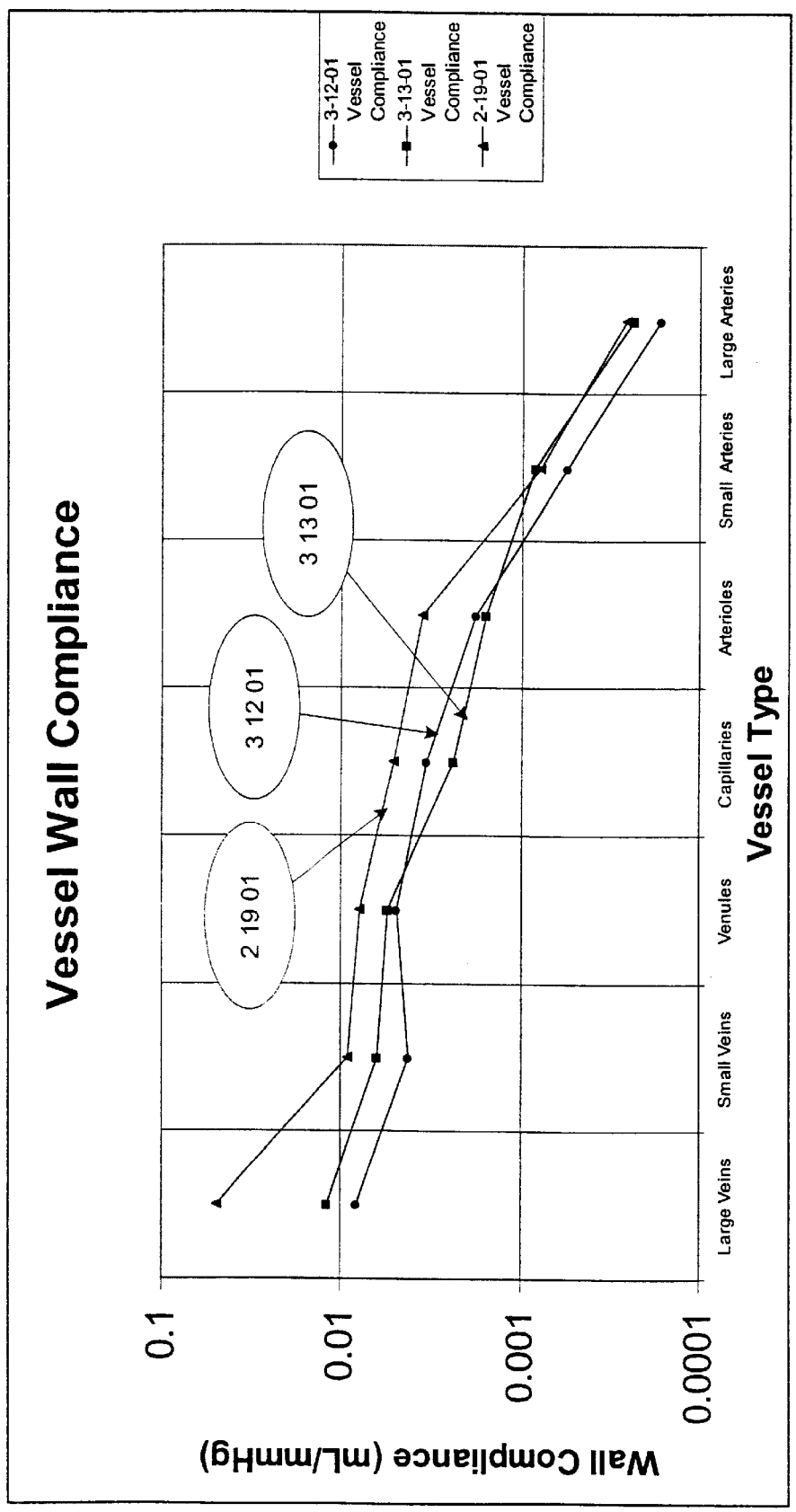
Figure 37:
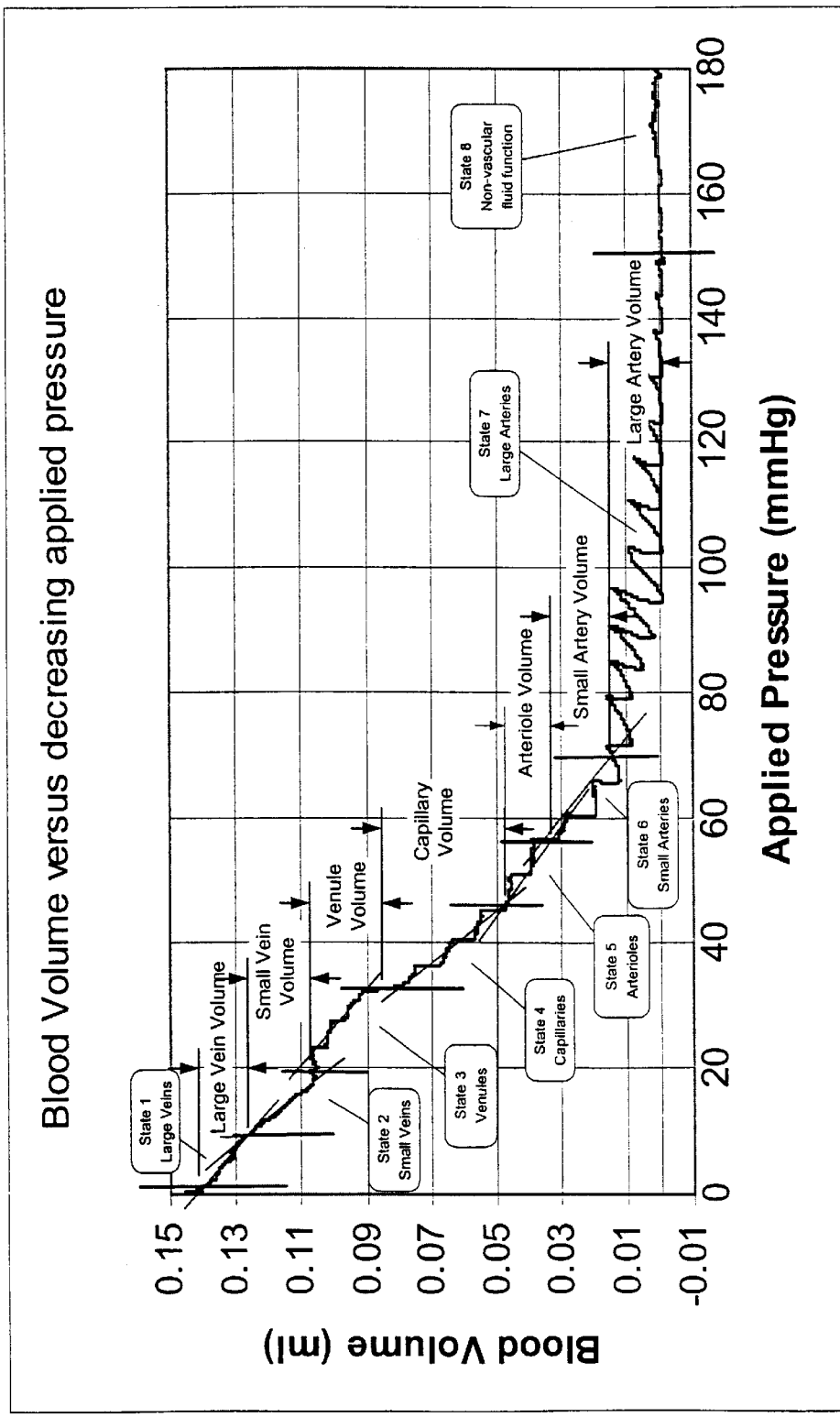
FIG. 37 is a graph of vascular volumes from decreasing pressure volume data with non-vascular fluid removed.

According to the present invention, it is shown that the residual or constant fluid volume can be determined for each of the individual fluid compartments of the vascular system. For instance, the volume of the large veins, small veins, venules, capillaries, arterioles, small arteries, and large arteries can be identified independently by this method as shown in FIG. 37. It can be seen in FIG. 28 how the pressure values determined from state transitions can be plotted on an anatomic vessel chart like the one shown in FIG. 2. It can also be seen in FIG. 29 how the volume values for each vessel can be plotted on the anatomic chart of FIG. 2. Once the pressure and volume values for each vessel type have been identified by the process shown in FIGS. 31 through 37, the compliance value for each vessel type can be determined by the ratio of the volume of fluid contained within the vessel type and the pressure change along the vessel as determined by the state transitions. These characteristic compliance values for each vessel type may then be presented as shown in FIG. 30.

FIG. 24 shows data collected from a body region of the inventor using the first embodiment of the invention. The data is presented as impedance versus applied pressure. Impedance has been shown to be proportional to volume. State transitions can be observed in the impedance data as pressure is increased and decreased against the body region of the subject. Furthermore, it can be seen that some state transitions occurring in the increasing pressure data are consistent with state transitions in the decreasing data. It is anticipated by the inventors that the state transitions are indicative of physiologic parameters such as pressure and volume of the individual fluid compartments in the body region of the subject.

Figure 28:
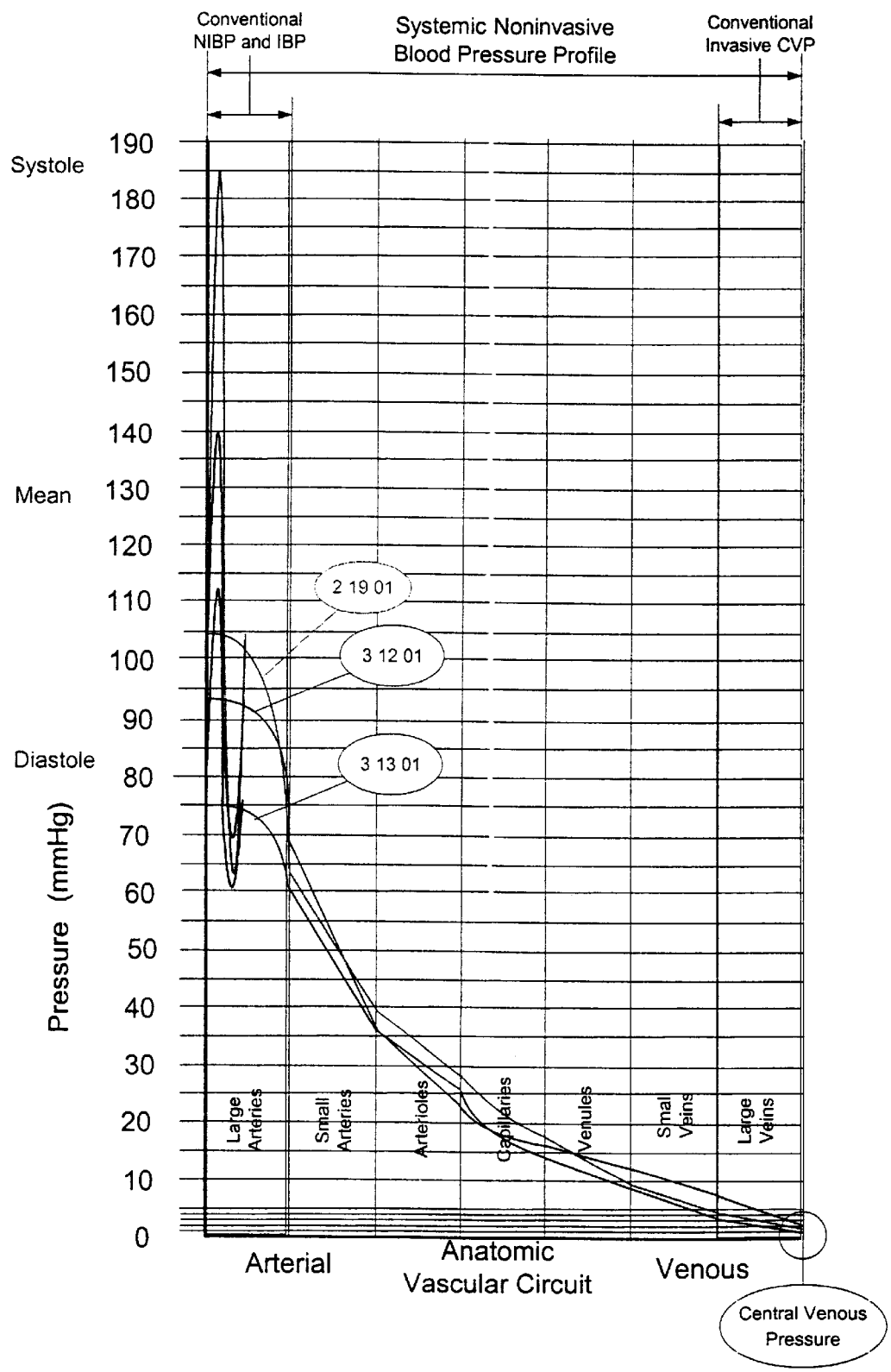
FIGS. 28, 29 and 30 illustrate the comparative nature of vascular pressure, volume and compliance characteristics through the anatomical segments, or fluid compartments, of the vascular system at different times and conditions.

Furthermore, it can be seen that the state transition pressure values may be plotted on an anatomic graph as shown in FIG. 2 or FIG. 28 to illustrate the pressure gradient throughout the vascular bed of the subject. The volume values determined from FIG. 37 are shown plotted anatomically in FIG. 29. Once the pressure values and volume values have been determined for each vascular compartment, the compliance or vessel wall tension of the vessels in that compartment can be determined by the relationship Compliance $(C)=\Delta V/\Delta P$ and plotted by anatomic location as shown in FIG. 30.

Vascular compartment states are identified for the purpose of illustration in FIG. 24 as straight-line segments which identify the volume rate of change characteristic in the body region versus applied pressure. It is anticipated by the inventors that other linear and nonlinear state identification criteria may be used in the analysis of the data shown in FIGS. 22 through 37 for the purpose of identifying volume/pressure change characteristics and state transitions. State transitions are identified in FIG. 24 at the pressures where the volume rate of change characteristic on the graph transitions to a different volume rate of change characteristic.

It is believed by the inventors that the state transitions are indicative of pressure changes at anatomic locations between fluid compartments in the body region of the subject and are indicative of the inter-compartmental valve characteristics between fluid compartments. Furthermore, it is anticipated by the inventors that the volume changes between state transitions are indicative of the volume of the fluid compartment identified by the characteristic pressures ($P_i$) between the state transitions.

Figure 31:
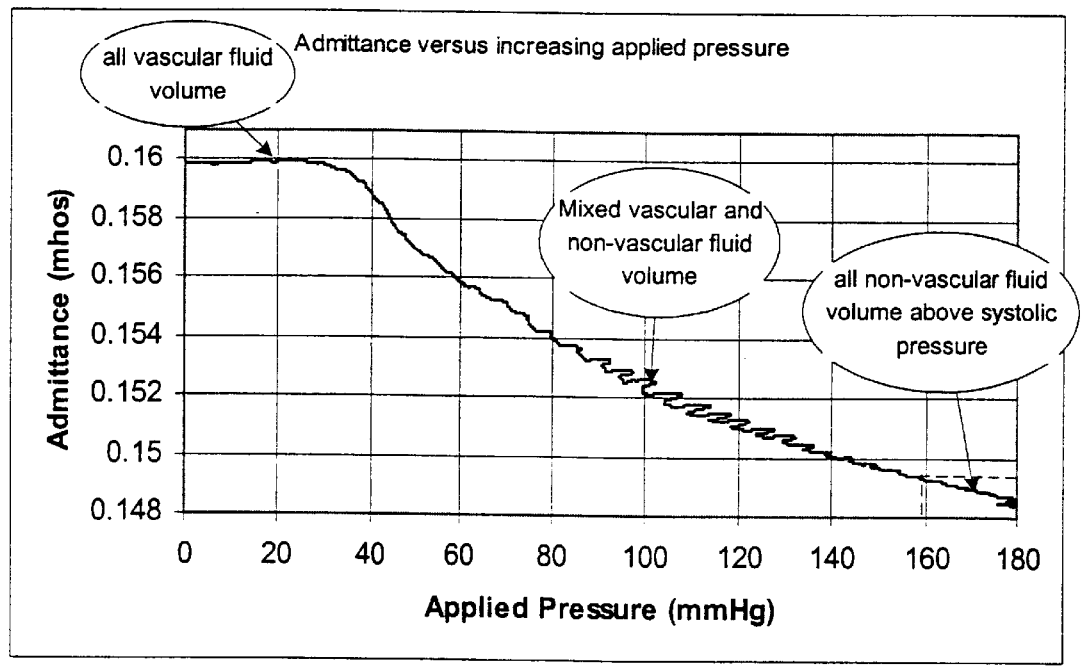
FIGS. 31 through 36 are graphs of values acquired using the apparatus shown in FIG. 8 and illustrating a methodology that can be employed for devolving the composite data into its component parts for volume determination of individual fluid compartments.
Figure 32:
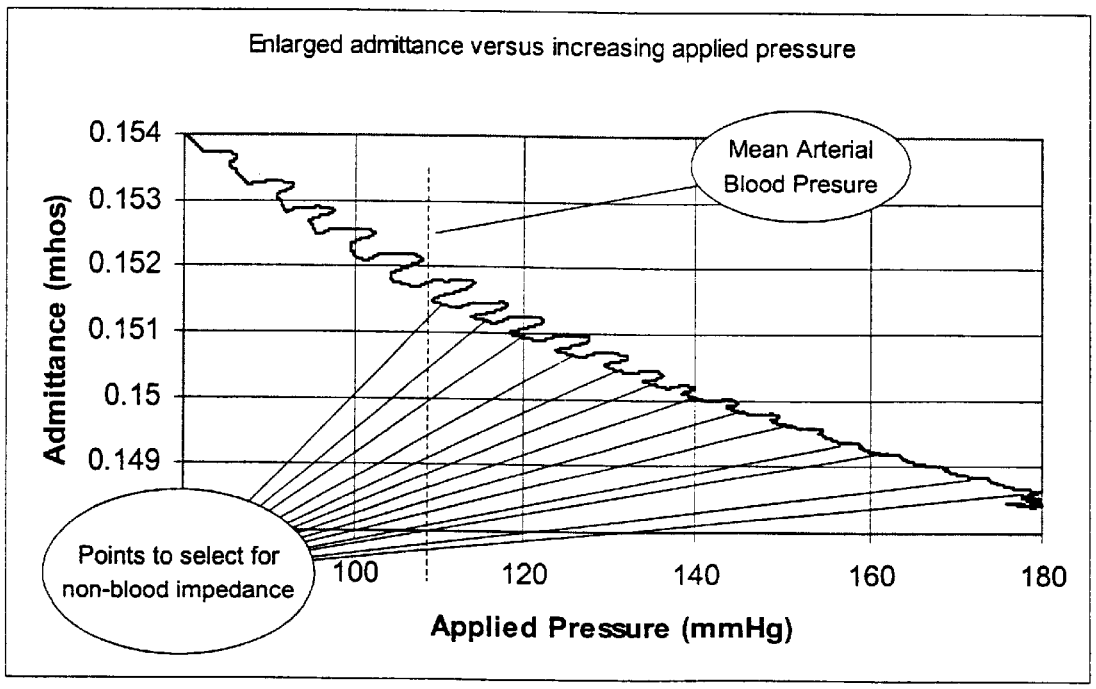
Figure 33:
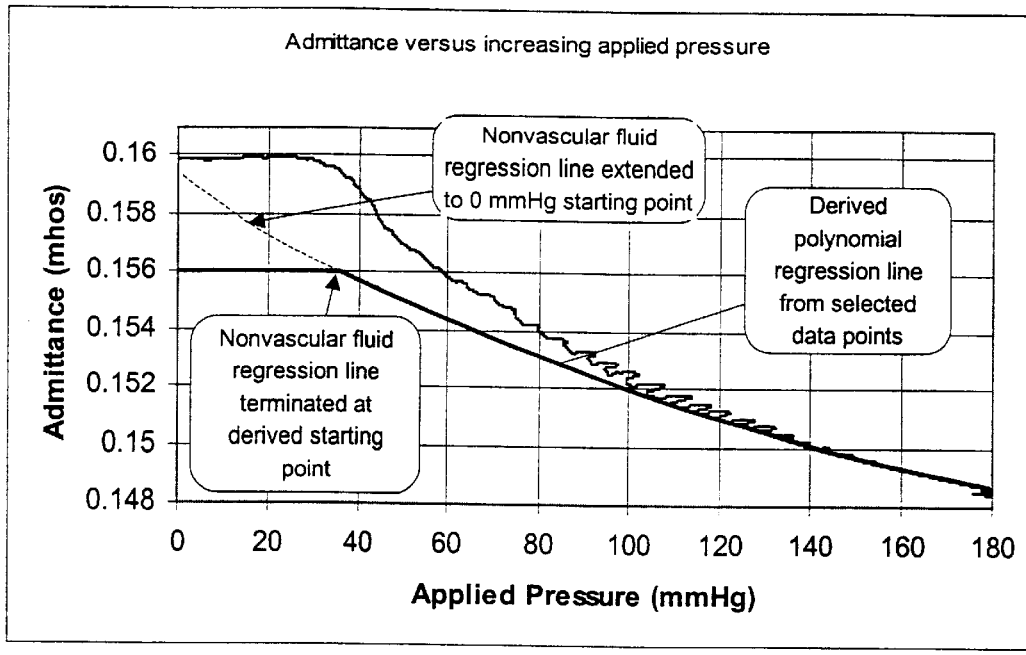
Figure 34:
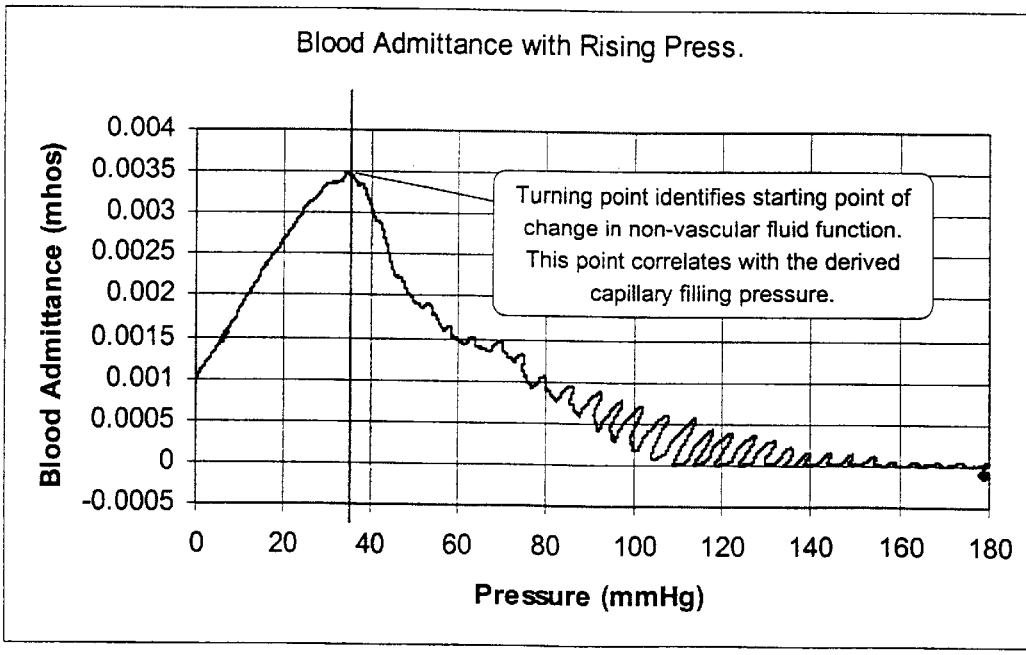
Figure 35:
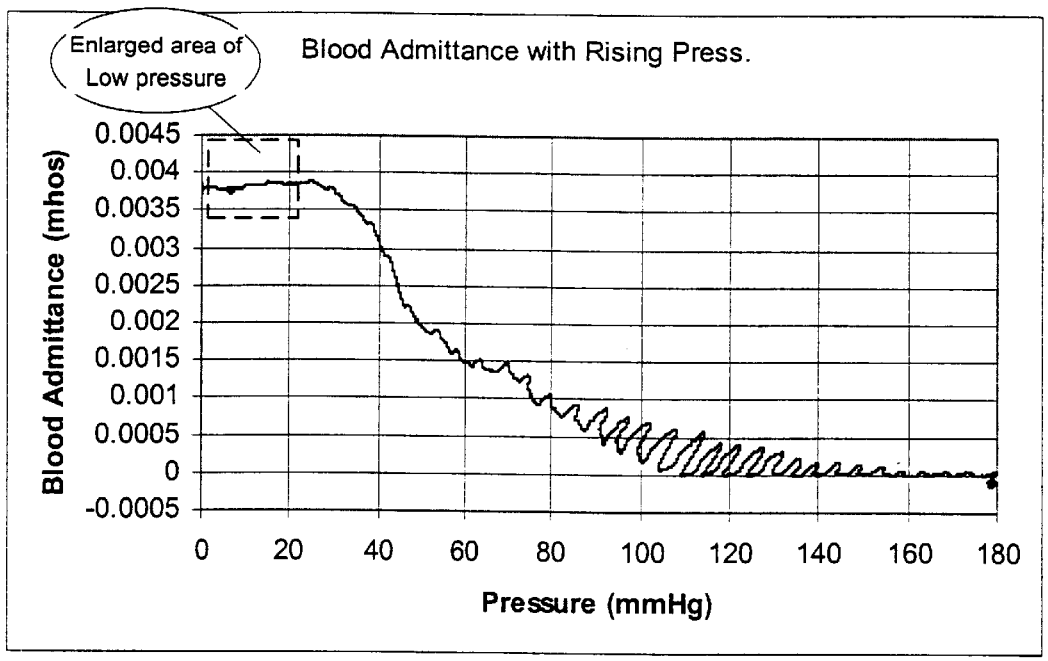
Figure 36:
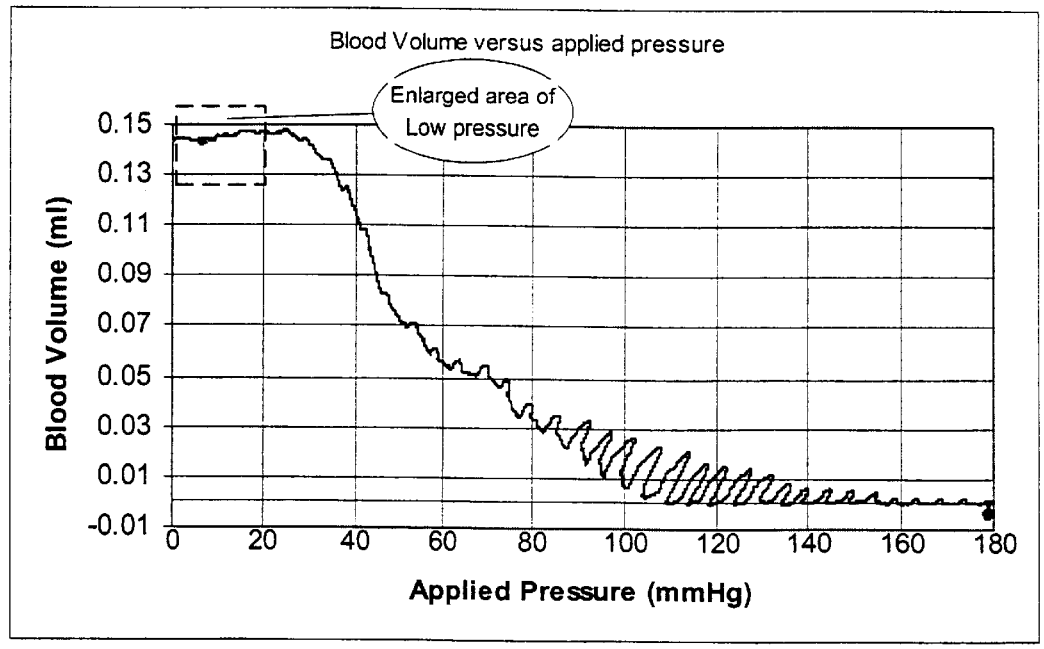

The inventors have discovered that the non-vascular fluid compartment (Vol. 8 in FIG. 7) has a characteristic pressure range that overlaps many of the vascular fluid compartments. A series of data processing steps are illustrated in FIGS. 31 through 37, which show one method of isolating the volume values contributed by fluid compartments with overlapping pressure ranges. A fully processed Blood Volume versus Applied Pressure data set is illustrated in FIG. 37. There are two key observations made by the inventors that allow the nonvascular fluid function to be independently determined. The first observation as shown in FIG. 31 is that the nonvascular function continues at pressures higher than the highest vascular pressure known as systole.

The second observation is that the large artery volume goes to zero at diastole when the applied pressure equals the mean pressure in the large arteries. The significance of these two observations allows for determination of the non-vascular fluid function that overlaps the pressure range of multiple vascular fluid compartments in the raw impedance data acquired from the subject. The process of determining the non-vascular fluid function, as illustrated in FIGS. 31 through 37, allows that function to be removed by regression from the raw data, leaving only vascular fluid related data left for further analysis. This methodology is an important improvement to the art since the physiologic parameters associated with the vascular fluid compartments such as pressure and volume were not directly discernable from the raw data since it could not be determined what portion of the raw data was attributable to the vascular fluid compartments and what portion was attributable to the non-vascular fluid compartments.

FIGS. 38 through 43 illustrate several important aspects of the present invention, 1) the ability to identify state transitions from multiple modalities of data acquisition and data processing, 2) the ability to identify venous pressure and specifically central venous pressure noninvasively, 3) the ability to precisely measure the vessel wall tension or compliance of nonpulsating vessels, and 4) the ability to identify fluid replenishment within a body region of the subject during release of the pressure in that body region.

Figure 38:
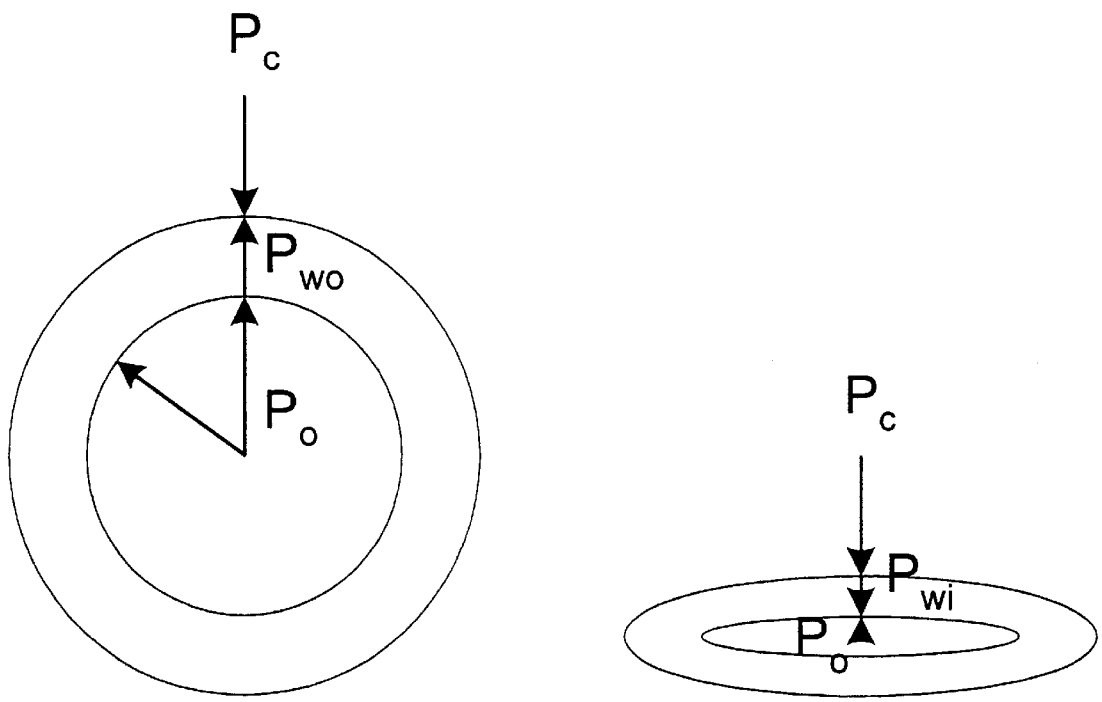
FIG. 38 is a schematic representation of a cross section of vessel walls and depicts the various forces that act on it normally and in compression.
Figure 39:
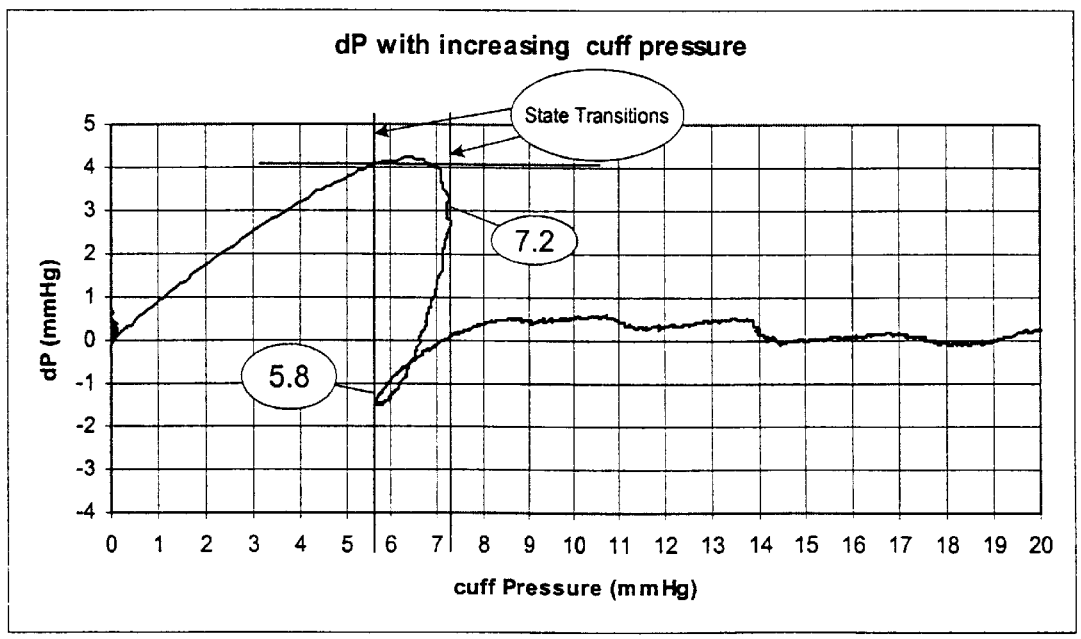
FIGS. 39 through 43 are graphs of various types of data collected on the same subject using the apparatus shown in FIG. 8 with both increasing and decreasing pressure and depicting the state transition indicative of large vein internal pressure.

FIG. 38 illustrates a vessel in the body region of the subject. For example, this vessel could be a large vein. The vessel is internally pressurized to a pressure $P_o$ by the normal physiologic functioning of the subject. The external pressure generator of the invention applies a pressure to the vessel noted as $P_c$. It should be understood that the pressure values in FIG. 39 are the values of $P_c$. Furthermore, the vessel wall contributes mechanical forces known as vessel wall tension which are shown as $P_{wo}$. It is demonstrated in FIG. 39 that the applied pressure is slowly increased in the inflatable cuff pressure generator against the body region of the subject. It is also shown that a deformation begins to occur at 5.8 mmHg and that a breakdown of the vessel occurs at 7.2 mmHg. Once the vessel breakdown occurs the vessel is deformed as shown in the right image of FIG. 38.

It can be observed in FIG. 39 that the breakdown of the vessel causes a rapid change in cuff pressure. This is due to the rapid reduction in fluid volume within the zone of pressure generation in the body region of the subject. The rapid volume reduction in the body region of the subject due to the collapsing vessel causes an associated change in the pressure within the cuff because the volume displacement of the cuff is dependent on the volume displacement in the body region of the subject. Note also in FIG. 39 that the pressure retracement, which occurs in the cuff, is limited to the pressure at which the original vessel deformation began at 5.8 mmHg. Thus, it can be seen that, in certain circumstances the cuff may act as its own volume, or state change, indicator without use of a further separate plethysmograph such as the impedance sensing device.

Figure 40:
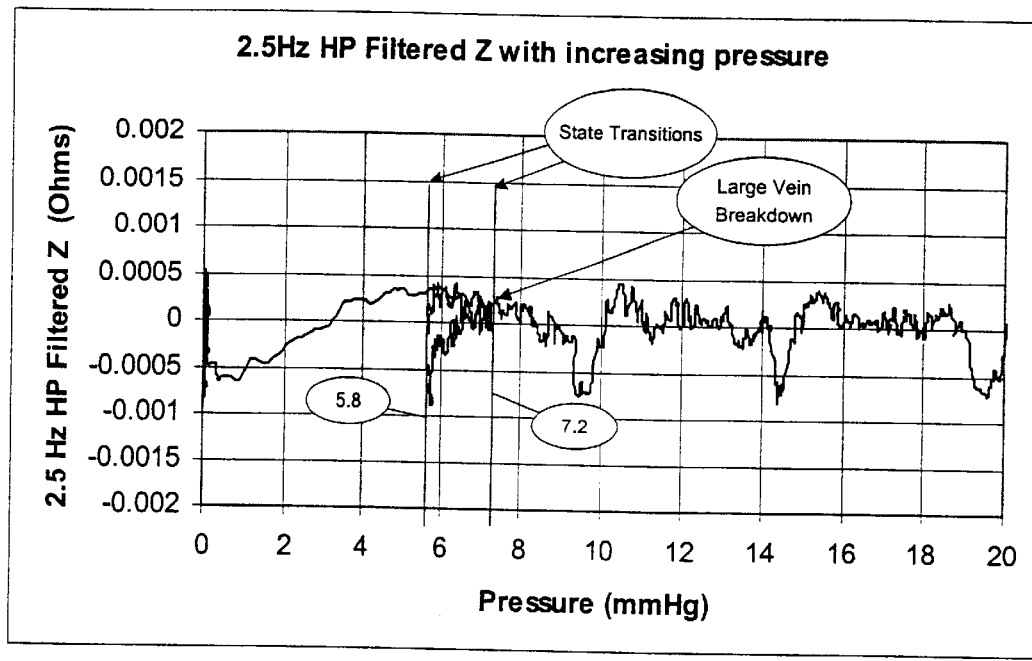
Figure 41:
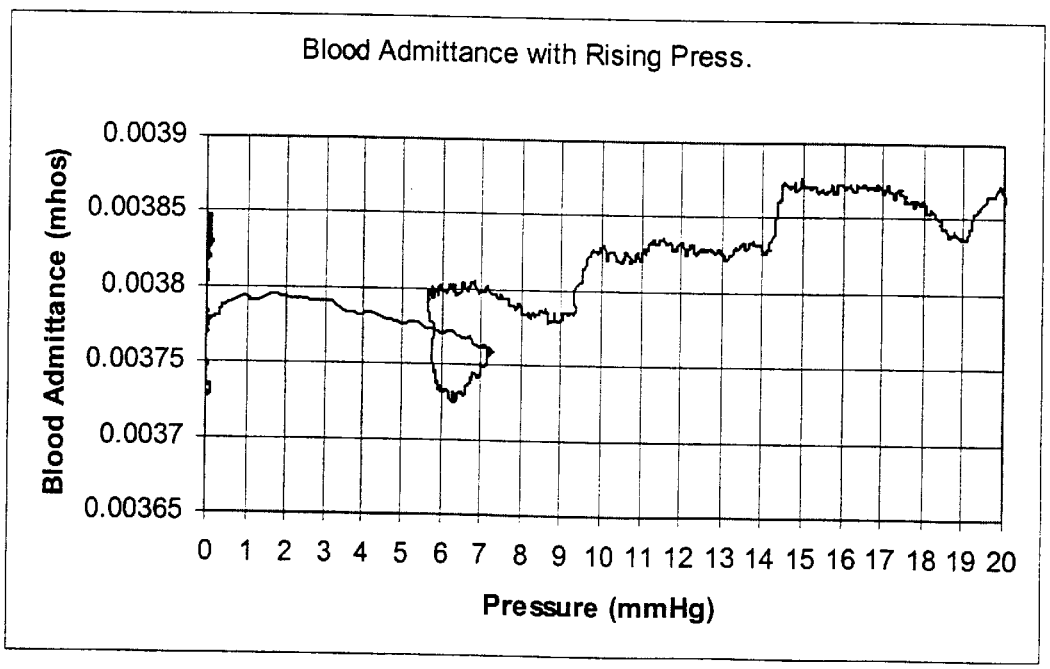
Figure 42:
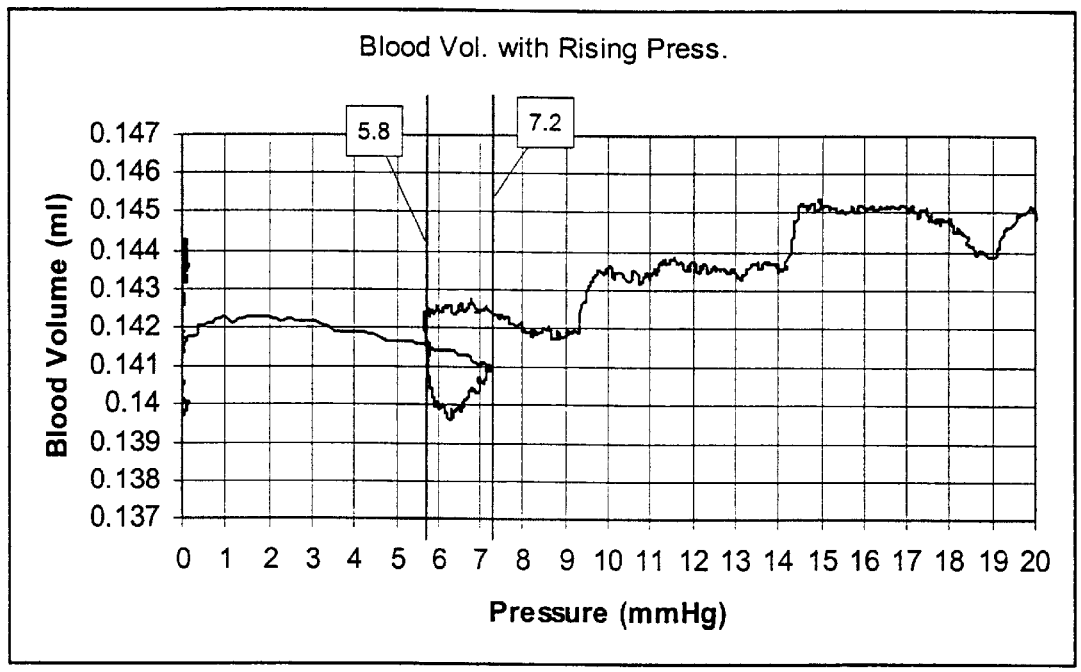

The state transitions identified in FIG. 39 demonstrate an ability of the present invention to determine the pressure in the vessel $P_o$ as the lower pressure state transition, and the vessel wall tension $P_{wo}$ as the difference between the lower pressure state transition and the upper pressure state transition. In the case of the subject shown in FIG. 39, the vein wall tension was 1.4 mmHg. FIG. 40 shows the same vessel wall phenomenon as FIG. 39 using the change in impedance versus pressure data. For the same subject, the lower and upper pressure state transitions are identified as the same pressure values determined in FIG. 39. The phenomenon can also be observed in FIG. 41 using admittance data versus pressure, and in FIG. 42 using blood volume versus pressure data.

Figure 43:
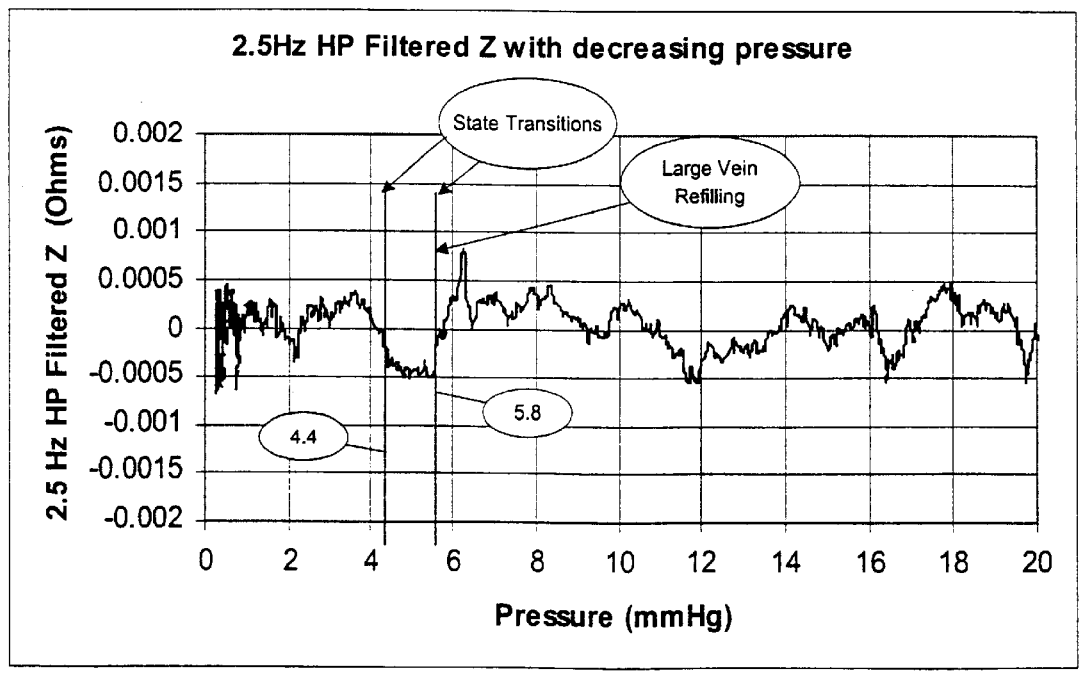

FIGS. 39 through 42 represent data collected using a pressure generation mode of increasing pressure from zero starting pressure. FIG. 43 illustrates impedance versus pressure data as a function of time as collected from the same subject with a decreasing pressure generation modality. Here it can be seen that the same characteristic vessel wall tension is apparent whether the vessel is replenishing fluid volume or the vessel is depleting fluid volume. However, there appears a distinct difference from the depleting mode, i.e., the upper state transition occurs at 5.8 mmHg and the lower state transition occurs at 4.4 mmHg.

Referring to FIG. 38, the vessel wall tension $P_{wo}$ in the fully inflated vessel on the left is a force vector pointing out of the vessel and therefore opposing the pressure generator PC In the compressed state of the vessel shown on the right of FIG. 38, we model the vessel wall tension $P_{wi}$ as a force vector pointing into the vessel and opposing the internal pressure of the vessel $P_o$. This accurately models the differences in observed behavior between FIG. 40 and FIG. 43. This is a very important observation, since it means that the vessel wall demonstrates plastic behavior when it is deformed. Further, it is of interest that the magnitude of opposition attributable to the vessel wall is the same in each direction for this subject.

It has also been determined by the inventors that the value of large vein filling pressure measured in the upper arm of the subject by the techniques of the present invention closely approximate the central venous pressure (CVP), defined as the right atrial filling pressure, when the subject is in the prone or supine position. In the supine position, the subclavian vein has minimum resistance to flow back to the heart and the difference between the pressure in this vein in the upper arm and the right atrium is minimized. Thus, when the present invention determines the pressure in the large vein of the upper arm this can be considered as equivalent to the central venous pressure of a supine subject.

It can be seen in FIGS. 39 through 43 that a consistent behavior of a vessel wall in the body region of the subject was identifiable by multiple modalities of data acquisition and data processing. The first modality in FIG. 39 relates time rate of change in pressure of the cuff to the total pressure of the cuff. The remaining figures relate various derived volume indicators to the cuff pressure. All show distinct state transitions as the large vein collapses.

It is anticipated by the inventors that the invention may be produced in multiple forms utilizing various methods of pressure generation, pressure sensing, volume sensing, mathematical operations, interface means, and other techniques as set forth herein for determination of physiologic parameters. Therefore, embodiments of the invention were provided for various forms of the invention without intent to limit the scope of the invention to any particular form or structure.

We claim:

1. A method of obtaining a physiological parameter of a body fluid compartment, comprising the steps of:
   a. applying a series of known pressure values to a body region containing a body fluid to deplete or replenish a fluid volume from the body region;
   b. sensing the body region under pressure to derive a series of body fluid volume indications for a plurality of body fluid compartments in the body region under pressure;
   c. referencing the body fluid volume indications of the plurality of body fluid compartments to the series of known pressure values; and
   d. identifying a transitional relationship of the body fluid volume indication values referenced to the series of pressure values, thereby indicating the physiological parameter of the body fluid compartment.

2. The method according to claim 1 wherein sensing the body region is done without regard to a pulsatile body signal.

3. The method according to claim 1 wherein the physiological parameter is vessel compliance.

4. The method according to claim 1 wherein the physiological parameter is central venous pressure.

5. The method according to claim 1 wherein the physiological parameter is a static fluid pressure.

6. The method according to claim 5 wherein the physiological parameter is a static fluid pressure of the capillaries.

7. The method according to claim 5 wherein the physiological parameter is a static fluid pressure of the venuoles.

8. The method according to claim 5 wherein the physiological parameter is a static fluid pressure of the small veins.

9. The method according to claim 5 wherein the physiological parameter is a static fluid pressure of the large veins.

10. The method according to claim 5 wherein the physiological parameter is a static fluid pressure of the arterioles.

11. The method according to claim 1 wherein the physiological parameter is a pulsatile vessel static fluid pressure.

12. The method according to claim 11 wherein the physiological parameter is a static fluid pressure of the small arteries.

13. The method according to claim 11 wherein the physiological parameter is a static fluid pressure of the large arteries.

14. The method according to claim 13 wherein the physiological parameter is a mean blood pressure of the large arteries.

15. The method according to claim 13 wherein the physiological parameter is a systolic blood pressure of the large arteries.

16. The method according to claim 13 wherein the physiological parameter is a diastolic blood pressure of the large arteries.

17. The method according to claim 5 wherein the physiological parameter is a static fluid pressure of the nonvascular fluids.

18. The method according to claim 1 wherein the physiological parameter is a blood oxygen level.

19. The method according to claim 1 wherein the body fluid compartments are adjacent.

20. The method according to claim 1 wherein the known pressure values are contiguous.

21. The method according to claim 1 wherein the physiological parameter is a fluid volume of the body fluid compartments.

22. A method of obtaining a physiological parameter of a body fluid compartment, comprising the steps of:
   a) applying a series of known pressure values to a body region containing a body fluid to deplete or replenish a series of adjacent body fluid compartment fluid volumes from the body region;
   b) sensing the body region under pressure to derive a series of body fluid volume indication values for the adjacent body fluid compartments of the body region under pressure;
   c) referencing the body fluid volume indication values of the adjacent body fluid compartments to the series of known pressure values; and
   d) identifying transition points at which a relationship of the body fluid volume indication values referenced to the series of pressure values changes, thereby indicating a body fluid physiological parameter.

23. The method of obtaining a physiological parameter of claim 22, correlating the known pressure values between the transition points to body fluid compartment types.

24. The method of obtaining a physiological parameter of claim 22, wherein at least some of the transition points are correlated to body compartments indicative of blood vessel types.

25. The method of obtaining a physiological parameter of claim 24, wherein at least one of the characteristic body fluid compartment types is indicative of central venous pressure.

26. The method of obtaining a physiological parameter of claim 22, wherein the step of applying a series of pressures includes applying pressure above a systolic pressure of the body region.

27. The method of obtaining a physiological parameter to claim 26, wherein the body fluid indication values are admittance values and further including the step of graphing a first curve of admittance values to pressure values.

28. The method of obtaining a physiological parameter according to claim 27, further comprising the steps of:
   deriving a series of non-vascular fluid admittance values above the systolic pressure value, and
   graphing a second curve of the non-vascular fluid admittance values to the series of pressure values.

29. The method of obtaining a vascular fluid profile of claim 28, further including the step of subtracting the second curve from the first curve of admittance values to obtain a true representation of only vascular admittance values.

30. The method of obtaining a physiological parameter of claim 19, wherein the step of applying a series of pressures includes applying pressure starting below a lowest venous pressure of the body region.

31. The method of obtaining a physiological parameter of claim 22, wherein the sensing is done by bioimpedance.

32. The method of obtaining a physiological parameter of claim 22, further including the step of changing impedance values to admittance values.

33. The method of obtaining a physiological parameter of claim 22, further including the step of using the transition points to determine diastolic and mean pressure and deriving a vessel wall tension value therefrom.

34. The method of obtaining a physiological parameter of claim 22, wherein the step of referencing the body fluid volume indications to the series of known pressure values is done with a graphical representation.

35. The method of obtaining a physiological parameter of claim 22, wherein the body region is substantially at heart level when the series of pressures is applied.

36. The method of obtaining a physiological parameter of claim 22, wherein the body fluid indication values are referenced to the known pressure values when the pressure is increasing.

37. The method of obtaining a physiological parameter of claim 22, wherein the body fluid indication values are referenced to the known pressure values when the pressure is decreasing.

38. The method of obtaining a physiological parameter of claim 22, wherein the body fluid indication values are referenced to the known pressure values when the pressure is increasing and when the pressure is decreasing.

39. The method of obtaining a physiological parameter of claim 22, wherein the step of applying a series of pressures includes applying pressure above a mean pressure of a large artery.

40. The method of obtaining a physiological parameter according to claim 39, wherein the body fluid indication values are fluid volume values and further including the step of graphing a first curve of fluid volume values to pressure values.

41. The method of obtaining a physiological parameter according to claim 40, further comprising the steps of:
   deriving a series of non-vascular fluid volume values above the mean pressure value, and
   graphing a second curve of the non-vascular fluid volume values to the series of pressure values.

42. The method of obtaining a vascular fluid profile of claim 41, further including the step of subtracting the second curve from the first curve of fluid volume values to obtain a true representation of only vascular fluid volume values.

43. Apparatus for obtaining a physiological parameter, comprising:
   a. a pressure applicator for application of a series of pressures to a body region containing a body fluid so as to deplete a series of fluid volumes from a plurality of body fluid compartments in the body region, the pressure applicator including means for applying the pressures at a known value;
   b. a volume indicator for deriving body fluid volume indications of the plurality of body fluid compartments in the body region under pressure;
   c. means for referencing the body fluid volume indications to the applied pressure value; and
   d. means for identifying or displaying points at which a relationship of the body fluid volume indications referenced to the series of pressure values changes, thereby indicating state changes in a body fluid profile of the plurality of fluid compartments between two body fluid compartments having different fluid characteristics.

44. Apparatus for obtaining a physiological parameter according to claim 43, wherein the pressure applicator can apply a pressure below and above a large vein pressure.

45. Apparatus for obtaining a physiological parameter according to claim 43, wherein the pressure applicator includes an inflatable cuff with a width.

46. Apparatus for obtaining a physiological parameter according to claim 43, wherein the volume indicator is a bioimpedance sensor having a sensing channel located at or near the middle of the inflatable cuff width and the sensing channel is approximately one fifth the width of the inflatable cuff.

47. Apparatus for obtaining a physiological parameter according to claim 43, wherein the pressure applicator includes a mechanical pressure cuff.

48. Apparatus for obtaining a physiological parameter according to claim 43, wherein the pressure applicator and the volume indicator are coextensive.

49. Apparatus for obtaining a physiological parameter according to claim 43, wherein the pressure applicator includes means for applying a substantially consistent pressure across that area of the cuff coextensive with the volume indicator.

50. Apparatus for obtaining a physiological parameter according to claim 43, wherein the pressure applicator includes a pressure producing plate which cannot encircle a body region.

51. Apparatus for obtaining a physiological parameter according to claim 50, wherein the pressure producing plate further has impedance plethysmography leads coextensive therewith.

52. Apparatus for obtaining a physiological parameter according to claim 50, wherein the pressure producing plate is manually operated to apply force.

53. Apparatus for obtaining a physiological parameter according to claim 43, wherein the means for referencing the fluid volume indication value to the applied pressure value includes a computer.

54. Apparatus for obtaining a physiological parameter according to claim 43, wherein the volume indicator is not dependent upon receiving a pulsatile signal to derive the body fluid volume indication.

55. Apparatus for obtaining a physiological parameter, comprising:
   a. a monitor unit comprising:
      i) a system processor including:
         a volume state monitor for receiving data related to fluid volumes from, and sending control signals to, a volume indicator,
         a pressure state monitor for receiving data related to a pressure applicator,
         a pressure control unit for sending control signals to a pressure applicator,
         a system timer for producing time values related to control of the monitor unit,
         a volume/pressure analyzer for referencing pressure data to volume data, and
         an input/output interface for permitting operator interaction with the apparatus,
      ii) a volume sensor for applying a current source to a bioimpedance sensor, and iii) a pressure generator for producing force to be applied to a pressure applicator;

b. a pressure applicator for application of a contiguous series of pressures to a body region containing a plurality of body fluid compartments so as to deplete a series of fluid volumes from the plurality of body fluid compartments, the pressure applicator including means for applying the pressures at a known value to a body region;

c. a bioimpedance sensor for deriving body fluid volume indications of the plurality of body fluid compartments under pressure; and d. means for identifying or displaying points at which a relationship of the body fluid volume indications referenced to the contiguous series of pressures changes, thereby indicating state changes between two body fluid compartments having different fluid characteristics.

56. Apparatus for obtaining a physiological parameter according to claim 1, wherein the bioimpedance sensor has a sensing channel located at or near the middle of the inflatable cuff width and the sensing channel is approximately one fifth the width of the inflatable cuff.

57. Apparatus for obtaining a physiological parameter according to claim 55, wherein the pressure applicator is an inflatable cuff with a width.

58. A method of obtaining a physiological parameter of a body fluid compartment, comprising the steps of:

a. applying a series of known pressure values to a body region containing a body fluid to deplete or replenish a fluid volume from the body region;

b. sensing the body region under pressure to derive a series of static body fluid volume indications for the body region under pressure;

c. referencing the static body fluid volume indications to the series of known pressure values; and d. identifying a change in the relationship of the static body fluid volume indication values referenced to the series of pressure values, thereby indicating the physiological parameter in the body fluid compartment.

59. The method according to claim 58 wherein the body fluid compartments are adjacent.

60. The method according to claim 58 wherein the known pressure values are contiguous.

61. A method of obtaining a physiological parameter, comprising the steps of:

a. applying a series of known pressure values to a body region containing a body fluid to deplete or replenish a series of fluid volumes from the body region;

b. placing a plethysmographic device at the body region under pressure to derive a series of body fluid volume indication values of the body region under pressure;

c. referencing the body fluid volume indication values to the series of known pressure values; and d. identifying transition points at which a relationship of the body fluid volume indication values referenced to the series of known pressure values changes, thereby indicating state changes between two adjacent body fluid compartments having different fluid characteristics;

whereby at least one of the following physiological parameters is derived from the state changes:

a static fluid pressure selected from the group including: a fluid pressure of the capillaries, a fluid pressure of the venuoles, a fluid pressure of the small veins, a fluid pressure of the large veins, and a fluid pressure of the arterioles; and a fluid pressure of non-vascular fluid.

62. The method according to claim 61, whereby at least one of the following physiological parameters is further derived from the state changes:

a static fluid pressure selected from the group including: a fluid pressure of the small arteries, and a fluid pulsatile vessel blood pressure of the large arteries and wherein the physiological parameter of the large arteries is further selected from the group including: a mean blood pressure of the large arteries, a systolic blood pressure of the large arteries, and a diastolic blood pressure of the large arteries.

63. A method of obtaining a vascular fluid profile, comprising the steps of:

a. applying a series of known pressure values to a body region at or near a heart level of the body, to deplete or replenish a series of vascular fluid volumes from vascular fluid compartments in the body region;

b. placing a bioimpedance sensor on the body region under pressure to derive a series of impedance or admittance values of the body region under pressure;

c. graphing a first curve of the impedance or admittance values to the series of pressure values; and d. identifying transition points in the first curve thereby indicating state changes in a vascular fluid profile between two vascular fluid compartments having different characteristic vascular fluid pressures;

whereby at least one of the following physiological parameters are derived from the vascular fluid profile:

vessel compliance;

central venous pressure;

a static fluid pressure selected from the group including: a fluid pressure of the capillaries, a fluid pressure of the venuoles, a fluid pressure of the small veins, a fluid pressure of the large veins, and a fluid pressure of the arterioles;

a fluid pressure selected from the group including: a fluid pressure of the small arteries, and a fluid pulsatile vessel blood pressure of the large arteries and wherein the physiological parameter of the large arteries is further selected from the group including: a mean blood pressure of the large arteries, a systolic blood pressure of the large arteries, and a diastolic blood pressure of the large arteries; and a blood volume of the large arteries.

64. The method of obtaining a vascular fluid profile according to claim 63, further comprising the step of: graphing the first curve with admittance values.

65. The method of obtaining a vascular fluid profile according to claim 64, further comprising the steps of:

deriving a series of non-vascular fluid admittance values above a highest vascular pressure value, and graphing a second curve of the non-vascular fluid values to the series of pressure values.

66. The method of obtaining a vascular fluid profile of claim 65, further including the step of subtracting the second curve from the first curve of admittance values to obtain a true representation of only vascular admittance values.

67. A method of obtaining a physiological parameter of a body fluid compartment, comprising the steps of:

a. applying a contiguous series of known pressure values to a body region containing a body fluid to deplete or replenish a series of fluid volumes from adjacent body fluid compartments of the body region;

b. sensing the body region under pressure to derive a series of body fluid compartment volume indication values as changed by the pressure applied to or removed from the body region under pressure;

c. referencing the series of body fluid compartment volume indication values to the series of known pressure values; and d. identifying a change in the relationship of the series of body fluid compartment volume indication values referenced to the contiguous series of pressure values, thereby indicating the physiological parameter in the body fluid compartment.

* * * * *